(12) United States Patent
Jiang et al.

(10) Patent No.: US 10,544,137 B2
(45) Date of Patent: Jan. 28, 2020

(54) PI3K INHIBITOR, AND PHARMACEUTICALLY ACCEPTABLE SALT, POLYCRYSTALLINE FORM, AND APPLICATION THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Taotao Jiang, Shanghai (CN); Qiang Xu, Shanghai (CN); Zhaoling Dan, Shanghai (CN)

(73) Assignees: SHANGHAI HAIYAN PHARMACEUTICAL TECHNOLOGY CO., LTD. (KR); YANGTZE RIVER PHARMACEUTICAL GROUP CO., LTD. (KR)

( * ) Notice: Subject to any disclaimer, the term of this patent is extended or adjusted under 35 U.S.C. 154(b) by 0 days.

(21) Appl. No.: 16/098,103

(22) PCT Filed: May 31, 2017

(86) PCT No.: PCT/CN2017/086605
§ 371 (c)(1),
(2) Date: Oct. 31, 2018

(87) PCT Pub. No.: WO2017/206904
PCT Pub. Date: Dec. 7, 2017

(65) Prior Publication Data
US 2019/0152964 A1    May 23, 2019

(30) Foreign Application Priority Data
Jun. 2, 2016    (CN) .......................... 2016 1 0388018

(51) Int. Cl.
*C07D 413/14*    (2006.01)
*C07D 401/04*    (2006.01)
*A61P 35/02*    (2006.01)
*A61P 35/00*    (2006.01)
*A61K 31/5377*    (2006.01)

(52) U.S. Cl.
CPC ........ *C07D 413/14* (2013.01); *A61K 31/5377* (2013.01); *A61P 35/00* (2018.01); *A61P 35/02* (2018.01); *C07D 401/04* (2013.01); *C07B 2200/13* (2013.01)

(58) Field of Classification Search
CPC .......................... C07D 413/14; C07D 401/04; A61K 31/5377; C07B 2200/13; A61P 35/02; A61P 35/00
See application file for complete search history.

(56) References Cited

U.S. PATENT DOCUMENTS 10,227,324 B2 *    3/2019    Shen .................... C07D 401/14

FOREIGN PATENT DOCUMENTS

| CN | 101389622 A | 3/2009 |
|---|---|---|
| WO | 2009/066084 A1 | 5/2009 |
| WO | 2014/009147 A1 | 1/2014 |
| WO | 2016/095833 A1 | 6/2016 |

OTHER PUBLICATIONS

English translation of International Search Report for PCT/CN2017/086605, 3 pages.
International Search Report for PCT/CN2017/086605 (in Chinese), 4 pages.

* cited by examiner

*Primary Examiner* — Timothy R Rozof
(74) *Attorney, Agent, or Firm* — Adsero IP

(57) ABSTRACT

The present invention relates to a PI3K inhibitor, and a pharmaceutically acceptable salt, polycrystalline form, and application thereof. The invention specifically provides a polycrystalline form of 4-chloro-5-(6-(1-(methylsulfonyl)cyclopropyl)-2-morpholinopyrimidin-4-yl)pyridin-2-amine, a pharmaceutically acceptable salt thereof, or a polycrystalline form of the salt. The invention further discloses a pharmaceutical composition comprising the inhibitor and an application of the pharmaceutical composition.

7 Claims, 22 Drawing Sheets

PI3K INHIBITOR, AND PHARMACEUTICALLY ACCEPTABLE SALT, POLYCRYSTALLINE FORM, AND APPLICATION THEREOF

CROSS-REFERENCE TO RELATED APPLICATION

This application claims priority to and is a 35 U.S.C. § 371 national phase application of PCT/CN2017/086605 (WO 2017/206904 A1), filed on May 31, 2017 entitled "PI3K INHIBITOR, AND PHARMACEUTICALLY ACCEPTABLE SALT, POLYCRYSTALLINE FORM, AND APPLICATION THEREOF", which application claims priority to and the benefit of Chinese Application CN 201610388018.2 filed Jun. 2, 2016; the disclosures of which is incorporated herein by reference in their entirety.

TECHNICAL FIELD

The present disclosure belongs to the technical field of medicine. In particular, the present disclosure relates to a PI3K inhibitor, a pharmaceutically acceptable salt, a polymorph thereof, and a use thereof. The inhibitor is 4-chloro-5-(6-(1-(methylsulfonyl)cyclopropyl)-2-morpholinopyrimidin-4-yl)pyridin-2-amine.

BACKGROUND

With the deepening of tumor genetics and biology research, multiple intracellular tumor-related key signaling pathways have been found. Tumor cells rely on these pathways to achieve intracellular transduction of extracellular signals and regulate their own sustained proliferation, invasion, metastasis, anti-apoptosis, and other activities, thereby maintaining their malignant phenotypic characteristics on one hand and gaining tolerance against treatment through regulating specific genes and protein products thereof on the other hand. Studies have revealed that the transduction pathway mediated by the phosphatidylinositol 3-kinase (PI3K)-AKT-mammalian rapamycin target (mTOR) plays an important role in some cellular processes including proliferation and survival, and malfunction of these pathways is pathogenic factor for a wide range of human cancers and other disease profiles (Katso et al., Annual Rev. Cell Dev. BioL, 2001, 17: 615-617).

Phosphatidylinositol 3-kinase (PI3K) belongs to the family of lipokines and can be divided into three classes according to their structural characteristics and substrate selectivity. Class 1 PI3K, the most intensively studied, is a heterodimer protein which is composed of subunits with catalytic function (p110α, p110β, p110δ, and p110γ) and subunits with regulatory function (p85α, p85β, p50α, p55α, and p55γ), respectively. Type 1a PI3K enzyme subunits p100α and p100β are always co-expressed in various cell types, while the expression of p110δ is more restricted by leukocyte populations and some epithelial cells. Type 1b PI3K enzyme consists of p110γ catalytic subunit interacting with p101 regulatory subunit, and mainly distributes in leukocytes, platelets and cardiomyocytes. p85 regulatory subunit is activated via phosphorylation through interaction with the receptor tyrosine kinase. The amino terminus of p85 contains a SH3 domain and a proline enriched region which is capable of binding to the SH3 domain, and its carboxyl terminus contains two SH2 domains and one p110-binding region. The p110 subunit has homology with protein kinase, and this subunit itself has both serine/threonine protein kinase activity and phosphatidylinositol kinase activity, and can convert phosphatidylinositol diphosphate (PI2P) to phosphatidylinositol triphosphate (PI3P), wherein the latter can in turn activate a number of downstream signaling molecules, thereby accomplishing the continuing transmission of extracellular signals.

Studies have shown that Type 1a PI3K enzymes can directly or indirectly promote the occurrence of human cancer (Vivanco and Sawyers, Nature Reviews Cancer, 2002, 2, 489-501). For example, gene PIK3CA is widely amplified or mutated in various cancers, and the activation mutations in the catalytic site of the p110α subtype encoded by this gene are associated with various other tumors such as tumors of colon or rectum, mammary gland and lung. The expression of p110β is approximately 5% amplified in severe epithelial ovarian cancer, breast cancer and PTEN-lacking tumor cell lines. p110δ is associated with immuno-suppression and is commonly used in transplant rejection and autoimmune diseases. In addition to the direct effect, Type 1a PI3K can indirectly trigger tumors by causing a variety of downstream signaling events. For example, by activating Akt, PI3K-mediated signaling events are enhanced, leading to various cancers. A large number of studies have shown that different PI3K subtypes have different roles and the best way to inhibit the growth of malignant cells is to choose the inhibitors that are more specific to a certain p110 subtype than to broadly suppress all Type I PI3K enzymes (Susan and Kenneth, Cancer Treatment Reviews, 2013 Aug. 26. pii: S0305-7372 (13) 00171-0). Currently, unavoidable side effects have been observed for non-selective PI3K inhibitors in clinic, including nausea, vomiting, diarrhea, fatigue, elevated transaminases, hyperglycemia and the like which are commonly seen for PI3K inhibitors. Among the PI3K selective inhibitors, since PIK3CA/p110α is the most common PI3K mutant subtype, the PI3Kα selective inhibitors are also the ones that potentially have the most potent tumor-suppressing effect. At the same time, PI3Kα selective inhibitors can also, to the greatest extent, avoid pneumonia, neutropenia, thrombocytopenia, anemia, elevated transaminase and other side effects caused by PI3Kβ and PI3Kδ inhibitors in clinic (Brana and Siu, BMC Medicine, 2012, 10: 161).

PI3K is a key regulatory pathway for cell function. Its abnormal signaling is closely related to the activation of proto-oncogene, and PI3K thus has a critical effect on the onset and development of tumor. Therefore, it can be expected that developing small molecule compounds to inhibit PI3K as a tumor treatment drug has a promising prospect.

For PI3K signaling pathways, there are currently a number of compounds independently inhibiting PI3K activity under development and clinical trials. For example, the PI3K inhibitor, BKM-120, developed by Novartis, is now in phase III clinical stage for breast cancer. Another PI3K inhibitor, BYL-719, developed by Novartis for the treatment of solid tumors, and head and neck cancer, is also in clinical phase III now.

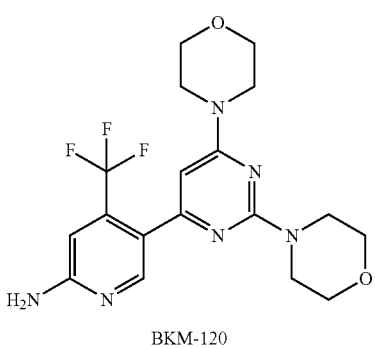 [SMILES: Nc1cc(C(F)(F)F)c(-c2cc(N3CCOCC3)nc(N3CCOCC3)n2)cn1]

BKM-120

Therefore, the development of medicaments against PI3K with higher activity, better selectivity, and less toxicity is of great significance.

SUMMARY

The object of the present disclosure is to provide an inhibitor that can effectively inhibit PI3K, a pharmaceutically acceptable salt, and a polymorph thereof, and uses thereof.

According to a first aspect of the present disclosure, a compound of formula X, or a pharmaceutically acceptable salt, or a polymorph thereof is provided:

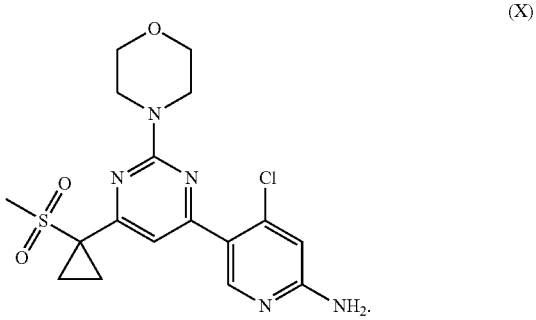 [SMILES: CS(=O)(=O)C1(c2cc(-c3cnc(N)cc3Cl)nc(N3CCOCC3)n2)CC1]

(X)

In another preferred embodiment, the pharmaceutically acceptable salt is selected from the group consisting of hydrochloride, sulfate, phosphate, acetate, L-lactate, maleate, fumarate, succinate, L-malate, adipate, L-tartrate, hippurate, citrate, mucate, glycollate, D-glucuronate, benzoate, gentisate, nicotinate, ethanedisulphonate, oxalate, methanesulfonate, benzenesulfonate, 2-hydroxyethanesulfonate, and hydrobromide.

In another preferred embodiment, the pharmaceutically acceptable salt is selected from the group consisting of hydrochloride, sulfate, hydrobromide, phosphate, methanesulfonate, maleate, L-tartrate, citrate, and fumarate.

In another preferred embodiment, the pharmaceutically acceptable salt is selected from the group consisting of hydrochloride, sulfate, maleate, and fumarate.

In another preferred embodiment, the compound of formula X, or the pharmaceutically acceptable salt, or the polymorph thereof is in an anhydrous form, a hydrate form or a solvate form.

In another preferred embodiment, the polymorph is a polymorph of the compound of formula X.

In another preferred embodiment, the polymorph is a polymorph of the pharmaceutically acceptable salt of the compound of formula X, and the pharmaceutically acceptable salt is selected from the group consisting of hydrochloride, sulfate, hydrobromide, phosphate, methanesulfonate, maleate, L-tartrate, citrate, and fumarate.

In another preferred embodiment, the polymorph is a polymorph of the pharmaceutically acceptable salt of the compound of formula X, and the pharmaceutically acceptable salt is selected from the group consisting of hydrochloride, sulfate, maleate, and fumarate.

In another preferred embodiment, the pharmaceutically acceptable salt is a hydrochloride, wherein a molar ratio of hydrochloric acid to the compound of formula X is (0.8-1.2): 1, preferably (0.9-1.1): 1.

In another preferred embodiment, the pharmaceutically acceptable salt is a sulfate, wherein a molar ratio of sulfuric acid to the compound of formula X is (0.2-1.1): 1, preferably (0.3-0.8): 1.

In another preferred embodiment, the pharmaceutically acceptable salt is a methanesulfonate, wherein a molar ratio of methanesulfonic acid to the compound of formula X is (0.8-1.2): 1, preferably (0.9-1.1): 1.

In another preferred embodiment, the pharmaceutically acceptable salt is a maleate, wherein a molar ratio of maleic acid to the compound of formula X is (0.7-1.3): 1, preferably (0.8-1.1): 1.

In another preferred embodiment, the pharmaceutically acceptable salt is an L-tartrate, wherein a molar ratio of L-tartaric acid to the compound of formula X is (0.8-1.2): 1, preferably (0.9-1.1): 1.

In another preferred embodiment, the pharmaceutically acceptable salt is a fumarate, wherein a molar ratio of fumaric acid to the compound of formula X is (0.2-1.1): 1, preferably (0.3-0.8): 1.

In another preferred embodiment, the pharmaceutically acceptable salt is a hydrobromide, wherein a molar ratio of hydrobromic acid to the compound of formula X is (0.8-1.2): 1, preferably (0.9-1.1): 1.

In another preferred embodiment, the pharmaceutically acceptable salt is a phosphate, wherein a molar ratio of phosphoric acid to the compound of formula X is 1: (0.9-2.1), preferably 1: (1.1-2.1).

In another preferred embodiment, the pharmaceutically acceptable salt is a citrate, wherein a molar ratio of citric acid to the compound of formula X is 1: (0.9-2.1), preferably 1: (1.1-2.1).

In another preferred embodiment, the polymorph is a form A crystal of the hydrochloride of the compound of formula X, i.e., crystal form A, which has an X-ray powder diffraction pattern including diffraction angle 2θ(°) values of the following group A1: 5.57±0.10, 8.87±0.10, 20.77±0.10, 22.09±0.10, 24.15±0.10, and 28.27±0.10.

In another preferred embodiment, the X-ray powder diffraction pattern of the crystal form A further includes two or more diffraction angle 2θ(°) values selected from the following group A2: 25.19±0.10, 30.88±0.10, and 31.37±0.10.

In another preferred embodiment, the X-ray powder diffraction pattern of the crystal form A further includes two or more diffraction angle 2θ(°) values selected from the following group A3: 16.55±0.10, 17.01±0.10, 22.84±0.10, 25.55±0.10, 26.70±0.10, and 37.90±0.10.

In another preferred embodiment, the X-ray powder diffraction pattern of the crystal form A includes six or more or all (such as 6, 7, 8, 9, 11, 12, 13, 14, 15, etc.) 2θ(°) values selected from the group A1, A2, and A3.

In another preferred embodiment, the X-ray powder diffraction pattern of the crystal form A has the 2θ(°) values shown in Table A-1 below:

TABLE A-1

| 2θ(°) | d value [Å] | relative intensity [%] |
|---|---|---|
| 5.57 | 15.87 | S |
| 9.38 | 9.42 | W |
| 12.56 | 7.04 | W |
| 16.55 | 5.35 | M |
| 18.06 | 4.91 | W |
| 20.77 | 4.27 | S |
| 22.09 | 4.02 | VS |
| 24.15 | 3.68 | S |
| 25.55 | 3.48 | W |
| 27.89 | 3.20 | W |
| 28.88 | 3.09 | W |
| 31.37 | 2.85 | M |
| 34.99 | 2.56 | W |
| 37.90 | 2.37 | W |
| 8.87 | 9.96 | S |
| 11.07 | 7.98 | W |
| 14.72 | 6.01 | W |
| 17.01 | 5.21 | M |
| 18.75 | 4.73 | W |
| 21.48 | 4.13 | W |
| 22.84 | 3.89 | M |
| 25.19 | 3.53 | M |
| 26.70 | 3.34 | M |
| 28.27 | 3.15 | S |
| 30.88 | 2.89 | M |
| 34.26 | 2.62 | W |
| 37.38 | 2.40 | W |

In another preferred embodiment, the X-ray powder diffraction pattern of the crystal form A is substantially characterized as in FIG. 1.

In another preferred embodiment, the molar ratio of hydrochloric acid to the compound of formula X in the crystal form A is (0.8-1.2): 1, preferably (0.9-1.1): 1.

In another preferred embodiment, the crystal form A further has one or more features selected from the group consisting of:

(i) differential scanning calorimetry analysis spectrum is substantially characterized as in FIG. 2B; and (ii) thermogravimetric analysis spectrum is substantially characterized as in FIG. 2B.

In another preferred embodiment, the crystal form A is in an anhydrous form.

In another preferred embodiment, the polymorph is a form B-1 crystal of the sulfate of the compound of formula X, i.e., crystal form B-1, which has an X-ray powder diffraction pattern including diffraction angle 2θ(°) values of the following group B1: 9.83±0.10, 18.51±0.10, 21.11±0.10, 21.75±0.10, and 27.29±0.10.

In another preferred embodiment, the X-ray powder diffraction pattern of the crystal form B-1 further includes two or more diffraction angle 2θ(°) values selected from the following group B2: 5.43±0.10, 23.54±0.10, and 24.44±0.10.

In another preferred embodiment, the X-ray powder diffraction pattern of the crystal form B-1 further includes two or more diffraction angle 2θ(°) values selected from the following group B3: 7.94±0.10, 14.52±0.10, 15.07±0.10, 16.66±0.10, 28.73±0.10, 29.08±0.10, and 30.07±0.10.

In another preferred embodiment, the X-ray powder diffraction pattern of the crystal form B-1 includes six or more or all (such as 6, 7, 8, 9, 11, 12, 13, 14, 15, etc.) 2θ(°) values selected from the group B1, B2, and B3.

In another preferred embodiment, the X-ray powder diffraction pattern of the crystal form B-1 has the 2θ(°) values shown in Table B-1 below:

TABLE B-1

| 2θ(°) | d value [Å] | relative intensity [%] |
|---|---|---|
| 5.43 | 16.26 | S |
| 9.83 | 8.99 | VS |
| 14.52 | 6.10 | M |
| 16.66 | 5.31 | M |
| 18.51 | 4.79 | VS |
| 21.75 | 4.08 | VS |
| 24.44 | 3.64 | S |
| 28.73 | 3.10 | M |
| 30.07 | 2.97 | M |
| 32.67 | 2.74 | W |
| 35.01 | 2.56 | W |
| 7.94 | 11.12 | M |
| 10.87 | 8.13 | W |
| 15.07 | 5.87 | M |
| 17.07 | 5.19 | W |
| 21.11 | 4.20 | S |
| 23.54 | 3.78 | S |
| 27.29 | 3.27 | S |
| 29.08 | 3.07 | M |
| 32.06 | 2.79 | W |
| 33.71 | 2.66 | W |
| 38.83 | 2.32 | W |

In another preferred embodiment, the X-ray powder diffraction pattern of the crystal form B-1 is substantially characterized as in FIG. 3.

In another preferred embodiment, the molar ratio of sulfuric acid to the compound of formula X in the crystal form B-1 is (0.2-1.1): 1, preferably (0.3-0.8): 1.

In another preferred embodiment, the crystal form B-1 further has one or more features selected from the group consisting of:

(i) differential scanning calorimetry analysis spectrum is substantially characterized as in FIG. 4B; and (ii) thermogravimetric analysis spectrum is substantially characterized as in FIG. 4B.

In another preferred embodiment, the crystal form B-1 is in an anhydrous form.

In another preferred embodiment, the polymorph is a form B-2 crystal of the sulfate of the compound of formula X, i.e., crystal form B-2, which has an X-ray powder diffraction pattern including diffraction angle 2θ(°) values of the following group B1': 16.42±0.10, 20.17±0.10, 22.25±0.10, 23.00±0.10, 23.97±0.10, 25.30±0.10, and 27.98±0.10.

In another preferred embodiment, the X-ray powder diffraction pattern of the crystal form B-2 further includes two or more diffraction angle 2θ(°) values selected from the following group B2': 21.08±0.10, 25.89±0.10, and 32.14±0.10.

In another preferred embodiment, the X-ray powder diffraction pattern of the crystal form B-2 includes six or more or all (such as 6, 7, 8, 9, 10, etc.) 2θ(°) values selected from the group B1' and B2'.

In another preferred embodiment, the X-ray powder diffraction pattern of the crystal form B-2 has the 2θ(°) values shown in Table B-2 below:

TABLE B-2

| 2θ(°) | d value [Å] | relative intensity [%] |
|---|---|---|
| 8.86 | 9.97 | W |
| 15.27 | 5.80 | W |
| 17.57 | 5.04 | W |
| 20.17 | 4.40 | VS |

TABLE B-2-continued

| 2θ(°) | d value [Å] | relative intensity [%] |
|---|---|---|
| 22.25 | 3.99 | S |
| 23.97 | 3.71 | M |
| 25.89 | 3.44 | M |
| 28.46 | 3.13 | W |
| 32.14 | 2.78 | M |
| 38.06 | 2.36 | W |
| 12.49 | 7.08 | W |
| 16.42 | 5.39 | S |
| 19.05 | 4.65 | W |
| 21.08 | 4.21 | M |
| 23.00 | 3.86 | M |
| 25.30 | 3.52 | M |
| 27.98 | 3.19 | M |
| 30.52 | 2.93 | W |
| 34.61 | 2.59 | W |
| 39.14 | 2.30 | W |

In another preferred embodiment, the X-ray powder diffraction pattern of the crystal form B-2 is substantially characterized as in FIG. 5.

In another preferred embodiment, the molar ratio of sulfuric acid to the compound of formula X in the crystal form B-2 is (0.2-1.1): 1, preferably (0.3-0.8): 1.

In another preferred embodiment, the crystal form B-2 is in an anhydrous form.

In another preferred embodiment, the polymorph is a form C crystal of the maleate of the compound of formula X, i.e., crystal form C, which has an X-ray powder diffraction pattern including diffraction angle 2θ(°) values of the following group C1: 8.35±0.10, 8.92±0.10, 16.91±0.10, 20.35±0.10, 21.40±0.10, 23.70±0.10, 24.98±0.10, and 25.47±0.10.

In another preferred embodiment, the X-ray powder diffraction pattern of the crystal form C further includes two or more diffraction angle 2θ(°) values selected from the following group C2: 15.96±0.10, 16.61±0.10, 17.87±0.10, 18.86±0.10, and 28.59±0.10.

In another preferred embodiment, the X-ray powder diffraction pattern of the crystal form C further includes two or more diffraction angle 2θ(°) values selected from the following group C3: 31.38±0.10, 33.52±0.10, and 34.16±0.10.

In another preferred embodiment, the X-ray powder diffraction pattern of the crystal form C includes six or more or all (such as 6, 7, 8, 9, 10, 11, 12, 13, 14, 15, etc.) 2θ(°) values selected from the group C1, C2 and C3.

In another preferred embodiment, the X-ray powder diffraction pattern of the crystal form C has the 2θ(°) values shown in Table C-1 below:

TABLE C-1

| 2θ(°) | d value [Å] | relative intensity [%] |
|---|---|---|
| 8.35 | 10.59 | VS |
| 14.48 | 6.11 | W |
| 16.61 | 5.33 | S |
| 17.87 | 4.96 | M |
| 19.25 | 4.61 | W |
| 21.40 | 4.15 | S |
| 23.70 | 3.75 | S |
| 24.98 | 3.56 | S |
| 27.01 | 3.30 | W |
| 29.43 | 3.03 | W |
| 32.08 | 2.79 | W |
| 34.16 | 2.62 | M |
| 37.73 | 2.38 | W |
| 8.92 | 9.90 | S |
| 15.96 | 5.55 | M |
| 16.91 | 5.24 | S |
| 18.86 | 4.70 | M |
| 20.35 | 4.36 | S |
| 21.95 | 4.04 | W |
| 24.19 | 3.68 | W |
| 25.47 | 3.49 | S |
| 28.59 | 3.12 | M |
| 31.38 | 2.85 | M |
| 33.52 | 2.67 | M |
| 35.77 | 2.51 | W |
| 38.14 | 2.36 | W |

In another preferred embodiment, the X-ray powder diffraction pattern of the crystal form C is substantially characterized as in FIG. 6.

In another preferred embodiment, the molar ratio of maleic acid to the compound of formula X in the crystal form C is (0.7-1.3): 1, preferably (0.8-1.1): 1.

In another preferred embodiment, the crystal form C further has one or more features selected from the group consisting of:

(i) differential scanning calorimetry analysis spectrum is substantially characterized as in FIG. 7B;

(ii) thermogravimetric analysis spectrum is substantially characterized as in FIG. 7B; and (iii) the crystal form C has a melting point of 198° C. to 208° C., preferably 200° C. to 206° C.

In another preferred embodiment, the crystal form C is in an anhydrous form.

In another preferred embodiment, the polymorph is a form D-1 crystal of the fumarate of the compound of formula X, i.e., crystal form D-1, which has an X-ray powder diffraction pattern including diffraction angle 2θ(°) values of the following group D1: 9.07±0.10, 12.48±0.10, 16.85±0.10, 18.93±0.10, 20.07±0.10, 21.21±0.10, 22.96±0.10, 25.56±0.10, 27.50±0.10, 30.72±0.10, 31.45±0.10, and 32.69±0.10.

In another preferred embodiment, the X-ray powder diffraction pattern of the crystal form D-1 further includes two or more diffraction angle 2θ(°) values selected from the following group D2: 15.31±0.10, 17.52±0.10, and 18.28±0.10.

In another preferred embodiment, the X-ray powder diffraction pattern of the crystal form D-1 includes six or more or all (such as 6, 7, 8, 9, 10, 11, 12, 13, 14, 15, etc.) 2θ(°) values selected from the group D1 and D2.

In another preferred embodiment, the X-ray powder diffraction pattern of the crystal form D-1 has the 2θ(°) values shown in Table D-1 below:

TABLE D-1

| 2θ(°) | d value [Å] | relative intensity [%] |
|---|---|---|
| 6.21 | 14.22 | W |
| 9.07 | 9.75 | VS |
| 10.64 | 8.30 | W |
| 12.48 | 7.08 | S |
| 16.85 | 5.26 | VS |
| 18.28 | 4.85 | M |
| 20.07 | 4.42 | VS |
| 22.96 | 3.87 | S |
| 25.56 | 3.48 | S |
| 28.92 | 3.09 | W |

TABLE D-1-continued

| 2θ(°) | d value [Å] | relative intensity [%] |
|---|---|---|
| 31.45 | 2.84 | S |
| 34.45 | 2.60 | W |
| 38.99 | 2.31 | W |
| 6.75 | 13.09 | W |
| 9.67 | 9.14 | W |
| 11.69 | 7.57 | W |
| 15.31 | 5.78 | S |
| 17.52 | 5.06 | M |
| 18.93 | 4.68 | VS |
| 21.21 | 4.19 | VS |
| 24.34 | 3.65 | W |
| 27.50 | 3.24 | S |
| 30.72 | 2.91 | M |
| 32.69 | 2.74 | S |
| 36.20 | 2.48 | W |
| 39.45 | 2.28 | M |

In another preferred embodiment, the X-ray powder diffraction pattern of the crystal form D-1 is substantially characterized as in FIG. 8.

In another preferred embodiment, the molar ratio of fumaric acid to the compound of formula X in the crystal form D-1 is (0.2-1.1): 1, preferably (0.3-0.8): 1.

In another preferred embodiment, the polymorph is a form D-2 crystal of the fumarate of the compound of formula X, i.e., crystal form D-2, which has an X-ray powder diffraction pattern including diffraction angle 2θ(°) values of the following group D1': 14.76±0.10, 19.74±0.10, and 26.69±0.10.

In another preferred embodiment, the X-ray powder diffraction pattern of the crystal form D-2 further includes two or more diffraction angle 2θ(°) values selected from the following group D2': 26.34±0.10, and 29.82±0.10.

In another preferred embodiment, the X-ray powder diffraction pattern of the crystal form D-2 further includes two or more diffraction angle 2θ(°) values selected from the following group D3': 21.68±0.10, 22.29±0.10, 25.34±0.10, and 34.96±0.10.

In another preferred embodiment, the X-ray powder diffraction pattern of the crystal form D-2 includes six or more or all (such as 6, 7, 8, 9, etc.) 2θ(°) values selected from the group D1', D2', and D3'.

In another preferred embodiment, the X-ray powder diffraction pattern of the crystal form D-2 has the 2θ(°) values shown in Table D-2 below:

TABLE D-2

| 2θ(°) | d value [Å] | relative intensity [%] |
|---|---|---|
| 4.88 | 18.11 | W |
| 14.76 | 6.00 | VS |
| 21.68 | 4.10 | M |
| 23.69 | 3.75 | W |
| 26.34 | 3.38 | M |
| 29.82 | 2.99 | M |
| 39.47 | 2.28 | W |
| 10.10 | 8.75 | W |
| 19.74 | 4.49 | VS |
| 22.29 | 3.98 | M |
| 25.34 | 3.51 | M |
| 26.69 | 3.33 | S |
| 34.96 | 2.56 | M |

In another preferred embodiment, the X-ray powder diffraction pattern of the crystal form D-2 is substantially characterized as in FIG. 9.

In another preferred embodiment, the molar ratio of fumaric acid to the compound of formula X in the crystal form D-2 is (0.2-1.1): 1, preferably (0.3-0.8): 1.

In another preferred embodiment, the crystal form D-2 further has one or more features selected from consisting of:

(i) differential scanning calorimetry analysis spectrum is substantially characterized as in FIG. 10B;

(ii) thermogravimetric analysis spectrum is substantially characterized as in FIG. 10B; and (iii) the crystal form D-2 has a melting point of 231° C. to 241° C., preferably 233° C. to 239° C.

In another preferred embodiment, the crystal form D-2 is in an anhydrous form.

In another preferred embodiment, the polymorph is a form E crystal of the methanesulfonate of the compound of formula X, i.e., crystal form E, which has an X-ray powder diffraction pattern including diffraction angle 2θ(°) values of the following group E1: 7.92±0.10, 16.07±0.10, 18.74±0.10, 20.25±0.10, 20.61±0.10, 22.08±0.10, 24.30±0.10, and 31.04±0.10.

In another preferred embodiment, the X-ray powder diffraction pattern of the crystal form E further includes two or more diffraction angle 2θ(°) values selected from the following group E2: 7.60±0.10, 10.17±0.10, 15.05±0.10, 15.41±0.10, 30.25±0.10, 30.58±0.10, and 33.08±0.10.

In another preferred embodiment, the X-ray powder diffraction pattern of the crystal form E includes six or more or all (such as 6, 7, 8, 9, 10, 11, 12, 13, 14, 15, etc.) 2θ(°) values selected from the group E1 and E2.

In another preferred embodiment, the X-ray powder diffraction pattern of the crystal form E has the 2θ(°) values shown in Table E-1 below:

TABLE E-1

| 2θ(°) | d value [Å] | relative intensity [%] |
|---|---|---|
| 7.60 | 11.63 | S |
| 10.17 | 8.69 | S |
| 15.05 | 5.88 | S |
| 16.07 | 5.51 | S |
| 20.25 | 4.38 | VS |
| 22.08 | 4.02 | S |
| 22.83 | 3.89 | W |
| 25.18 | 3.53 | W |
| 27.41 | 3.25 | W |
| 28.77 | 3.10 | W |
| 30.25 | 2.95 | M |
| 31.04 | 2.88 | S |
| 33.48 | 2.67 | W |
| 36.21 | 2.48 | W |
| 38.52 | 2.33 | W |
| 7.92 | 11.15 | VS |
| 14.17 | 6.25 | W |
| 15.41 | 5.74 | S |
| 18.74 | 4.73 | VS |
| 20.61 | 4.31 | S |
| 22.53 | 3.94 | W |
| 24.30 | 3.66 | S |
| 26.13 | 3.40 | W |
| 28.10 | 3.17 | W |
| 29.58 | 3.02 | W |
| 30.58 | 2.92 | M |
| 33.08 | 2.70 | M |
| 35.03 | 2.56 | W |
| 37.96 | 2.37 | W |
| 39.45 | 2.28 | W |

In another preferred embodiment, the X-ray powder diffraction pattern of the crystal form E is substantially characterized as in FIG. 11.

In another preferred embodiment, the molar ratio of methanesulfonic acid to the compound of formula X in the crystal form E is (0.8-1.2): 1, preferably (0.9-1.1): 1.

In another preferred embodiment, the crystal form E further has one or more features selected from consisting of:
(i) differential scanning calorimetry analysis spectrum is substantially characterized as in FIG. 12B;
(ii) thermogravimetric analysis spectrum is substantially characterized as in FIG. 12B; and
(iii) the crystal form E has a melting point of 243° C. to 253° C., preferably 245° C. to 251° C.

In another preferred embodiment, the crystal form E is in an anhydrous form.

In another preferred embodiment, the polymorph is a form F crystal of the L-tartrate of the compound of formula X, i.e., crystal form F, which has an X-ray powder diffraction pattern including diffraction angle 2θ(°) values of the following group F1: 11.22±0.10, 19.80±0.10, 20.35±0.10, 20.66±0.10, and 23.44±0.10.

In another preferred embodiment, the X-ray powder diffraction pattern of the crystal form F further includes two or more diffraction angle 2θ(°) values selected from the following group F2: 15.42±0.10, 17.42±0.10, 19.11±0.10, 22.69±0.10, 27.21±0.10, 27.63±0.10, 31.02±0.10, and 31.28±0.10.

In another preferred embodiment, the X-ray powder diffraction pattern of the crystal form F includes six or more or all (such as 6, 7, 8, 9, 10, 11, 12, 13, etc.) 2θ(°) values selected from the group F1 and F2.

In another preferred embodiment, the X-ray powder diffraction pattern of the crystal form F has the 2θ(°) values shown in Table F-1 below:

TABLE F-1

| 2θ(°) | d value [Å] | relative intensity [%] |
|---|---|---|
| 5.07 | 17.43 | W |
| 11.22 | 7.88 | VS |
| 15.42 | 5.74 | M |
| 17.42 | 5.09 | M |
| 19.80 | 4.48 | VS |
| 20.66 | 4.30 | VS |
| 22.69 | 3.91 | M |
| 24.70 | 3.60 | W |
| 26.53 | 3.36 | W |
| 27.63 | 3.22 | M |
| 29.61 | 3.01 | W |
| 31.28 | 2.86 | M |
| 33.90 | 2.64 | W |
| 35.48 | 2.53 | W |
| 37.46 | 2.40 | W |
| 8.63 | 10.23 | W |
| 14.68 | 6.03 | W |
| 16.70 | 5.30 | w |
| 19.11 | 4.64 | M |
| 20.35 | 4.36 | S |
| 22.24 | 3.99 | W |
| 23.44 | 3.79 | S |
| 25.40 | 3.50 | W |
| 27.21 | 3.27 | M |
| 28.37 | 3.14 | W |
| 31.02 | 2.88 | M |
| 33.17 | 2.70 | W |
| 34.38 | 2.61 | W |
| 37.12 | 2.42 | W |

In another preferred embodiment, the X-ray powder diffraction pattern of the crystal form F is substantially characterized as in FIG. 13.

In another preferred embodiment, the molar ratio of L-tartaric acid to the compound of formula X in the crystal form F is (0.8-1.2): 1, preferably (0.9-1.1): 1.

In another preferred embodiment, the crystal form F further has one or more features selected from the following group:
(i) differential scanning calorimetry analysis spectrum is substantially characterized as in FIG. 14B;
(ii) thermogravimetric analysis spectrum is substantially characterized as in FIG. 14B; and
(iii) the crystal form F has a melting point of 192° C.-202° C., preferably 194° C.-200° C.

In another preferred embodiment, the crystal form F is in an anhydrous form.

In another preferred embodiment, the polymorph is a form G-1 crystal of the phosphate of the compound of formula X, i.e., crystal form G-1, which has an X-ray powder diffraction pattern including diffraction angle 2θ(°) values of the following group G1: 9.43±0.10, 17.30±0.10, 18.82±0.10, 19.41±0.10, 20.91±0.10, 22.40±0.10, 27.44±0.10, and 29.43±0.10.

In another preferred embodiment, the X-ray powder diffraction pattern of the crystal form G-1 further includes two or more diffraction angle 2θ(°) values selected from the following group G2: 15.32±0.10, 23.85±0.10, 24.35±0.10, 30.61±0.10, 31.07±0.10, and 33.41±0.10.

In another preferred embodiment, the X-ray powder diffraction pattern of the crystal form G-1 includes six or more or all (such as 6, 7, 8, 9, 10, 11, 12, 13, 14, etc.) 2θ(°) values selected from the group G1 and G2.

In another preferred embodiment, the X-ray powder diffraction pattern of the crystal form G-1 has the 2θ(°) values shown in Table G-1 below:

TABLE G-1

| 2θ(°) | d value [Å] | relative intensity [%] |
|---|---|---|
| 5.09 | 17.34 | W |
| 7.45 | 11.86 | W |
| 11.24 | 7.87 | W |
| 13.66 | 6.48 | W |
| 16.37 | 5.41 | W |
| 18.82 | 4.71 | S |
| 20.91 | 4.24 | S |
| 23.39 | 3.80 | W |
| 24.35 | 3.65 | M |
| 25.99 | 3.43 | W |
| 29.43 | 3.03 | S |
| 31.07 | 2.88 | M |
| 34.42 | 2.60 | W |
| 36.20 | 2.48 | W |
| 38.97 | 2.31 | W |
| 5.65 | 15.63 | W |
| 9.43 | 9.37 | VS |
| 13.06 | 6.77 | W |
| 15.32 | 5.78 | M |
| 17.30 | 5.12 | VS |
| 19.41 | 4.57 | S |
| 22.40 | 3.97 | VS |
| 23.85 | 3.73 | M |
| 25.20 | 3.53 | W |
| 27.44 | 3.25 | S |
| 30.61 | 2.92 | M |
| 33.41 | 2.68 | M |
| 35.38 | 2.54 | W |
| 38.35 | 2.35 | W |

In another preferred embodiment, the X-ray powder diffraction pattern of the crystal form G-1 is substantially characterized as in FIG. 15.

In another preferred embodiment, the molar ratio of phosphoric acid to the compound of formula X in the crystal form G-1 is 1: (0.9-2.1), preferably 1: (1.1-2.1).

In another preferred embodiment, the polymorph is a form G-2 crystal of the phosphate of the compound of formula X, i.e., crystal form G-2, which has an X-ray powder diffraction pattern including diffraction angle 2θ(°) values of the following group G1': 19.26±0.10, 21.00±0.10, and 24.15±0.10.

In another preferred embodiment, the X-ray powder diffraction pattern of the crystal form G-2 further includes two or more diffraction angle 2θ(°) values selected from the following group G2': 16.00±0.10, 16.44±0.10, 21.89±0.10, 23.70±0.10, 27.19±0.10, 27.58±0.10, and 30.38±0.10.

In another preferred embodiment, the X-ray powder diffraction pattern of the crystal form G-2 includes six or more or all (such as 6, 7, 8, 9, 10, etc.) 2θ(°) values selected from the group G1' and G2'.

In another preferred embodiment, the X-ray powder diffraction pattern of the crystal form G-2 has the 2θ(°) values shown in Table G-2 below:

TABLE G-2

| 2θ(°) | d value [Å] | relative intensity [%] |
|---|---|---|
| 5.18 | 17.05 | W |
| 8.95 | 9.88 | W |
| 11.29 | 7.83 | W |
| 12.35 | 7.16 | W |
| 16.44 | 5.39 | M |
| 19.26 | 4.60 | VS |
| 21.89 | 4.06 | M |
| 23.70 | 3.75 | M |
| 25.47 | 3.49 | W |
| 27.58 | 3.23 | M |
| 28.87 | 3.09 | W |
| 30.38 | 2.94 | M |
| 32.47 | 2.76 | W |
| 34.42 | 2.60 | W |
| 35.72 | 2.51 | W |
| 38.39 | 2.34 | W |
| 5.61 | 15.75 | W |
| 9.53 | 9.27 | W |
| 11.83 | 7.48 | W |
| 16.00 | 5.53 | M |
| 18.11 | 4.90 | W |
| 21.00 | 4.23 | VS |
| 22.46 | 3.96 | W |
| 24.15 | 3.68 | S |
| 27.19 | 3.28 | M |
| 28.22 | 3.16 | W |
| 29.85 | 2.99 | W |
| 31.57 | 2.83 | W |
| 33.48 | 2.67 | W |
| 35.32 | 2.54 | W |
| 36.67 | 2.49 | W |
| 39.16 | 2.30 | W |

In another preferred embodiment, the X-ray powder diffraction pattern of the crystal form G-2 is substantially characterized as in FIG. 16.

In another preferred embodiment, the molar ratio of phosphoric acid to the compound of formula X in the crystal form G-2 is 1: (0.9-2.1), preferably 1: (1.1-2.1).

In another preferred embodiment, the polymorph is a form G-3 crystal of the phosphate of the compound of formula X, i.e., crystal form G-3, which has an X-ray powder diffraction pattern including diffraction angle 2θ(°) values of the following group G1": 15.11±0.10, 16.16±0.10, 18.84±0.10, 19.90±0.10, 21.32±0.10, 23.40±0.10, 24.21±0.10, 24.75±0.10, 26.16±0.10, and 30.55±0.10.

In another preferred embodiment, the X-ray powder diffraction pattern of the crystal form G-3 further includes two or more diffraction angle 2θ(°) values selected from the following group G2": 11.62±0.10, 21.70±0.10, 25.89±0.10, 27.75±0.10, 29.09±0.10, 30.99±0.10, 31.86±0.10, 32.48±0.10, and 38.41±0.10.

In another preferred embodiment, the X-ray powder diffraction pattern of the crystal form G-3 includes six or more or all (such as 6, 7, 8, 9, 10, 11, 12, 13, 14, 15, 16, 17, 18, 19, etc.) 2θ(°) values selected from the group G1" and G2".

In another preferred embodiment, the X-ray powder diffraction pattern of the crystal form G-3 has the 2θ(°) values shown in Table G-3 below:

TABLE G-3

| 2θ(°) | d value [Å] | relative intensity [%] |
|---|---|---|
| 4.43 | 19.95 | W |
| 7.98 | 11.07 | S |
| 15.11 | 5.86 | VS |
| 17.31 | 5.12 | W |
| 19.90 | 4.46 | S |
| 21.70 | 4.09 | S |
| 24.21 | 3.67 | VS |
| 25.89 | 3.44 | M |
| 27.15 | 3.28 | W |
| 29.09 | 3.07 | S |
| 30.99 | 2.88 | M |
| 32.48 | 2.75 | M |
| 35.47 | 2.53 | W |
| 39.54 | 2.28 | W |
| 5.73 | 15.40 | W |
| 11.62 | 7.61 | S |
| 16.16 | 5.48 | VS |
| 18.84 | 4.71 | S |
| 21.32 | 4.16 | S |
| 23.40 | 3.80 | VS |
| 24.75 | 3.59 | S |
| 26.16 | 3.40 | S |
| 27.75 | 3.21 | S |
| 30.55 | 2.92 | S |
| 31.86 | 2.81 | M |
| 33.53 | 2.67 | W |
| 38.41 | 2.34 | S |

In another preferred embodiment, the X-ray powder diffraction pattern of the crystal form G-3 is substantially characterized as in FIG. 17.

In another preferred embodiment, the molar ratio of phosphoric acid to the compound of formula X in the crystal form G-3 is 1: (0.9-2.1), preferably 1: (1.1-2.1).

In another preferred embodiment, the polymorph is a form H-1 crystal of the citrate of the compound of formula X, i.e., crystal form H-1, which has an X-ray powder diffraction pattern including diffraction angle 2θ(°) values of the following group H1: 14.01±0.10, 21.04±0.10, 28.26±0.10, and 35.54±0.10.

In another preferred embodiment, the X-ray powder diffraction pattern of the crystal form H-1 further includes two or more diffraction angle 2θ(°) values selected from the following group H2: 16.14±0.10, 18.64±0.10, 29.78±0.10, 31.81±0.10, and 32.10±0.10.

In another preferred embodiment, the X-ray powder diffraction pattern of the crystal form H-1 includes six or more or all (such as 6, 7, 8, 9, etc.) 2θ(°) values selected from the group H1 and H2.

In another preferred embodiment, the X-ray powder diffraction pattern of the crystal form H-1 has the 2θ(°) values shown in Table H-1 below:

TABLE H-1

| 2θ(°) | d value [Å] | relative intensity [%] |
|---|---|---|
| 10.37 | 8.53 | W |
| 14.01 | 6.32 | M |
| 16.14 | 5.49 | M |
| 18.64 | 4.76 | M |
| 21.04 | 4.22 | S |
| 22.68 | 3.92 | W |
| 25.32 | 3.51 | W |
| 27.58 | 3.23 | W |
| 29.78 | 3.00 | M |
| 32.10 | 2.79 | M |
| 34.56 | 2.59 | W |
| 38.99 | 2.31 | W |
| 12.40 | 7.13 | W |
| 15.04 | 5.89 | W |
| 17.85 | 4.97 | W |
| 20.15 | 4.40 | W |
| 21.54 | 4.12 | W |
| 24.34 | 3.65 | W |
| 26.44 | 3.37 | W |
| 28.26 | 3.16 | VS |
| 31.81 | 2.81 | M |
| 33.92 | 2.64 | W |
| 35.54 | 2.52 | VS |

In another preferred embodiment, the X-ray powder diffraction pattern of the crystal form H-1 is substantially characterized as in FIG. 18.

In another preferred embodiment, the molar ratio of citric acid to the compound of formula X in the crystal form H-1 is 1: (0.9-2.1), preferably 1: (1.1-2.1).

In another preferred embodiment, the polymorph is a form H-2 crystal of the citrate of the compound of formula X, i.e., crystal form H-2, which has an X-ray powder diffraction pattern including diffraction angle 2θ(°) values of the following group H1': 17.75±0.10, 20.15±0.10, 22.25±0.10, 26.28±0.10, and 30.04±0.10.

In another preferred embodiment, the X-ray powder diffraction pattern of the crystal form H-2 further includes two or more diffraction angle 2θ(°) values selected from the following group H2': 10.36±0.10, 22.75±0.10, 23.15±0.10, and 24.01±0.10.

In another preferred embodiment, the X-ray powder diffraction pattern of the crystal form H-2 further includes two or more diffraction angle 2θ(°) values selected from the following group H3': 21.65±0.10, 25.34±0.10, 27.00±0.10, 27.99±0.10, 34.09±0.10, 34.51±0.10, and 35.01±0.10.

In another preferred embodiment, the X-ray powder diffraction pattern of the crystal form H-2 includes six or more or all (such as 6, 7, 8, 9, 10, 11, 12, 13, 14, 15, 16, etc.) 2θ(°) values selected from the group H1', H2', and H3'.

In another preferred embodiment, the X-ray powder diffraction pattern of the crystal form H-2 has the 2θ(°) values shown in Table H-2 below:

TABLE H-2

| 2θ(°) | d value [Å] | relative intensity [%] |
|---|---|---|
| 7.22 | 12.24 | W |
| 10.36 | 8.53 | M |
| 13.29 | 6.66 | W |
| 16.32 | 5.43 | W |
| 19.17 | 4.63 | W |
| 20.84 | 4.26 | W |
| 21.65 | 4.10 | M |
| 22.75 | 3.91 | M |
| 24.01 | 3.70 | M |
| 25.34 | 3.51 | M |
| 27.00 | 3.30 | M |
| 28.32 | 3.15 | W |
| 30.04 | 2.97 | S |
| 32.93 | 2.72 | W |
| 34.51 | 2.60 | M |
| 36.01 | 2.49 | W |
| 37.97 | 2.37 | W |
| 8.13 | 10.87 | W |
| 11.67 | 7.58 | W |
| 15.63 | 5.66 | W |
| 17.75 | 4.99 | VS |
| 20.15 | 4.40 | S |
| 21.38 | 4.15 | W |
| 22.25 | 3.99 | VS |
| 23.15 | 3.84 | M |
| 24.54 | 3.63 | W |
| 26.28 | 3.39 | S |
| 27.99 | 3.18 | M |
| 29.05 | 3.07 | W |
| 31.48 | 2.84 | W |
| 34.09 | 2.63 | M |
| 35.01 | 2.56 | M |
| 37.40 | 2.40 | W |
| 38.70 | 2.32 | W |

In another preferred embodiment, the X-ray powder diffraction pattern of the crystal form H-2 is substantially characterized as in FIG. 19.

In another preferred embodiment, the molar ratio of citric acid to the compound of formula X in the crystal form H-2 is 1: (0.9-2.1), preferably 1: (1.1-2.1).

In another preferred embodiment, the polymorph is a form H-3 crystal of the citrate of the compound of formula X, i.e., crystal form H-3, which has an X-ray powder diffraction pattern including diffraction angle 2θ(°) values of the following group H1": 15.62±0.10, 19.67±0.10, 20.01±0.10, 23.01±0.10, 26.82±0.10, and 27.65±0.10.

In another preferred embodiment, the X-ray powder diffraction pattern of the crystal form H-3 further includes two or more diffraction angle 2θ(°) values selected from the following group H2": 16.29±0.10, 17.15±0.10, 18.11±0.10, 19.13±0.10, and 28.48±0.10.

In another preferred embodiment, the X-ray powder diffraction pattern of the crystal form H-3 further includes two or more diffraction angle 2θ(°) values selected from the following group H3": 21.44±0.10, 24.50±0.10, 29.10±0.10, and 30.20±0.10.

In another preferred embodiment, the X-ray powder diffraction pattern of the crystal form H-3 includes six or more or all (such as 6, 7, 8, 9, 10, 11, 12, 13, 14, 15, etc.) 2θ(°) values selected from the group H1", H2", and H3".

In another preferred embodiment, the X-ray powder diffraction pattern of the crystal form H-3 has the 2θ(°) values shown in Table H-3 below:

TABLE H-3

| 2θ(°) | d value [Å] | relative intensity [%] |
|---|---|---|
| 5.96 | 14.82 | W |
| 6.73 | 13.13 | W |
| 10.66 | 8.29 | W |
| 13.85 | 6.39 | W |
| 15.13 | 5.85 | W |
| 16.29 | 5.44 | M |
| 18.11 | 4.90 | M |

TABLE H-3-continued

| 2θ(°) | d value [Å] | relative intensity [%] |
|---|---|---|
| 19.67 | 4.51 | S |
| 21.44 | 4.14 | M |
| 22.64 | 3.92 | W |
| 23.49 | 3.78 | W |
| 24.50 | 3.63 | M |
| 25.91 | 3.44 | W |
| 27.65 | 3.22 | S |
| 29.10 | 3.07 | M |
| 31.02 | 2.88 | W |
| 32.13 | 2.78 | W |
| 33.92 | 2.64 | W |
| 36.02 | 2.49 | W |
| 38.67 | 2.33 | W |
| 6.46 | 13.67 | W |
| 8.34 | 10.59 | W |
| 11.88 | 7.44 | W |
| 14.47 | 6.12 | W |
| 15.62 | 5.67 | S |
| 17.15 | 5.17 | M |
| 19.13 | 4.63 | M |
| 20.01 | 4.43 | VS |
| 21.81 | 4.07 | W |
| 23.01 | 3.86 | S |
| 23.78 | 3.74 | W |
| 25.44 | 3.50 | W |
| 26.82 | 3.32 | S |
| 28.48 | 3.13 | M |
| 30.20 | 2.96 | M |
| 31.66 | 2.82 | W |
| 32.96 | 2.72 | W |
| 34.78 | 2.58 | W |
| 37.36 | 2.40 | W |

In another preferred embodiment, the X-ray powder diffraction pattern of the crystal form H-3 is substantially characterized as in FIG. 20.

In another preferred embodiment, the molar ratio of citric acid to the compound of formula X in the crystal form H-3 is 1: (0.9-2.1), preferably 1: (1.1-2.1).

In another preferred embodiment, the polymorph is a form J crystal of the hydrobromide of the compound of formula X, i.e., crystal form J, which has an X-ray powder diffraction pattern including diffraction angle 2θ(°) values of the following group J1: 20.71±0.10, 22.07±0.10, 22.84±0.10, 24.13±0.10, 25.00±0.10, 26.85±0.10, 28.26±0.10, and 31.38±0.10.

In another preferred embodiment, the X-ray powder diffraction pattern of the crystal form J further includes two or more diffraction angle 2θ(°) values selected from the following group J2: 8.85±0.10, 16.90±0.10, 17.65±0.10, 18.60±0.10, and 30.95±0.10.

In another preferred embodiment, the X-ray powder diffraction pattern of the crystal form J further includes two or more diffraction angle 2θ(°) values selected from the following group J3: 19.65±0.10, 25.59±0.10, 27.95±0.10, 29.13±0.10, and 34.77±0.10.

In another preferred embodiment, the X-ray powder diffraction pattern of the crystal form J includes six or more or all (such as 6, 7, 8, 9, 10, 11, 12, 13, 14, 15, 16, 17, 18, etc.) 2θ(°) values selected from the group J1, J2, and J3.

In another preferred embodiment, the X-ray powder diffraction pattern of the crystal form J-1 has the 2θ(°) values shown in Table J-1 below:

TABLE J-1

| 2θ(°) | d value [Å] | relative intensity [%] |
|---|---|---|
| 8.85 | 9.99 | M |
| 11.41 | 7.75 | W |
| 13.86 | 6.39 | W |
| 14.55 | 6.08 | W |
| 16.90 | 5.24 | M |
| 18.60 | 4.77 | M |
| 20.71 | 4.29 | S |
| 22.07 | 4.03 | VS |
| 24.13 | 3.69 | S |
| 25.59 | 3.48 | M |
| 26.85 | 3.32 | S |
| 28.26 | 3.16 | S |
| 30.16 | 2.96 | W |
| 31.38 | 2.85 | M |
| 34.77 | 2.58 | M |
| 36.57 | 2.46 | W |
| 37.63 | 2.39 | W |
| 39.42 | 2.28 | W |
| 11.00 | 8.04 | W |
| 12.49 | 7.08 | W |
| 14.27 | 6.20 | W |
| 15.60 | 5.68 | W |
| 17.65 | 5.02 | M |
| 19.65 | 4.51 | M |
| 21.36 | 4.16 | W |
| 22.84 | 3.89 | S |
| 25.00 | 3.56 | S |
| 26.54 | 3.36 | W |
| 27.95 | 3.19 | M |
| 29.13 | 3.06 | M |
| 30.95 | 2.89 | M |
| 33.30 | 2.69 | W |
| 35.75 | 2.51 | W |
| 37.32 | 2.41 | W |
| 39.04 | 2.31 | W |

In another preferred embodiment, the X-ray powder diffraction pattern of the crystal form J is substantially characterized as in FIG. 21.

In another preferred embodiment, the molar ratio of hydrobromic acid to the compound of formula X in the crystal form J is (0.8-1.2): 1, preferably (0.9-1.1): 1.

In another preferred embodiment, the polymorph is a form I crystal of a free base of the compound of formula X, i.e., crystal form I, which has an X-ray powder diffraction pattern including diffraction angle 2θ(°) values of the following group I1: 12.37±0.10, 14.99±0.10, 16.11±0.10, 21.03±0.10, 22.65±0.10, and 24.30±0.10.

In another preferred embodiment, the X-ray powder diffraction pattern of the crystal form I further includes two or more diffraction angle 2θ(°) values selected from the following group I2: 17.77±0.10, 18.59±0.10, 19.50±0.10, 21.50±0.10, 23.35±0.10, 25.30±0.10, 27.97±0.10, 29.73±0.10, and 31.81±0.10.

In another preferred embodiment, the X-ray powder diffraction pattern of the crystal form I further includes two or more diffraction angle 2θ(°) values selected from the following group I3: 10.36±0.10, 25.03±0.10, and 26.00±0.10.

In another preferred embodiment, the X-ray powder diffraction pattern of the crystal form I includes six or more or all (such as 6, 7, 8, 9, 10, 11, 12, 13, 14, 15, 16, 17, 18, etc.) 2θ(°) values selected from the group I1, I2, and I3.

In another preferred embodiment, the X-ray powder diffraction pattern of the crystal form I has the 2θ(°) values shown in Table I-1 below:

TABLE I-1

| 2θ(°) | d value [Å] | relative intensity [%] |
|---|---|---|
| 6.40 | 13.79 | W |
| 7.63 | 11.57 | W |
| 12.37 | 7.15 | S |
| 14.43 | 6.13 | W |
| 16.11 | 5.50 | VS |
| 18.59 | 4.77 | S |
| 21.03 | 4.22 | VS |
| 22.65 | 3.92 | S |
| 24.30 | 3.66 | VS |
| 25.30 | 3.52 | M |
| 26.43 | 3.37 | W |
| 27.97 | 3.19 | M |
| 30.35 | 2.94 | W |
| 31.81 | 2.81 | M |
| 34.41 | 2.60 | W |
| 35.54 | 2.52 | W |
| 37.02 | 2.43 | W |
| 37.99 | 2.37 | W |
| 6.94 | 12.73 | W |
| 10.36 | 8.53 | M |
| 13.97 | 6.34 | W |
| 14.99 | 5.90 | S |
| 17.77 | 4.99 | M |
| 19.50 | 4.55 | M |
| 21.50 | 4.13 | S |
| 23.35 | 3.81 | M |
| 25.03 | 3.55 | M |
| 26.00 | 3.42 | M |
| 26.92 | 3.31 | W |
| 29.73 | 3.00 | M |
| 30.80 | 2.90 | W |
| 34.05 | 2.63 | W |
| 34.66 | 2.59 | W |
| 36.33 | 2.47 | W |
| 37.64 | 2.39 | W |
| 39.25 | 2.29 | W |

In another preferred embodiment, the X-ray powder diffraction pattern of the crystal form I is substantially characterized as in FIG. 22.

In another preferred embodiment, the crystal form I further has one or more features selected from the group consisting of:

(i) differential scanning calorimetry analysis spectrum is substantially characterized as in FIG. 23A;

(ii) thermogravimetric analysis spectrum is substantially characterized as in FIG. 23A; and (iii) the crystal form I has a melting point of 165° C. to 175° C., preferably 167° C. to 173° C.

In another preferred embodiment, the polymorph is a form II crystal of a free base of the compound of formula X, i.e., crystal form II, which has an X-ray powder diffraction pattern including diffraction angle 2θ(°) values of the following group II1: 15.34±0.10, 16.57±0.10, 16.86±0.10, 17.33±0.10, 22.68±0.10, 24.36±0.10, 24.95±0.10, 25.51±0.10, and 26.53±0.10.

In another preferred embodiment, the X-ray powder diffraction pattern of the crystal form II further includes two or more diffraction angle 2θ(°) values selected from the following group II2: 18.13±0.10, 18.41±0.10, 19.21±0.10, 20.38±0.10, 21.24±0.10, and 23.45±0.10.

In another preferred embodiment, the X-ray powder diffraction pattern of the crystal form II further includes two or more diffraction angle 2θ(°) values selected from the following group II3: 11.00±0.10, 11.77±0.10, 22.13±0.10, 25.97±0.10, 28.95±0.10, 30.25±0.10, 30.97±0.10, and 32.43±0.10.

In another preferred embodiment, the X-ray powder diffraction pattern of the crystal form II includes six or more or all (such as 6, 7, 8, 9, 10, 11, 12, 13, 14, 15, 16, 17, 18, 19, 20, 21, 22, 23, etc.) 2θ(°) values selected from the group II1, II2, and II3.

In another preferred embodiment, the X-ray powder diffraction pattern of the crystal form II has the 2θ(°) values shown in Table II-1 below:

TABLE II-1

| 2θ(°) | d value [Å] | relative intensity [%] |
|---|---|---|
| 4.54 | 19.47 | W |
| 9.44 | 9.37 | W |
| 11.00 | 8.04 | M |
| 13.53 | 6.54 | W |
| 16.57 | 5.35 | VS |
| 17.33 | 5.11 | VS |
| 18.41 | 4.82 | S |
| 20.38 | 4.35 | S |
| 22.13 | 4.01 | M |
| 23.45 | 3.79 | M |
| 24.95 | 3.57 | VS |
| 25.97 | 3.43 | M |
| 27.74 | 3.21 | W |
| 28.95 | 3.08 | M |
| 30.97 | 2.89 | M |
| 34.01 | 2.63 | M |
| 35.43 | 2.53 | W |
| 37.18 | 2.42 | M |
| 38.99 | 2.31 | M |
| 6.51 | 13.58 | W |
| 10.60 | 8.34 | W |
| 11.77 | 7.51 | M |
| 15.34 | 5.77 | S |
| 16.86 | 5.26 | S |
| 18.13 | 4.89 | S |
| 19.21 | 4.62 | S |
| 21.24 | 4.18 | S |
| 22.68 | 3.92 | S |
| 24.36 | 3.65 | VS |
| 25.51 | 3.49 | S |
| 26.53 | 3.36 | VS |
| 28.31 | 3.15 | W |
| 30.25 | 2.95 | M |
| 32.43 | 2.76 | M |
| 34.90 | 2.57 | W |
| 36.05 | 2.49 | W |
| 37.58 | 2.39 | W |

In another preferred embodiment, the X-ray powder diffraction pattern of the crystal form II is substantially characterized as in FIG. 24.

In another preferred embodiment, the crystal form II further has one or more features selected from the group consisting of:

(i) differential scanning calorimetry analysis spectrum is substantially characterized as in FIG. 25A;

(ii) thermogravimetric analysis spectrum is substantially characterized as in FIG. 25A; and (iii) the crystal form II has a melting point of 169° C. to 179° C., preferably 171° C. to 177° C.

According to a second aspect of the present disclosure, a method of preparing the compound of formula X, or the pharmaceutically acceptable salt, or the polymorph thereof of the first aspect of the present disclosure is provided, and the method includes the steps of:

(1) reacting a compound X-e with a compound X-f in an inert solvent to form the compound of formula X;

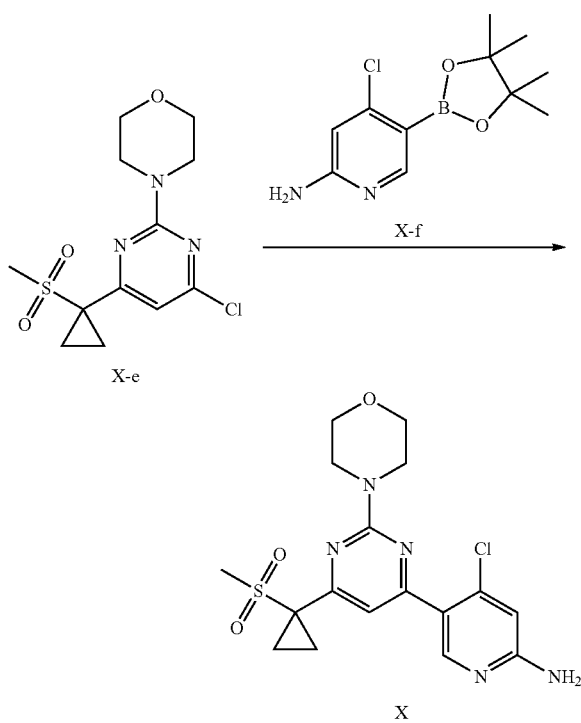

(2) optionally performing a salt forming reaction to the compound of formula X with an acid, thereby forming the pharmaceutically acceptable salt of the compound of formula X; and (3) optionally crystallizing the compound of formula X formed in step (1) or the pharmaceutically acceptable salt of the compound of formula X formed in step (2), thereby obtaining a polymorph of the compound of formula X or a polymorph of the pharmaceutically acceptable salt of the compound of formula X.

In another preferred embodiment, the method includes any one of the following sub-methods (A)-(O):

(A) the polymorph is the form A crystal of the hydrochloride of the compound of formula X, i.e., crystal form A, and the step (3) includes crystallization process of the compound of formula X in an organic solvent in the presence of hydrochloric acid, thereby forming the crystal form A.

In another preferred embodiment, in the sub-method (A), the organic solvent is selected from the group consisting of methanol, ethyl acetate, acetone, acetonitrile, and mixtures thereof. Preferably, the organic solvent is acetone.

In another preferred embodiment, in the sub-method (A), a molar ratio of hydrochloric acid to the compound of formula X is (0.8-1.2): 1, preferably (0.9-1.1): 1.

In another preferred embodiment, in the sub-method (A), the crystallization process is slow cooling, slow evaporation, suspension stirring, anti-solvent addition or a combination thereof, preferably slow cooling or suspension stirring.

In another preferred embodiment, in the sub-method (A), the temperature of the crystallization process is 0° C. to 50° C., preferably 0° C. to 20° C.

In another preferred embodiment, in the sub-method (A), the time of the crystallization process is 1 to 72 hours, preferably 2 to 50 hours.

(B) the polymorph is the form B-1 crystal of the sulfate of the compound of formula X, i.e., crystal form B-1, and the step (3) includes crystallization process of the compound of formula X in an organic solvent in the presence of sulfuric acid, thereby forming the crystal form B-1.

In another preferred embodiment, in the sub-method (B), the organic solvent is selected from the group consisting of methanol, acetone, acetonitrile, and mixtures thereof. Preferably, the organic solvent is acetone.

In another preferred embodiment, in the sub-method (B), a molar ratio of sulfuric acid to the compound of formula X is (0.2-1.1): 1, and preferably (0.3-0.8): 1.

In another preferred embodiment, in the sub-method (B), the crystallization process is slow cooling, slow evaporation, suspension stirring, anti-solvent addition or a combination thereof, preferably slow cooling or suspension stirring.

In another preferred embodiment, in the sub-method (B), the temperature of the crystallization process is 0° C. to 50° C., preferably 0° C. to 20° C.

In another preferred embodiment, in the sub-method (B), the time of the crystallization process is 1 to 72 hours, preferably 2 to 50 hours.

(C) the polymorph is the form B-2 crystal of the sulfate of the compound of formula X, i.e., crystal form B-2, and the step (3) includes crystallization process of the compound of formula X in an organic solvent in the presence of sulfuric acid, thereby forming the crystal form B-2.

In another preferred embodiment, in the sub-method (C), the organic solvent is ethyl acetate.

In another preferred embodiment, in the sub-method (C), a molar ratio of sulfuric acid to the compound of formula X is (0.2-1.1): 1, and preferably (0.3-0.8): 1.

In another preferred embodiment, in the sub-method (C), the crystallization process is slow cooling, slow evaporation, suspension stirring, anti-solvent addition or a combination thereof, preferably slow cooling or suspension stirring.

In another preferred embodiment, in the sub-method (C), the temperature of the crystallization process is 0° C. to 50° C., preferably 0° C. to 20° C.

In another preferred embodiment, in the sub-method (C), the time of the crystallization process is 1 to 72 hours, preferably 2 to 50 hours.

(D) the polymorph is the form C crystal of the maleate of the compound of formula X, i.e., crystal form C, and the step (3) includes crystallization process of the compound of formula X in an organic solvent in the presence of maleic acid, thereby forming the crystal form C.

In another preferred embodiment, in the sub-method (D), the organic solvent is selected from the group consisting of methanol, ethyl acetate, acetone, acetonitrile, and mixtures thereof. Preferably, the organic solvent is acetone.

In another preferred embodiment, in the sub-method (D), a molar ratio of maleic acid to the compound of formula X is (0.7-1.3): 1, and preferably (0.8-1.1): 1.

In another preferred embodiment, in the sub-method (D), the crystallization process is slow cooling, slow evaporation, suspension stirring, anti-solvent addition or a combination thereof, preferably slow cooling or suspension stirring.

In another preferred embodiment, in the sub-method (D), the temperature of the crystallization process is 0° C. to 50° C., preferably 0° C. to 20° C.

In another preferred embodiment, in the sub-method (D), the time of the crystallization process is 1 to 72 hours, preferably 2 to 50 hours.

(E) the polymorph is the form D-1 crystal of the fumarate of the compound of formula X, i.e., crystal form D-1, and the step (3) includes crystallization process of the compound of formula X in an organic solvent in the presence of fumaric acid, thereby forming the crystal form D-1.

In another preferred embodiment, in the sub-method (E), the organic solvent is methanol or ethyl acetate. Preferably, the organic solvent is methanol.

In another preferred embodiment, in the sub-method (E), a molar ratio of fumaric acid to the compound of formula X is (0.2-1.1): 1, and preferably (0.3-0.8): 1.

In another preferred embodiment, in the sub-method (E), the crystallization process is slow cooling, slow evaporation, suspension stirring, anti-solvent addition or a combination thereof, preferably slow cooling or suspension stirring.

In another preferred embodiment, in the sub-method (E), the temperature of the crystallization process is 0° C. to 50° C., preferably 0° C. to 20° C.

In another preferred embodiment, in sub-method (E), the time of the crystallization process is 1 to 72 hours, preferably 2 to 50 hours.

(F) the polymorph is the form D-2 crystal of the fumarate of the compound of formula X, i.e., crystal form D-2, and the step (3) includes crystallization process of the compound of formula X in an organic solvent in the presence of fumaric acid, thereby forming the crystal form D-2.

In another preferred embodiment, in the sub-method (F), the organic solvent is acetonitrile or acetone. Preferably, the organic solvent is acetone.

In another preferred embodiment, in the sub-method (F), a molar ratio of fumaric acid to the compound of formula X is (0.2-1.1): 1, and preferably (0.3-0.8): 1.

In another preferred embodiment, in the sub-method (F), the crystallization process is slow cooling, slow evaporation, suspension stirring, anti-solvent addition or a combination thereof, preferably slow cooling or suspension stirring.

In another preferred embodiment, in the sub-method (F), the temperature of the crystallization process is 0° C. to 50° C., preferably 0° C. to 20° C.

In another preferred embodiment, in the sub-method (F), the time of the crystallization process is 1 to 72 hours, preferably 2 to 50 hours.

(G) the polymorph is the form E crystal of the methanesulfonate of the compound of formula X, i.e., crystal form E, and the step (3) includes crystallization process of the compound of formula X in an organic solvent in the presence of methanesulfonic acid, thereby forming the crystal form E.

In another preferred embodiment, in the sub-method (G), the organic solvent is selected from the group consisting of methanol, ethyl acetate, acetone, acetonitrile, and mixtures thereof. Preferably, the organic solvent is acetone.

In another preferred embodiment, in the sub-method (G), a molar ratio of methanesulfonic acid to the compound of formula X is (0.8-1.2): 1, and preferably (0.9-1.1): 1.

In another preferred embodiment, in the sub-method (G), the crystallization process is slow cooling, slow evaporation, suspension stirring, anti-solvent addition or a combination thereof, preferably slow cooling or suspension stirring.

In another preferred embodiment, in the sub-method (G), the temperature of the crystallization process is 0° C. to 50° C., preferably 0° C. to 20° C.

In another preferred embodiment, in the sub-method (G), the time of the crystallization process is 1 to 72 hours, preferably 2 to 50 hours.

(H) the polymorph is the form F crystal of the L-tartrate of the compound of formula X, i.e., crystal form F, and the step (3) includes crystallization process of the compound of formula X in an organic solvent in the presence of L-tartaric acid, thereby forming the crystal form F.

In another preferred embodiment, in the sub-method (H), the organic solvent is selected from the group consisting of methanol, ethyl acetate, acetone, acetonitrile, and mixtures thereof. Preferably, the organic solvent is acetone.

In another preferred embodiment, in the sub-method (H), a molar ratio of L-tartaric acid to the compound of formula X is (0.8-1.2): 1, and preferably (0.9-1.1): 1.

In another preferred embodiment, in the sub-method (H), the crystallization process is slow cooling, slow evaporation, suspension stirring, anti-solvent addition or a combination thereof, preferably slow cooling or suspension stirring.

In another preferred embodiment, in the sub-method (H), the temperature of the crystallization process is 0° C. to 50° C., preferably 0° C. to 20° C.

In another preferred embodiment, in the sub-method (H), the time of the crystallization process is 1 to 72 hours, preferably 2 to 50 hours.

(I) the polymorph is the form G-1 crystal of the phosphate of the compound of formula X, i.e., crystal form G-1, and the step (3) includes crystallization process of the compound of formula X in an organic solvent in the presence of phosphoric acid, thereby forming the crystal form G-1.

In another preferred embodiment, in the sub-method (I), the organic solvent is methanol.

In another preferred embodiment, in the sub-method (I), a molar ratio of phosphoric acid to the compound of formula X is 1: (0.9-2.1), and preferably 1: (1.1-2.1).

In another preferred embodiment, in the sub-method (I), the crystallization process is slow cooling, slow evaporation, suspension stirring, anti-solvent addition or a combination thereof, preferably slow cooling or suspension stirring.

In another preferred embodiment, in the sub-method (I), the temperature of the crystallization process is 0° C. to 50° C., preferably 0° C. to 20° C.

In another preferred embodiment, in the sub-method (I), the time of the crystallization process is 1 to 72 hours, preferably 2 to 50 hours.

(J) the polymorph is the form G-2 crystal of the phosphate of the compound of formula X, i.e., crystal form G-2, and the step (3) includes crystallization process of the compound of formula X in an organic solvent in the presence of phosphoric acid, thereby forming the crystal form G-2.

In another preferred embodiment, in the sub-method (J), the organic solvent is ethyl acetate.

In another preferred embodiment, in the sub-method (J), a molar ratio of phosphoric acid to the compound of formula X is 1: (0.9-2.1), and preferably 1: (1.1-2.1).

In another preferred embodiment, in the sub-method (J), the crystallization process is slow cooling, slow evaporation, suspension stirring, anti-solvent addition or a combination thereof, preferably slow cooling or suspension stirring.

In another preferred embodiment, in the sub-method (J), the temperature of the crystallization process is 0° C. to 50° C., preferably 0° C. to 20° C.

In another preferred embodiment, in the sub-method (J), the time of the crystallization process is 1 to 72 hours, preferably 2 to 50 hours.

(K) the polymorph is the form G-3 crystal of the phosphate of the compound of formula X, i.e., crystal form G-3, and the step (3) includes crystallization process of the compound of formula X in an organic solvent in the presence of phosphoric acid, thereby forming the crystal form G-3.

In another preferred embodiment, in the sub-method (K), the organic solvent is acetonitrile or acetone.

In another preferred embodiment, in the sub-method (K), a molar ratio of phosphoric acid to the compound of formula X is 1: (0.9-2.1), and preferably 1: (1.1-2.1).

In another preferred embodiment, in the sub-method (K), the crystallization process is slow cooling, slow evaporation, suspension stirring, anti-solvent addition or a combination thereof, preferably slow cooling or suspension stirring.

In another preferred embodiment, in the sub-method (K), the temperature of the crystallization process is 0° C. to 50° C., preferably 0° C. to 20° C.

In another preferred embodiment, in sub-method (K), the time of the crystallization process is 1 to 72 hours, preferably 2 to 50 hours.

(L) the polymorph is the form H-1 crystal of the citrate of the compound of formula X, i.e., crystal form H-1, and the step (3) includes crystallization process of the compound of formula X in an organic solvent in the presence of citric acid, thereby forming the crystal form H-1.

In another preferred embodiment, in the sub-method (L), the organic solvent is methanol.

In another preferred embodiment, in the sub-method (L), a molar ratio of citric acid to the compound of formula X is 1: (0.9-2.1), and preferably 1: (1.1-2.1).

In another preferred embodiment, in the sub-method (L), the crystallization process is slow cooling, slow evaporation, suspension stirring, anti-solvent addition or a combination thereof, preferably slow cooling or suspension stirring.

In another preferred embodiment, in the sub-method (L), the temperature of the crystallization process is 0° C. to 50° C., preferably 0° C. to 20° C.

In another preferred embodiment, in the sub-method (L), the time of the crystallization process is 1 to 72 hours, preferably 2 to 50 hours.

(M) the polymorph is the form H-2 crystal of the citrate of the compound of formula X, i.e., crystal form H-2, and the step (3) includes crystallization process of the compound of formula X in an organic solvent in the presence of citric acid, thereby forming the crystal form H-2.

In another preferred embodiment, in the sub-method (M), the organic solvent is ethyl acetate.

In another preferred embodiment, in the sub-method (M), a molar ratio of citric acid to the compound of formula X is 1: (0.9-2.1), and preferably 1: (1.1-2.1).

In another preferred embodiment, in the sub-method (M), the crystallization process is slow cooling, slow evaporation, suspension stirring, anti-solvent addition or a combination thereof, preferably slow cooling or suspension stirring.

In another preferred embodiment, in the sub-method (M), the temperature of the crystallization process is 0° C. to 50° C., preferably 0° C. to 20° C.

In another preferred embodiment, in the sub-method (M), the time of the crystallization process is 1 to 72 hours, preferably 2 to 50 hours.

(N) the polymorph is the form H-3 crystal of the citrate of the compound of formula X, i.e., crystal form H-3, and the step (3) includes crystallization process of the compound of formula X in an organic solvent in the presence of citric acid, thereby forming the crystal form H-3.

In another preferred embodiment, in the sub-method (N), the organic solvent is acetonitrile or acetone.

In another preferred embodiment, in the sub-method (N), a molar ratio of citric acid to the compound of formula X is 1: (0.9-2.1), and preferably 1: (1.1-2.1).

In another preferred embodiment, in the sub-method (N), the crystallization process is slow cooling, slow evaporation, suspension stirring, anti-solvent addition or a combination thereof, preferably slow cooling or suspension stirring.

In another preferred embodiment, in the sub-method (N), the temperature of the crystallization process is 0° C. to 50° C., preferably 0° C. to 20° C.

In another preferred embodiment, in the sub-method (N), the time of the crystallization process is 1 to 72 hours, and preferably 2 to 50 hours.

(O) the polymorph is the form J crystal of the hydrobromide of the compound of formula X, i.e., crystal form J, and the step (3) includes crystallization process of the compound of formula X in an organic solvent in the presence of hydrobromic acid, thereby forming the crystal form J.

In another preferred embodiment, in the sub-method (O), the organic solvent is ethyl acetate, acetonitrile or acetone.

In another preferred embodiment, in the sub-method (O), a molar ratio of hydrobromic acid to the compound of formula X is (0.8-1.2): 1, and preferably (0.9-1.1): 1.

In another preferred embodiment, in the sub-method (O), the crystallization process is slow cooling, slow evaporation, suspension stirring, anti-solvent addition or a combination thereof, preferably slow cooling or suspension stirring.

In another preferred embodiment, in the sub-method (O), the temperature of the crystallization process is 0° C. to 50° C., preferably 0° C. to 20° C.

In another preferred embodiment, in the sub-method (O), the time of the crystallization process is 1 to 72 hours, and preferably 2 to 50 hours.

(P) the polymorph is the form I crystal of the free base of the compound of formula X, i.e., crystal form I, and the step (3) includes crystallization process of the compound of formula X in an organic solvent, thereby forming the crystal form I.

In another preferred embodiment, in the sub-method (P), the organic solvent is methanol, ethyl acetate, acetonitrile, tetrahydrofuran, methyl tert-butyl ether, isopropanol or acetone.

In another preferred embodiment, in the sub-method (P), the crystallization process is slow cooling, slow evaporation, suspension stirring, anti-solvent addition or a combination thereof, preferably slow cooling, slow evaporation or suspension stirring.

(Q) the polymorph is the form II crystal of the free base of the compound of formula X, i.e., crystal form II, and the step (3) includes crystallization process of the compound of formula X in an organic solvent, thereby forming the crystal form II.

In another preferred embodiment, in the sub-method (Q), the organic solvent is methanol, ethanol, acetonitrile, ethyl acetate, methyl tert-butyl ether or isopropanol.

In another preferred embodiment, in the sub-method (Q), the crystallization process is slow cooling, slow evaporation, suspension stirring, anti-solvent addition or a combination thereof, preferably slow cooling or suspension stirring.

According to a third aspect of the present disclosure, a pharmaceutical composition is provided, which includes: (a) the compound of formula X, or the pharmaceutically acceptable salt, or the polymorph thereof of any one of the first aspect of the present disclosure; and (b) a pharmaceutically acceptable carrier.

According to a fourth aspect of the present disclosure, a use of the compound of formula X or the pharmaceutically acceptable salt, or the polymorph thereof of any one of the first aspect of the disclosure, or the pharmaceutical composition of the third aspect of the disclosure for the manufacture of a medicament for the treatment of protein tyrosine kinase-mediated diseases is provided.

Preferably, the protein tyrosine kinase-mediated disease is a PI3K kinase-mediated disease.

A fifth aspect of the present disclosure provides a use of the compound formula X, or the pharmaceutically acceptable salt, or the polymorph thereof of any one of the first aspect of the disclosure, or the pharmaceutical composition of the third aspect of the disclosure for the manufacture of a medicament for the treatment of cancer or tissue proliferative diseases.

Preferably, the cancer is selected from the group consisting of melanoma, papillary thyroid neoplasms, cholangiocarcinoma, colon cancer, ovarian cancer, endometrial cancer, cervical cancer, lung cancer, esophageal cancer, brain cancer, malignant lymphoma, liver cancer, stomach cancer, kidney cancer, bladder cancer, prostate cancer, breast cancer, pancreatic cancer or sarcoma, and primary or recurrent solid tumors of the skin, colon, thyroid, lung, and ovary, leukemia, head and neck cancer, glioma, and glioblastoma.

It should be understood that each of the above technical features of the invention and each technical feature specifically described below (such as in Examples) can be combined with each other within the scope of the present invention so as to constitute new or preferred technical solutions which need not be specified again herein.

DETAILED DESCRIPTION OF THE EMBODIMENTS

Figure 1:
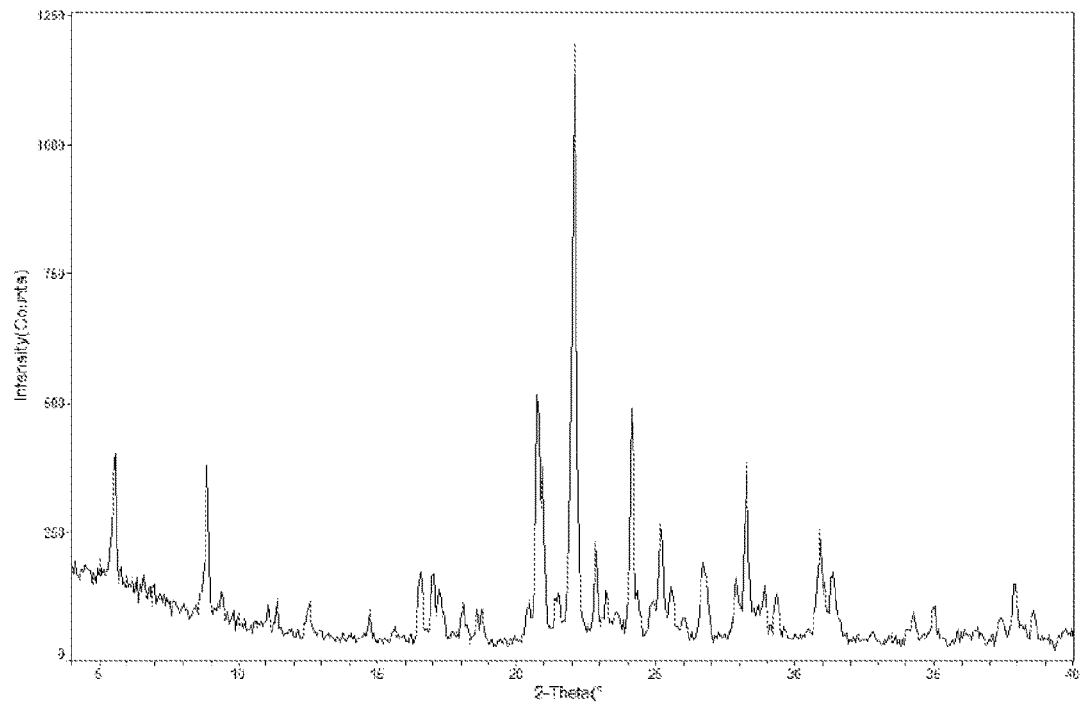
FIG. 1 shows an XRPD pattern of crystal form A.

Inventors discovered a series of polymorphs of free base, salts and polymorphs of the salts of the compound of formula X after a long and intensive study. The in vitro enzyme and cell growth inhibition experiments showed that the free base of the compound of formula X exhibited a strong inhibitory activity against PI3K kinase, not only exhibiting high inhibitory activity on PI3K and especially PI3K-α kinase on enzyme level, but also exhibiting high inhibitory effect on PIK3CA mutant breast cancer cell lines T47D and MCF-7, while at the same time showing low cytotoxicity. Moreover, this compound has relatively low cytotoxicity in normal cell lines (such as NIH-3T3 cells), thereby significantly reducing nonspecific side effects. The study also found that a series of the polymorphs of free base, salts and the polymorphs of the salts of the compound of formula X not only had good physical and chemical stability but also had good pharmacological activity in vivo and in vitro, and therefore could be further developed into drugs. On this basis, the present disclosure has been completed.

As used herein, the term "compound of the present disclosure" includes the compound of formula X of the present disclosure, a pharmaceutically acceptable salt of the compound of formula X of the present disclosure, and the polymorph of the present disclosure.

Compound of Formula X

In the present disclosure, "compound of formula X" or "compound represented by formula X" can be used interchangeably. Unless specified otherwise, the term generally refers to the free base form.

In the present disclosure, the compound of formula X is 4-chloro-5-(6-(1-(methylsulfonyl)cyclopropyl)-2-morpholinopyrimidin-4-yl)pyridin-2-amine, which has good selective inhibitory activity against PI3K, especially PI3K-α kinase and lower cytotoxicity, as well as favorable metabolic characteristics.

In the present disclosure, "free base sample" or "free base" refers to the free base of the compound of formula X prepared in Example 1.

Pharmaceutically Acceptable Salt of the Compound of Formula X

In the present disclosure, the pharmaceutically acceptable salts are preferably selected from the group consisting of hydrochloride, sulfate, phosphate, acetate, L-lactate, maleate, fumarate, succinate, L-malate, adipate, L-tartrate, hippurate, citrate, mucate, glycollate, D-glucuronate, benzoate, gentisate, nicotinate, ethanedisulphonate, oxalate, methanesulfonate, benzenesulfonate, 2-hydroxyethane sulfonate, and hydrobromide.

Polymorph

Solid exists either in an amorphous form or in a crystalline form. In the case of crystalline form, the molecules are positioned within the three-dimensional lattice sites. When a compound is crystallized from a solution or slurry, it can be crystallized in different space lattice arrangements (this property is called "polymorphism") to form crystals with different crystalline forms. Each of the various crystalline forms is called as "polymorph". Different polymorphs of a given substance may differ from each other in one or more physical properties (such as solubility and dissolution rate, true specific gravity, crystalline form, packing pattern, flowability and/or solid state stability).

Crystallization

The solubility limit of the interested compound can be exceeded by operating the solution, thereby accomplishing crystallization on a production scale. This can be done by a variety of methods, for example, slow cooling, by dissolving the compound at a relatively high temperature and then cooling the solution below a saturation limit. Alternatively, the volume of liquid can be reduced by boiling, atmospheric evaporating, vacuum drying, or by some other means. The solubility of the interested compound may be reduced by adding an anti-solvent or a solvent in which the compound has a low solubility or a mixture of such solvents. An alternative method is to adjust the pH to reduce the solubility. See Crystallization, Third Edition, J W MullFns, ButtFrworth-HFinFman Ltd., 1993, ISBN 0750611294 for a detailed description of crystallization.

The "suspension stirring" described in the present disclosure means a way to get crystals by mixing the compound of formula X with the corresponding acid or a solution of the corresponding acid to form a turbid solution, or by mixing the compound of formula X with a suitable solvent to form a turbid solution before stirring. Suitable solvents may be water or organic solvents.

The "slow volatilization" described in the present disclosure means a way to get crystals by placing a solution of the compound of formula X or a solution of the compound of formula X and the corresponding acid at a certain temperature for slow volatilization of the solvent.

The "addition of anti-solvent" described in the present disclosure means a method to get crystals by adding a suitable solvent to a solution of the compound of formula X and precipitating the crystals.

If salt formation and crystallization are expected to occur at the same time, the addition of an appropriate acid or base can result in the direct crystallization of the desired salt if the salt is less soluble in the reaction medium than the raw material. Likewise, in a medium in which the solubility of the desired final form is lower than that of reactant, the final product can be directly crystallized when the synthetic reaction is completed.

Optimization of crystallization can include inoculation of the crystal of desired form as a seed into the crystallization medium. In addition, many crystallization methods include a combination of the above strategies. One example is to dissolve the interested compound in a solvent at a high temperature, followed by the addition of an antisolvent with a suitable volume in a controlled manner so that the system is just below saturation level. At this moment, the seed of desired form (the integrity of the seed is kept) can be added and the system is cooled to complete the crystallization.

As used herein, the term "room temperature" generally means 4-30° C., preferably 20±5° C.

Polymorphs of the Present Disclosure

In the present disclosure, "crystal of the present disclosure", "crystal form of the present disclosure", "polymorph of the present disclosure" and the like can be used interchangeably.

In the present disclosure, "polymorph of the compound of formula X" and "polymorph of the free base of the compound of formula X" are used interchangeably.

As used herein, the term "polymorph of the present disclosure" includes polymorphs of the free base of the compound of formula X or polymorphs of pharmaceutically acceptable salts of the compound of formula X (e.g., hydrochloride, sulfate, hydrobromide, phosphate, methanesulfonate, maleate, L-tartrate, citrate, fumarate), or polymorphs of various solvates of the compound of formula X, and also include different polymorphs of the same salts (such as hydrochloride, sulfate, hydrobromide, phosphate, methanesulfonate, maleate, L-tartrate, citrate, fumarate) or solvates.

Preferred polymorphs of the present disclosure include (but not limited to): (i) crystal form A, crystal form B-1, crystal form B-2, crystal form C, crystal form D-1, crystal form D-2, crystal form E, crystal form F, crystal form G-1, crystal form G-2, crystal form G-3, crystal form H-1, crystal form H-2, crystal form H-3, crystal form J (crystal form of salt); and (ii) crystal form I and crystal form II (crystal form of the compound of formula X).

Identification and Properties of Polymorphs

Polymorphs of the compounds of formula X or the pharmaceutically acceptable salts can be characterized using known methods or instruments, for example, using a variety of methods and instruments as follows.

X-Ray Powder Diffraction

Methods of determining X-ray powder diffraction of the crystals are known in the art. For example, an X-ray powder diffractometer was used to obtain a pattern with a copper radiation target at a scanning speed of 2° per minute.

The polymorph of the compound of formula X of the present disclosure or a pharmaceutically acceptable salt thereof has a specific crystal form and has specific characteristic peaks in an X-ray powder diffraction (XRPD) pattern.

Differential Scanning Calorimetry

It is also called "differential scanning calorimetry analysis" (DSC), which is a technique that measures the relationship between energy difference of the measured substance and the reference substance and temperature during heating. The location, shape and number of peaks on the DSC pattern are related to the nature of the substance, and therefore can be used to qualitatively identify the substance. This method can be commonly used in the art to detect the phase transition temperature, glass transition temperature, reaction heat and other parameters of a substance.

Pharmaceutical Compositions of Compound of Formula X and their Use

Generally, the compound of formula X of the present disclosure or a pharmaceutically acceptable salt thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present disclosure contained in these formulations may be solid powders or granules; aqueous or non-aqueous liquid solutions or suspensions; water-in-oil or oil-in-water emulsions. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylene glycol and polyethylene glycol. The active compounds may form a solution or suspension with the above-mentioned carriers.

The compositions of the present disclosure are formulated, quantified and administered in a manner consistent with the practice of medicine. The "effective amount" of the administrated compound depends on the factors such as the specific disease to be treated, the individual being treated, the cause of diseases, the drug targets and the mode of administration, etc.

As used herein, "therapeutically effective amount" refers to the amount that yields a function or activity to humans and/or animals and may be tolerated by humans and/or animals.

The therapeutically effective amount of the compound of the present disclosure contained in the pharmaceutical composition or medicinal composition of the present disclosure is preferably 0.1 mg-5 g/kg (weight).

The compound or the pharmaceutical compositions of the present disclosure are useful for treating protein tyrosine kinase mediated diseases, or treating cancer or tissue proliferative diseases.

Preferably, the protein tyrosine kinase-mediated disease is a PI3K kinase-mediated disease.

Preferably, the cancer is selected from the group consisting of melanoma, papillary thyroid neoplasms, cholangiocarcinoma, colon cancer, ovarian cancer, endometrial cancer, cervical cancer, lung cancer, esophageal cancer, brain cancer, malignant lymphoma, liver cancer, stomach cancer, kidney cancer, bladder cancer, prostate cancer, breast cancer, pancreatic cancer or sarcoma, and primary or recurrent solid tumors of the skin, colon, thyroid, lung, and ovary, leukemia, head and neck cancer, glioma, and glioblastoma.

For certain diseases, the compound or the pharmaceutical composition of the present disclosure may be used in combination with other drugs in order to achieve the desired therapeutic effect.

The Main Advantages of the Present Disclosure Include:

The polymorph of the compound of formula X or a pharmaceutically acceptable salt thereof has an excellent physical and chemical stability and outstanding related pharmacological activity and is an ideal PI3K inhibitor.

The present disclosure will be further illustrated below with reference to the specific examples. It should be understood that these examples are only to illustrate the disclosure but not to limit the disclosure of the disclosure. The experimental methods without specific conditions in the following embodiments are generally carried out according to conventional conditions, or in accordance with the conditions recommended by the manufacturer. Unless indicated otherwise, parts and percentage are calculated by weight.

Reagents and Instruments

The structure and purity of the compounds are identified by nuclear magnetic resonance ($^1$HNMR) and/or LC-MS mass spectrometry (LC-MS) in the present disclosure. $^1$HNMR: BrukerAVANCF-400 NMR machine, the internal standard was tetramethylsilane (TMS). LC-MS: Agilent 1200 HPLC System/6140 MS liquid-mass spectrometer (available from Agilent), column WatersX-Bridge, 150×4.6 mm, 3.5 μm. Preparative high performance liquid chromatography (pre-HPLC): Waters PHW007, column XBridge C18, 4.6*150 mm, 3.5 um.

ISCO Combiflash-Rf75 or Rf200 automatic eluting column instrument, Agela 4 g, 12 g, 20 g, 40 g, 80 g, 120 g disposable silica gel column.

The known starting materials of the disclosure may be synthesized by using the methods known in the art, or may be purchased from ABCR GmbH & Co. KG, Acros Organics, Aldrich Chemical Company, Accela ChemBio Inc and Darui Chemical Company etc.

All examples were performed under nitrogen or argon atmosphere and the solution refers to the aqueous solution if without special explanation.

As used herein, DMF refers to dimethylformamide, DMSO refers to dimethylsulfoxide, THF refers to tetrahydrofuran, DIEA refers to N, N-diisopropylethylamine, EA refers to ethyl acetate, PE refers to petroleum ether, BINAP refers to (2R,3S)-2,2'-bis diphenylphosphino-1,1'-binaphthyl, NBS refers to N-bromosuccinimide, NCS refers to N-chlorosuccinimide, $Pd_2(dba)_3$ refers to tris(dibenzylideneacetone)dipalladium, and $Pd(dppf)Cl_2$ refers to [1,1'-bis(diphenylphosphino) ferrocene] palladium dichloride.

General Method

The powder X-ray diffraction patterns are obtained using a D8 ADVANCE X-ray powder diffraction analyzer through methods known in the art. XRPD test parameters are shown in the following table.

| Parameter | XRPD |
| --- | --- |
| X-ray source | Cu K ($\lambda$ = 1.54056 Angstrom) |
| tube settings | 40 kV, 40 mA |
| Detector | PSD |
| Scanning range (°2θ(°)) | 4°~40° |
| Scanning step (°2θ(°)) | 0.05 |
| Scan rate | 1 second/step |

In the pattern, the site of each peak was determined by 2θ(°). It should be understood that different instruments and/or conditions could result in slightly different data and changes in peak site and relative intensity. The division of the intensity of peaks only reflects the approximate size of peaks in each site. In the present disclosure, the highest diffraction peak of each crystal form was taken as the base peak, which was defined as $I_0$ with the relative intensity as 100%, and other peaks had the ratio of their peak height to the peak height of base peak as the relative intensity $I/I_0$. The definition of the relative intensity of each peak was shown in the following table:

| Relative intensity $I/I_0$(%) | Definition |
| --- | --- |
| 50~100 | VS (very strong) |
| 20~50 | S (strong) |
| 10~20 | M (medium) |
| 0~10 | W (weak) |

The acid-base molar ratio of the salts of the present disclosure or their crystal forms was determined by HPLC/IC or $^1$H NMR.

The liquid nuclear magnetic spectrum was collected on a Bruker 400M NMR spectrometer with DMSO-$d_6$ as the solvent.

High performance liquid chromatography spectrum was acquired on an Agilent 1260 HPLC, the specific instrument and test parameters are shown in the table below.

| Column | ExtendC18, 150*4.6 mm, 5 μm, PN773450-902 | |
| --- | --- | --- |
| Mobile phase | A: 0.1% aqueous solution of trifluoroacetic acid | |
| | B: 0.1% trifluoroacetic acid in acetonitrile | B: acetonitrile |

-continued

| Gradient | Time (min) | B (%) | Time (min) | B (%) |
|---|---|---|---|---|
| | 0.0 | 5 | 0.0 | 5 |
| | 1.0 | 5 | 0.5 | 5 |
| | 13 | 95 | 8 | 95 |
| | 14 | 95 | 13 | 95 |
| | 14.1 | 5 | 13.1 | 5 |
| | 15 | 5 | 15 | 5 |
| Operation times | 15 minutes | | 15 minutes | |
| Post-running time | 0 minute | | 0 minute | |
| Velocity | 1.0 ml/min | | 0.8 ml/min | |
| Sample volume | 5 μL | | 5 μL | |
| Detection wavelength | DAD(254 nm) | | DAD(250 nm) | |
| Column temperature | 25° C. | | 25° C. | |
| Diluent | DMSO | | 40% acetonitrile solution | |

TGA and DSC pattern were acquired on a TGA Q500 V20.10 Build 36 thermogravimetric analyzer and a DSC Q2000 V24.4 Build 116 differential scanning calorimeter respectively, test parameters are shown in the following table.

| Parameter | TGA | DSC |
|---|---|---|
| Method | Linear warming | Linear warming |
| Sample tray | Platinum plate, open | Aluminum plate, gland |
| Temperature range | 25° C. - set temperature | 25° C. - set temperature |
| Scanning rate (° C./min) | 10 | 10 |
| Protective gas | Nitrogen | Nitrogen |

The Dynamic Vapor Sorption (DVS) curve was acquired on the DVS Intrinsic of Surface Measurement Systems. The DVS test parameters are listed in the table below.

| Parameters | Setting value |
|---|---|
| Temperature | 25° C. |
| Sample size | 10~20 mg |
| Protect gas | $N_2$, 0.1 MPa |
| dm/dt | 0.01%/min |
| Minimum dm/dt balance time | 5 minutes |
| The maximum balance time | 120 minutes |
| RH range | 0% RH~95% RH |
| RH gradient | 5% RH |

It should be understood that, different values may be obtained when other types of instruments with the same function as the instruments described above or test conditions which are different from the conditions used in the present disclosure were used. Therefore, the recited value should not be considered as an absolute numerical value.

Due to the instrumental errors or different operators, one skilled in the art will understand that the above parameters used to characterize the physical properties of crystals may differ slightly, so the parameters described above are only used to assist in characterizing the polymorphs provided herein, and can not be regarded as a limitation on the polymorphs of the present disclosure.

Comparative Example 1-3 (Prepared by the Method Disclosed in PCT/CN2015/097739)

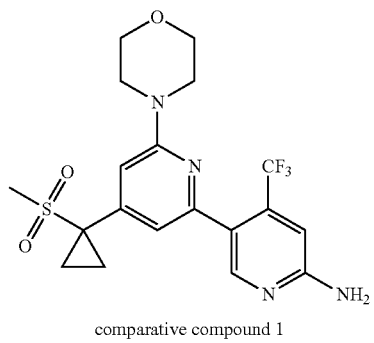

comparative compound 1

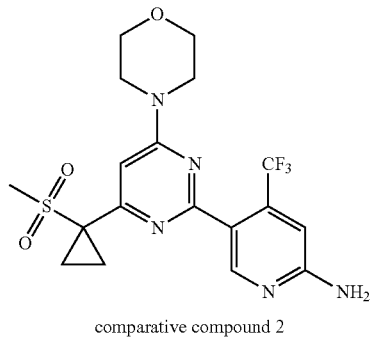

comparative compound 2

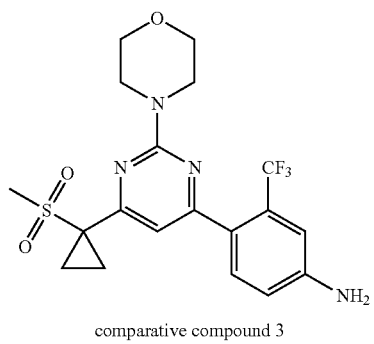

comparative compound 3

Preparation Method of Compound X-f:

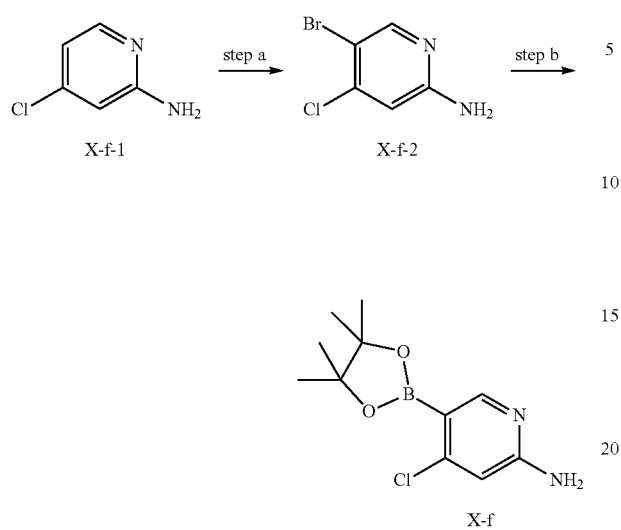

Step a: Compound N-bromosuccinimide (1.56 g, 8.76 mmol) was added to a solution of compound X-f-1 (1.0 g, 7.75 mmol) in chloroform (100 ml), and the mixture was stirred at ambient temperature for 2 hours. After the reaction was completed, the mixture was concentrated under reduced pressure and extracted with dichloromethane. The organic phase was separated and concentrated under reduced pressure to obtain the crude product, which was purified by Combi-flash column chromatography to obtain compound X-f-2 (1.2 g), purity 84%, MS m/z (ESI): 207[M+H]+.

Step b: Compound X-f-2 (1.2 g, 5.83 mmol), bis(pinacolato)diboron (1.63 g, 6.41 mmol), potassium acetate (1.71 g, 17.48 mmol), and Pd(dppf)Cl$_2$ ([1,1'-bis(diphenylphosphino)ferrocene]palladium dichloride) (212 mg, 0.29 mmol) were added to a solution of 1,4-dioxane (50 ml), and the mixture was stirred at 115° C. under microwave overnight. After the reaction was completed, the mixture was cooled to room temperature, filtered, and extracted with water and ethyl acetate. The organic phase was separated, concentrated under reduced pressure to obtain a crude product, which was purified by Combi-flash column chromatography to obtain compound X-f (100 mg), purity 82%, MS m/z (ESI): 255 [M+H]+.

Example 1 Preparation of the Compound of Formula X

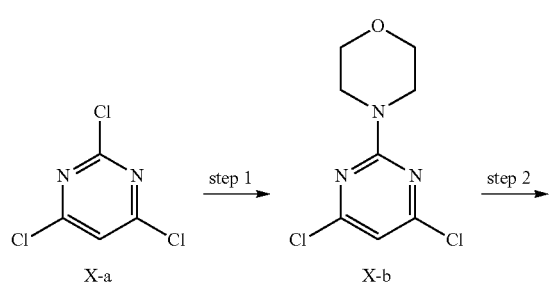

Step 1:

A solution of compound X-a (5.0 g, 27.5 mmol) and triethylamine (3.0 g, 30 mmol) in 25 ml of dichloromethane was added dropwise to a solution of morpholine (2.4 g, 27.5 mmol) in 5 ml of dichloromethane at a temperature of 5° C. to 15° C., stirred at ambient temperature for 2 hours. The reaction was completed and the mixture was extracted with dichloromethane. The organic phases were separated and combined, and concentrated under reduced pressure to obtain the crude product, which was purified by Combi-flash column chromatography to give compound X-b (1.4 g). Purity: 95%, MS m/z (ESI): 234[M+H]+.

Step 2:

A mixture of compound X-b (1.4 g, 6 mmol), methyl 2-(methylsulfonyl) acetate (1.0 g, 6.6 mmol), sodium hydride (500 mg, 12 mmol), and dimethylsulfoxide (30 mL) was added to a sealed tube, stirred at 120° C. under microwave for 15 minutes. After the reaction was completed, the mixture was cooled to ambient temperature and extracted with ethyl acetate. The organic phases were separated and combined, and concentrated under reduced pressure to obtain the crude product, which was purified by Combi-flash column chromatography to give compound X-c (500 mg). Purity: 95%, MS m/z (ESI): 350[M+H]$^+$.

Step 3:

Compound X-c (500 mg, 1.4 mmol) and sodium hydroxide (170 mg, 4.3 mmol) were added to methanol/water (10 ml/2.5 ml), stirred at 60° C. for 1 hour. After the reaction was completed, the mixture was cooled to ambient temperature, extracted with ethyl acetate, washed with water, and the organic phase was separated and concentrated under reduced pressure to give crude compound X-d (500 mg). MS m/z (ESI): 292 [M+H]$^+$.

Step 4:

1,2-dibromoethane (1.3 g, 7 mmol) and sodium hydride (300 mg, 7 mmol) were added to a solution of compound X-d (500 mg, 1.7 mmol) in 15 ml of dimethylformamide, stirred at ambient temperature for 1 hour. The reaction was completed, and water and ethyl acetate were added for extraction. The organic phases were separated and combined, dried over anhydrous sodium sulfate, and filtered. The filtrate was concentrated under reduced pressure to obtain crude compound X-e (48 mg). MS m/z (ESI): 318[M+H]$^+$.

Step 5:

A mixture of compound X-e (50 mg, 0.157 mmol), compound X-f (120 mg, 0.47 mmol), Pd(dppf)Cl$_2$ ([1,1'-bis(diphenylphosphino)ferrocene]dichloropalladium) (11.52 mg (0.016 mmol), sodium carbonate (24 mg, 0.314 mmol), and acetonitrile/water (5 ml/1 ml) was added to a sealed tube and stirred at 120° C. under microwaves for 10 minutes. After the reaction was completed, the mixture was cooled to ambient temperature, filtered, and water and ethyl acetate were added for extraction. The organic phase was separated, dried over anhydrous sodium sulfate. The organic phase was separated and concentrated under reduced pressure to obtain a crude product, which was isolated and purified by a preparative liquid phase to obtain compound X (7.06 mg), purity 98.25%. MS m/z (ESI): 410[M+H]+. $^1$H NMR (500 MHz, CDCl$_3$) δ 8.40 (s, 1H), 7.31 (s, 1H), 6.58 (s, 1H), 4.69 (brs, 2H), 3.88-3.81 (m, 4H), 3.80-3.76 (m, 4H), 3.09 (s, 3H), 1.86 (q, J=4.5 Hz, 2H), 1.54-1.49 (m, 2H).

Example 2 Preparation of Crystal Form I of the Free Base of the Compound of Formula X Five slow evaporation tests were performed using different solvent systems. About 10 mg of the compound of formula X prepared in Example 1 was weighed into a glass vial respectively, and an appropriate amount of solvent in the following table was added to obtain a nearly saturated solution. After shaking and filtration, 200 μL of the corresponding solvent was added to the clear solution, and the solution was slowly evaporated at ambient temperature. After the solvent was completely evaporated to dryness, the resulting solid was collected and subjected to XRPD test. The results were shown in the following table, and the crystal form I was obtained in the slow evaporation test.

| Solvent | Crystal form | Solvent | crystal form |
|---|---|---|---|
| methanol | crystal form I | ethyl acetate | crystal form I |
| acetonitrile | crystal form I | acetone | crystal form I |
| tetrahydrofuran | crystal form I | | |

Figure 22:
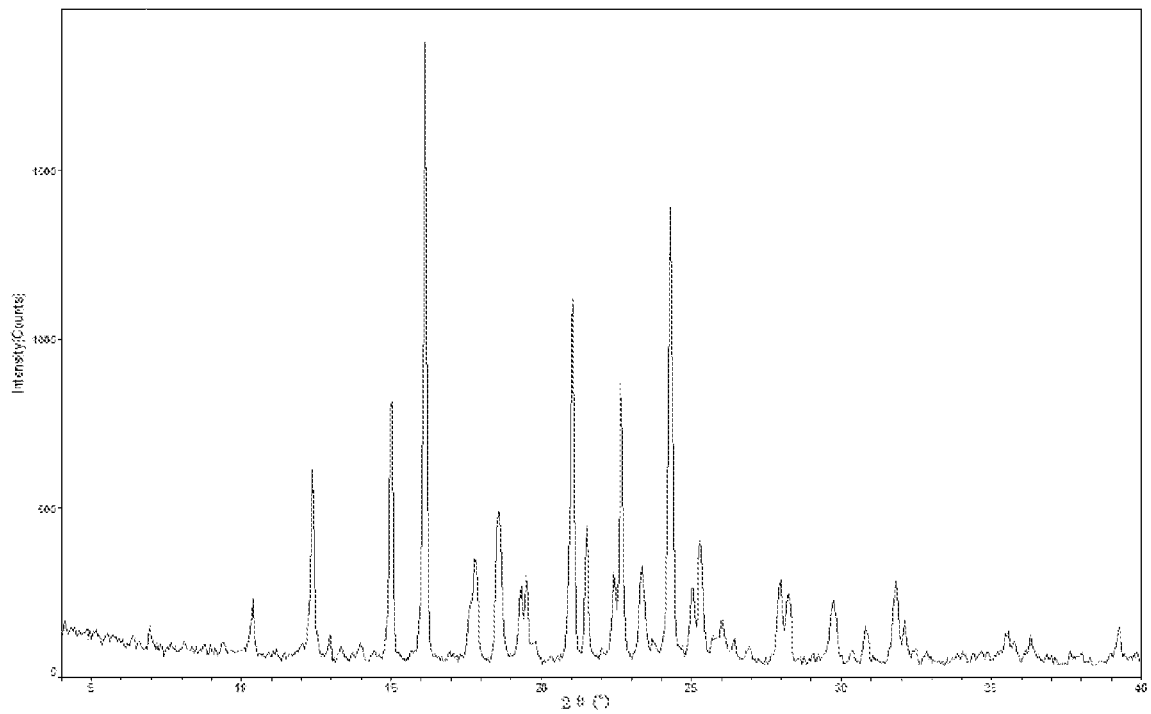
FIG. 22 shows an XRPD pattern of crystal form I.
Figure 23A:
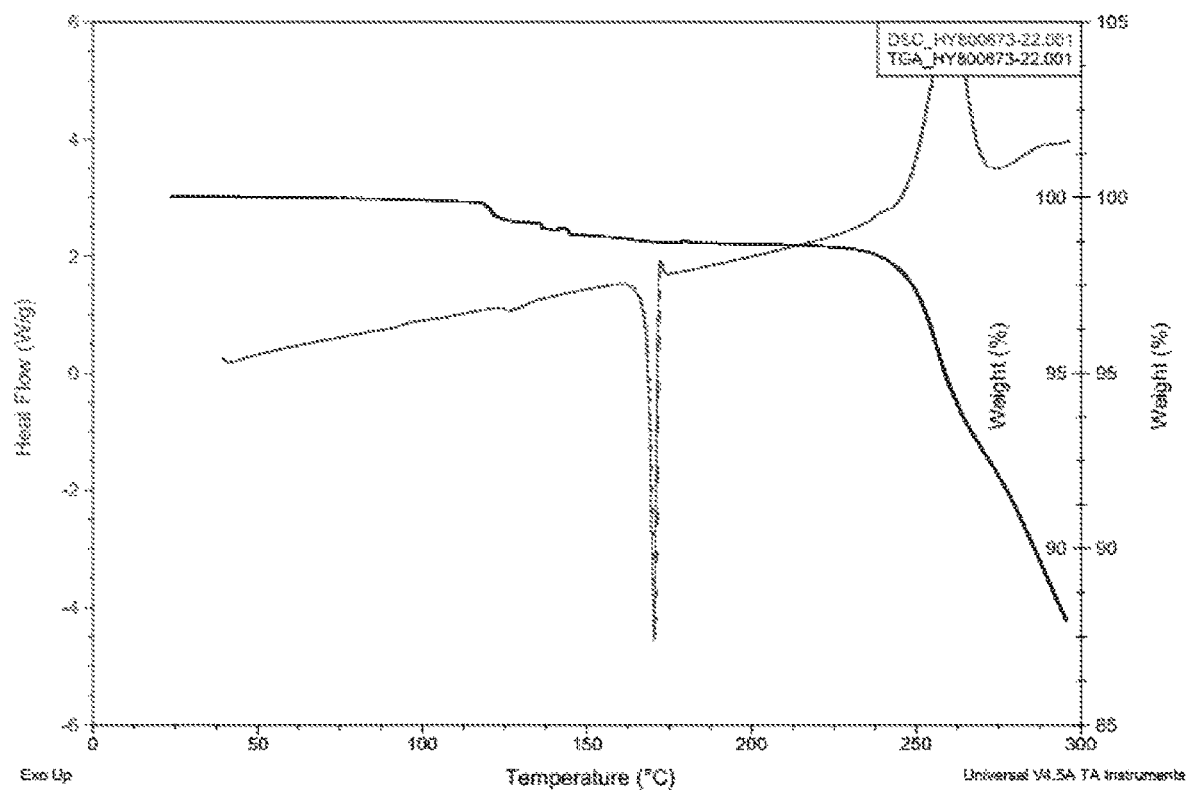
FIG. 23A shows a TGA/DSC pattern of crystal form I.

Example 3 Preparation of Crystal Form I of the Free Base of the Compound of Formula X Four slow cooling tests were performed using different solvent systems. About 20 mg of the compound of formula X prepared in Example 1 was weighed into a glass vial respectively, and an appropriate amount of solvent in the following table was added under a water bath condition of 60° C., stirred to dissolve and obtain a nearly saturated solution. After filtration, 200 μL of the corresponding solvent was added to the clear solution. The heating button was turned off and the solution was allowed to cool slowly. After the temperature was lowered to ambient temperature, the solution was placed under an ice bath condition to continually cool to about 4° C. The suspension was collected and was centrifuged at 12000 r/min for 15 min. The supernatant was poured, the solid was slowly evaporated overnight at ambient temperature, and the resulting solid was collected and subjected to XRPD test. The X-ray powder diffraction pattern of the crystal form I was substantially characterized as in FIG. 22. The TGA/DSC pattern was characterized as in FIG. 23A. The test results are shown in the following table, and the crystal form I was obtained in the slow evaporation test.

| Solvent | Crystal form |
|---|---|
| acetonitrile | crystal form I |
| ethyl acetate | crystal form I |
| methyl tert-butyl ether | crystal form I |
| isopropanol | crystal form I |

Example 4 Preparation of Crystal Form I of the Free Base of the Compound of Formula X Six suspension shaking tests (suspension stirring) at 25° C. were performed using different solvent systems. About 20 mg of the compound of formula X prepared in Example 1 was weighed into a 5 mL EP tube respectively, and 1 mL of the organic reagents in the following table were added, placed at 25° C., and shaken at 225 r/min for 15 min. The supernatant was poured, the solid was slowly evaporated overnight at ambient temperature, and the resulting solid was collected and subjected to XRPD test. The test results are shown in the table below, the crystal form I was obtained in suspension shaking test at 25° C.

| Solvent | the crystal form obtained by shaking for 1 day | the crystal form obtained by shaking for 7 days |
|---|---|---|
| methanol | crystal form I | crystal form I |
| ethanol | crystal form I | crystal form I |
| acetonitrile | crystal form I | crystal form I |
| ethyl acetate | crystal form I | crystal form I |
| methyl tert-butyl ether | crystal form I | crystal form I |
| isopropanol | crystal form I | crystal form I |

Example 5 Preparation of Crystal Form II of the Free Base of the Compound of Formula X Two slow cooling tests were performed using different solvent systems. About 20 mg of the compound of formula X prepared in Example 1 was weighed into a glass vial respectively, and an appropriate amount of solvent in the following table was added under a water bath condition of 60° C., stirred to dissolve and obtain a nearly saturated solution. After filtration, 200 µL of the corresponding solvent was added to the clear solution. The heating button was turned off and the solution was allowed to cool slowly. After the temperature was lowered to ambient temperature, the solution was placed under an ice bath condition to continuously cool to about 4° C. The suspension was collected and was centrifuged at 12000 r/min for 15 min. The supernatant was poured, the solid was slowly evaporated overnight at ambient temperature, and the resulting solid was collected and subjected to XRPD test. The test results are shown in the following table, and the crystal form II was obtained in the slow evaporation test.

| Solvent | Solid crystal form |
|---|---|
| methanol | crystal form II |
| ethanol | crystal form II |

Figure 24:
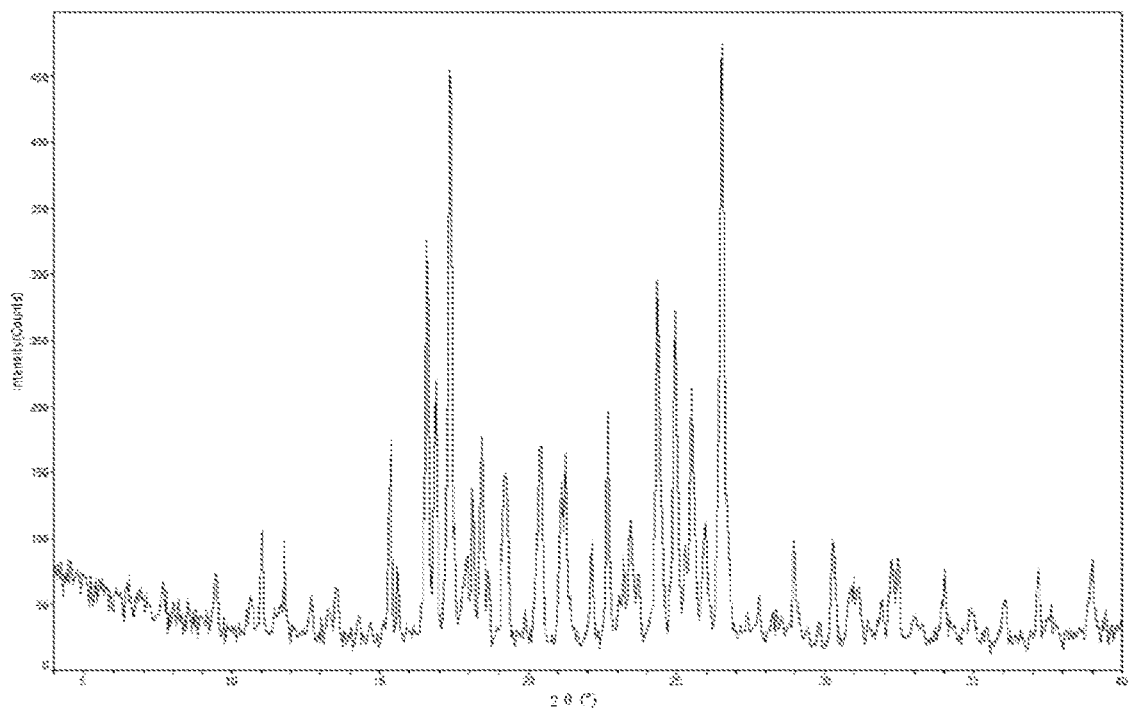
FIG. 24 shows an XRPD pattern of crystal form II.
Figure 25A:
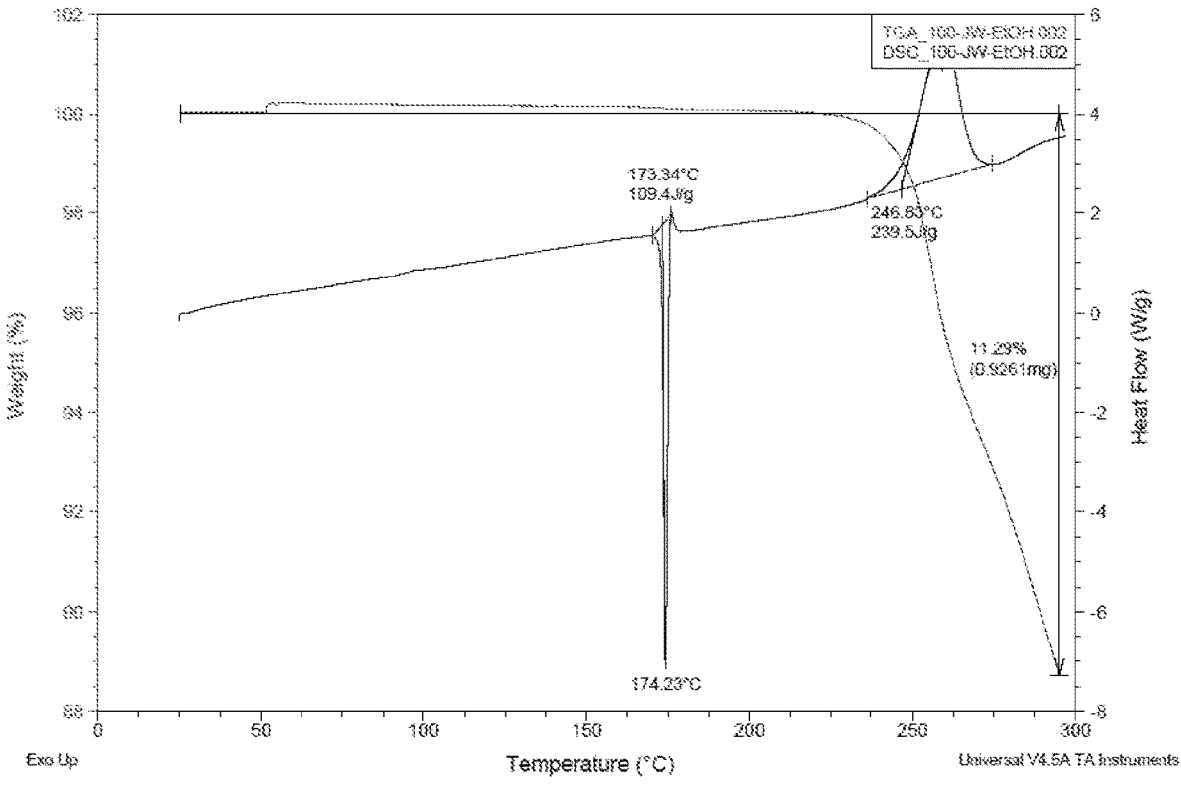
FIG. 25A shows a TGA/DSC pattern of crystal form II.

Example 6 Preparation of Crystal Form II of the Free Base of the Compound of Formula X Six suspension shaking tests (suspension stirring) at 50° C. were performed using different solvent systems. About 20 mg of a mixture of the crystal form I prepared in Examples 2-4 and the crystal form II prepared in Example 5 was weighed into a 5 mL EP tube respectively, and 1 mL of the organic reagents in the following table were added, placed at 50° C., and suspension shaken at 225 r/min. After one day, the suspension was collected and centrifuged at 12000 r/min for 15 min. The supernatant was poured, the solid was slowly evaporated overnight at ambient temperature, and the resulting solid was collected and subjected to XRPD test. The X-ray powder diffraction pattern of the crystal form II was substantially characterized as in FIG. 24, and the TGA/DSC pattern was characterized as in FIG. 25A. The test results are shown in the following table, and the crystal form II was obtained in the suspension shake test.

| Solvent | Crystal form |
|---|---|
| methanol | crystal form II |
| ethanol | crystal form II |
| methyl tert-butyl ether | crystal form II |
| acetonitrile | crystal form II |
| ethyl acetate | crystal form II |
| isopropanol | crystal form II |

Figure 2A:
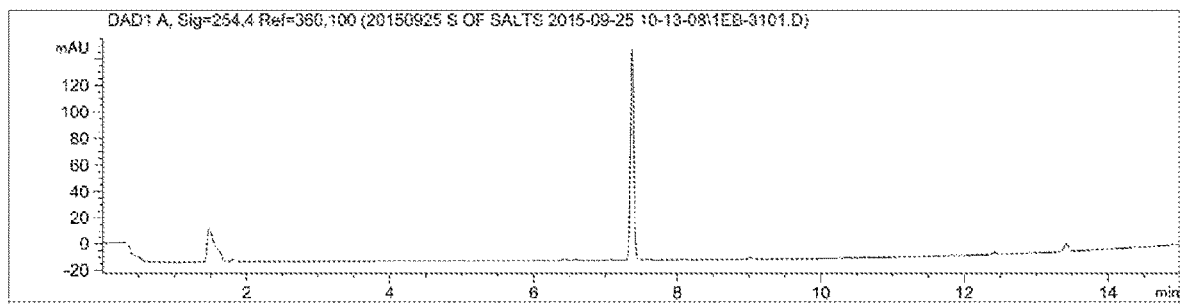
FIG. 2A shows an HPLC spectrum of crystal form A.
Figure 2B:
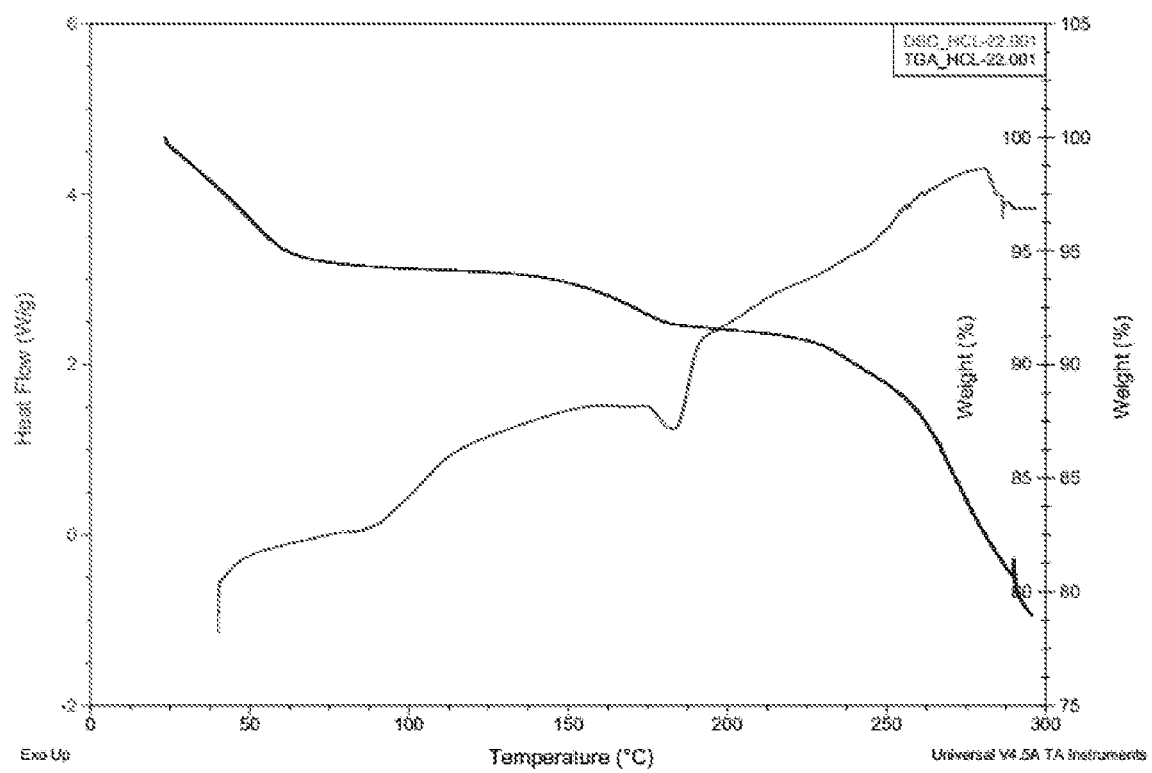
FIG. 2B shows a TGA/DSC pattern of crystal form A.

Example 7 Preparation of Crystal Form a of the Compound of Formula X 200 mg of free base sample was weighed and added to 20 mL glass vial, and 3 mL of acetone was added. The mixture was dissolved under ultrasound to form a yellow clear solution. A hydrochloric acid solution (1 mol/L, 536 µL) was slowly added while stirring at 50° C., and the mixture reacted at this temperature for 2 h. The mixture was slowly cooled to 0° C. after 2 hours, and kept at 0° C. for 2 hours. The solid was separated after filtered under vacuum, and washed with acetone for 3 to 5 times, dried under vacuum at 60° C. overnight, and the solid product was obtained. The yield was 64.3%. The X-ray powder diffraction pattern of the resulting crystal was as shown in FIG. 1 (2θ angles were marked), the HPLC was as shown in FIG. 2A, and the TGA/DSC pattern was characterized as in FIG. 2B. The molar ratio of acid to base is 1.05:1. The crystal form is defined as crystal form A in the present disclosure.

Figure 3:
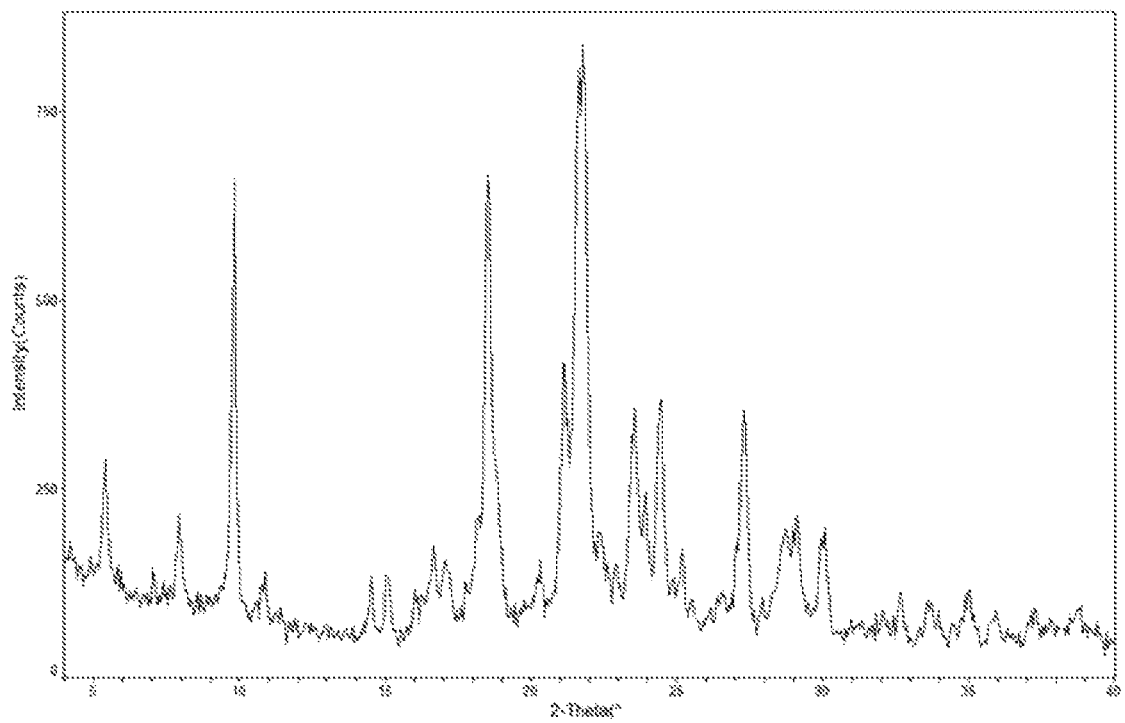
FIG. 3 shows an XRPD pattern of crystal form B-1.
Figure 4A:
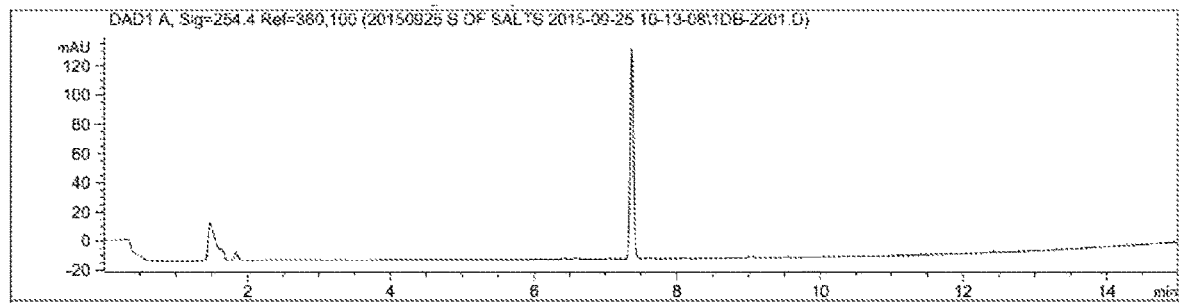
FIG. 4A shows an HPLC spectrum of crystal form B-1.
Figure 4B:
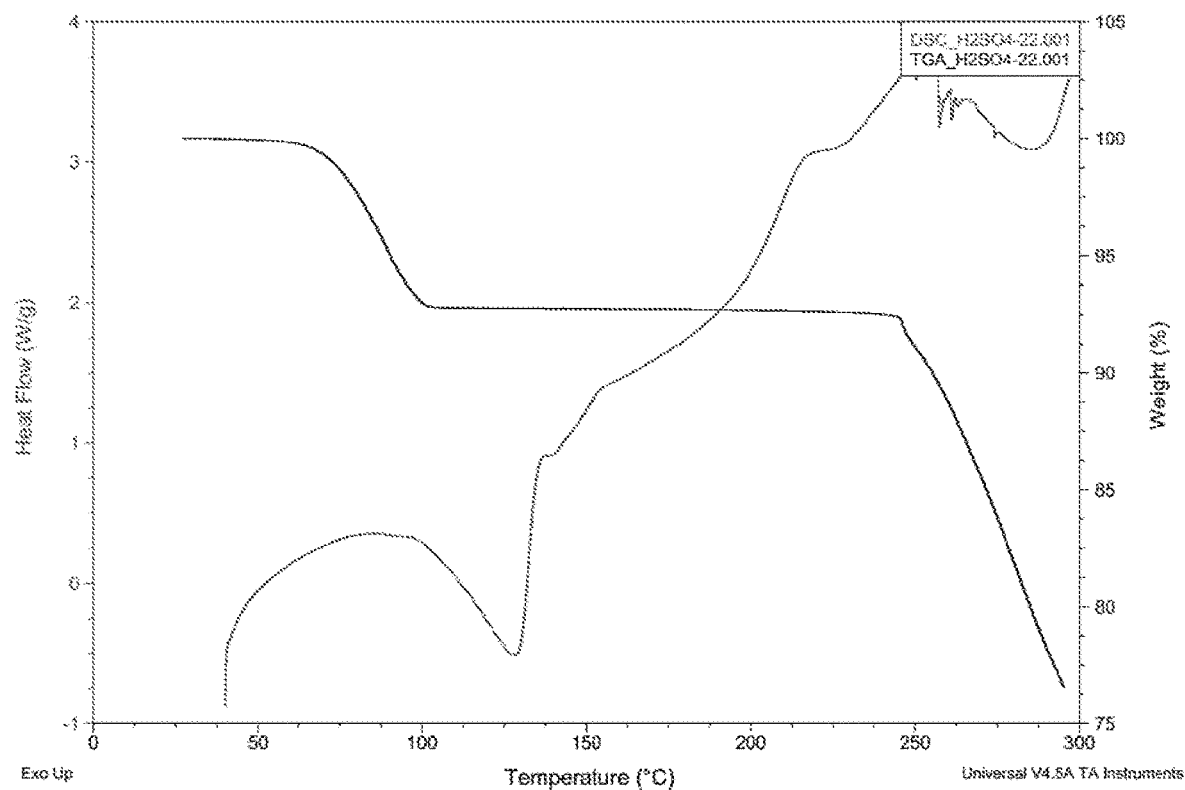
FIG. 4B shows a TGA/DSC pattern of crystal form B-1.

Example 8 Preparation of Crystal Form B-1 of the Compound of Formula X 200 mg of free base sample was weighed and added to 20 mL glass vial, and 3 mL of acetone was added. The mixture was dissolved under ultrasound to form a yellow clear solution. A sulfuric acid solution (0.5 mol/L, 536 µL) was slowly added while stirring at 50° C., and the mixture reacted at this temperature for 2 h. The mixture was slowly cooled to 0° C. after 2 hours, and kept at 0° C. for 2 hours. The solid was separated after filtered under vacuum, and washed with acetone for 3 to 5 times, dried under vacuum at 60° C. overnight, and the solid product was obtained. The yield was 84.8%. The X-ray powder diffraction pattern of the resulting crystal was as shown in FIG. 3 (2θ angles were marked), the HPLC was as shown in FIG. 4A, and the TGA/DSC pattern was characterized as in FIG. 4B. The molar ratio of acid to base is 0.47:1. The crystal form is defined as crystal form B-1 in the present disclosure.

Figure 6:
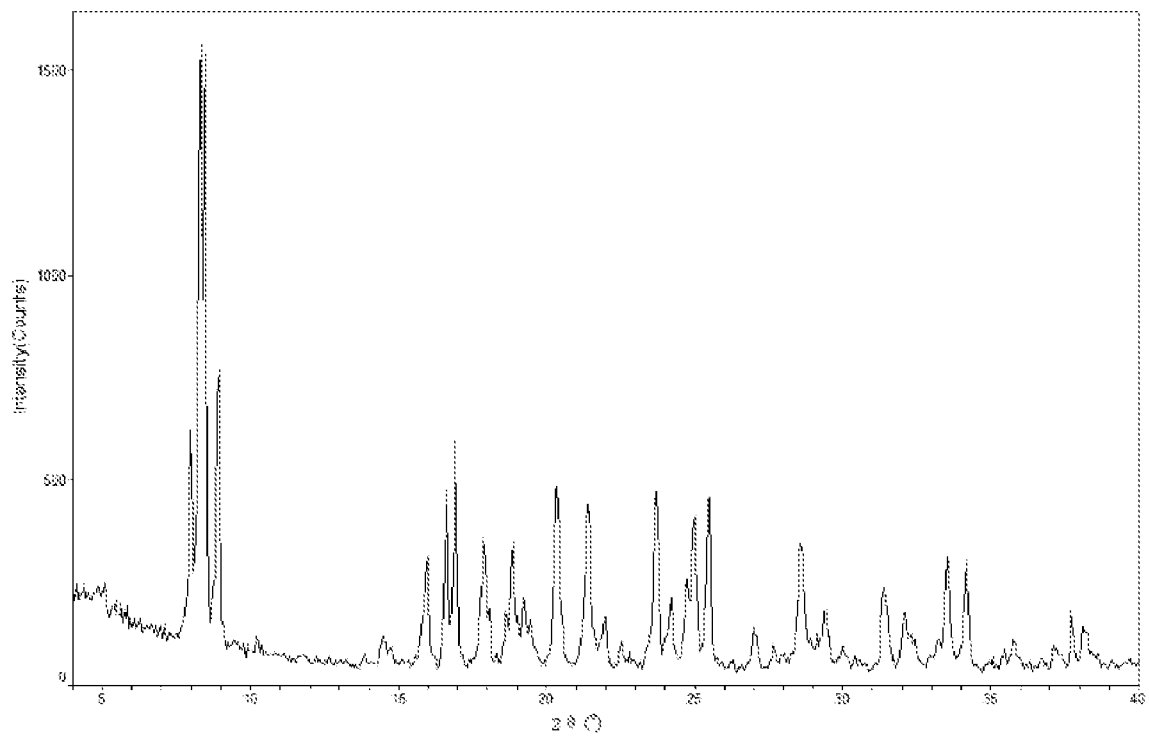
FIG. 6 shows an XRPD pattern of crystal form C.
Figure 7A:
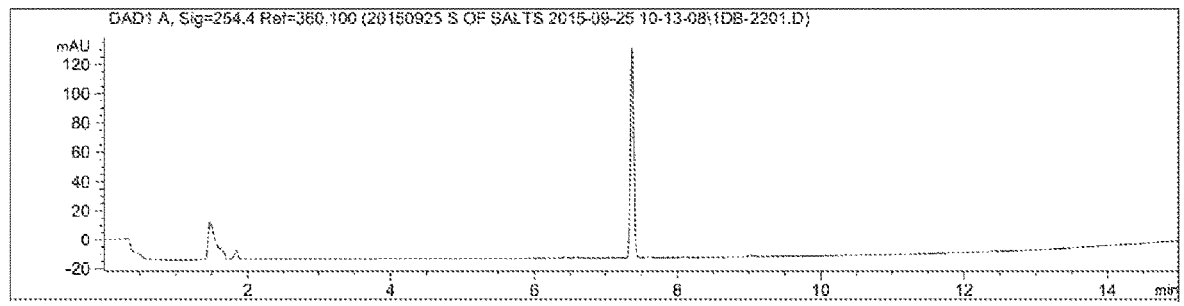
FIG. 7A shows an HPLC spectrum of crystal form C.
Figure 7B:
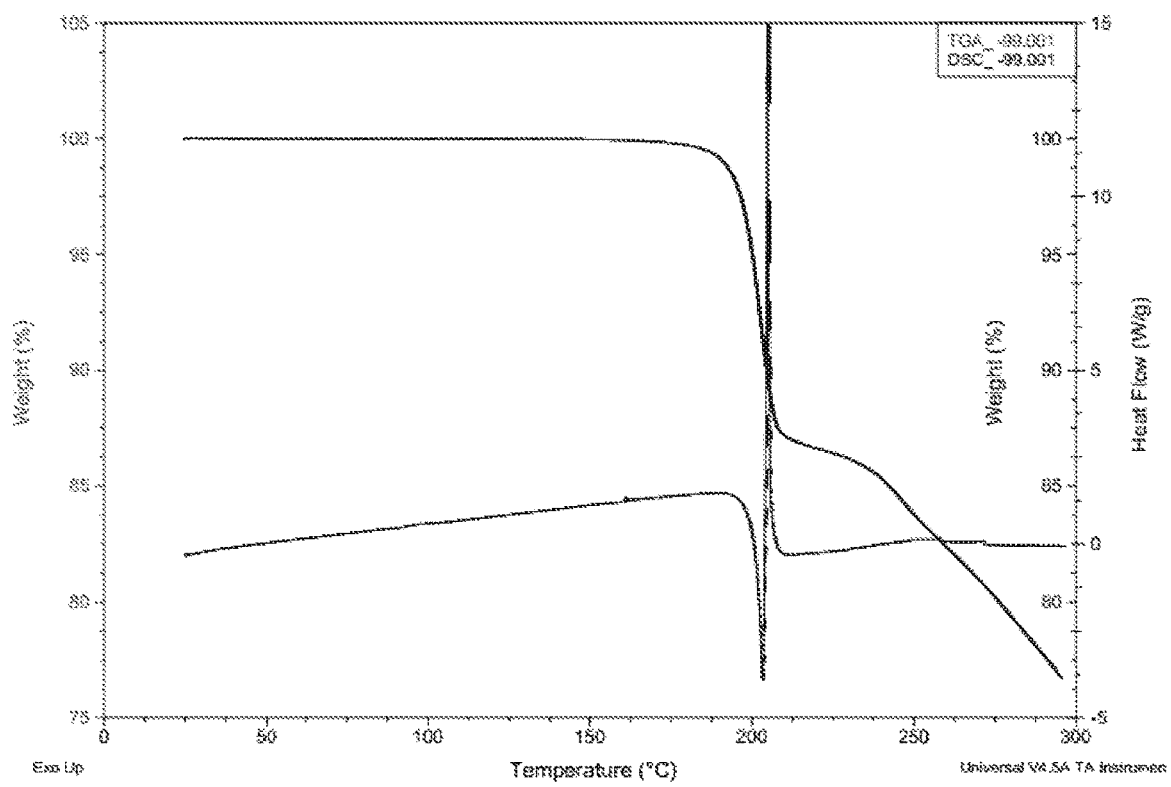
FIG. 7B shows a TGA/DSC pattern of crystal form C.
Figure 7C:
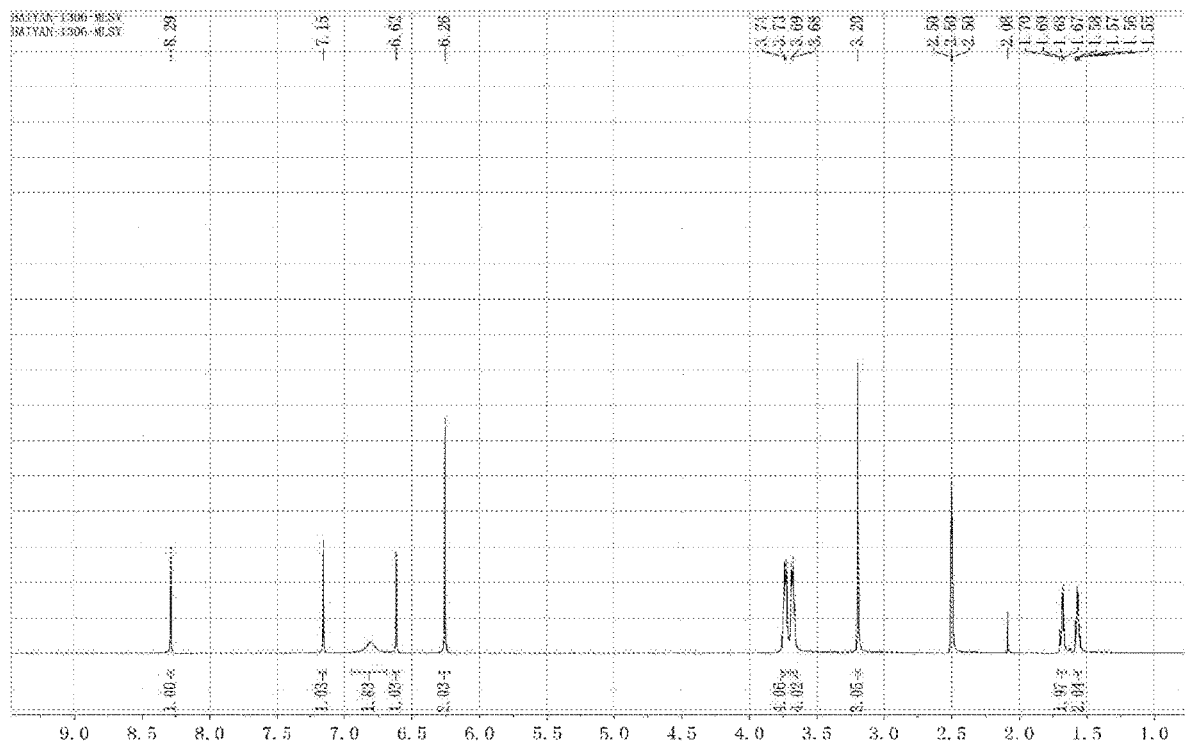
FIG. 7C shows a $^1$HNMR spectrum of crystal form C.

Example 9 Preparation of Crystal Form C of the Compound of Formula X 200 mg free base sample was weighed and added to 20 mL glass vial, and 3 mL of acetone was added. The mixture was dissolved under ultrasound to form a yellow clear solution. A maleic acid solution (1 mol/L, 536 µL) was slowly added while stirring at 50° C., and the mixture reacted at this temperature for 2 h. The mixture was slowly cooled to 0° C. after 2 hours, and kept at 0° C. for 2 hours. The solid was separated after filtered under vacuum, and washed with acetone for 3 to 5 times, dried under vacuum at 60° C. overnight, and the solid product was obtained. The yield was 89.6%. The X-ray powder diffraction pattern of the resulting crystal was as shown in FIG. 6 (2θ angles were marked), the HPLC of the crystal was as shown in FIG. 7A, the TGA/DSC pattern was characterized as in FIG. 7B, and the $^1$HNMR spectrum of crystal form C was as shown in FIG. 7C. The molar ratio of acid to base is 0.99:1. The melting point was 201.23° C.-205.23° C. The crystal form is defined as crystal form C in the present disclosure.

Figure 9:
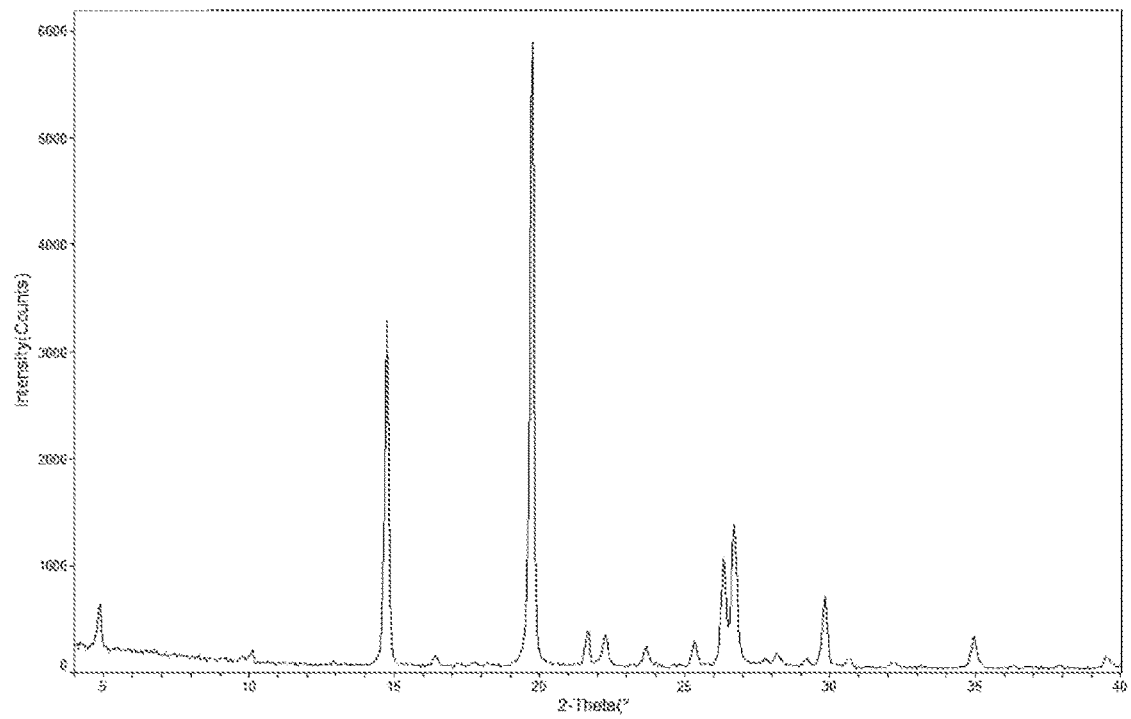
FIG. 9 shows an XRPD pattern of crystal form D-2.
Figure 10A:
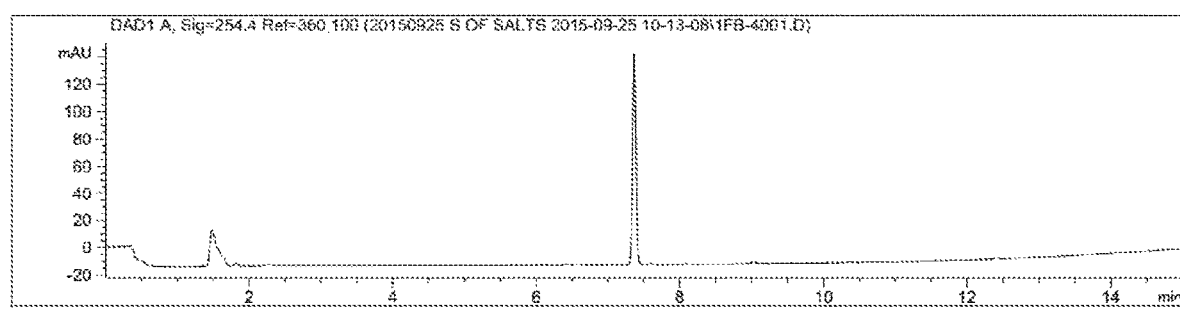
FIG. 10A shows an HPLC spectrum of crystal form D-2.
Figure 10B:
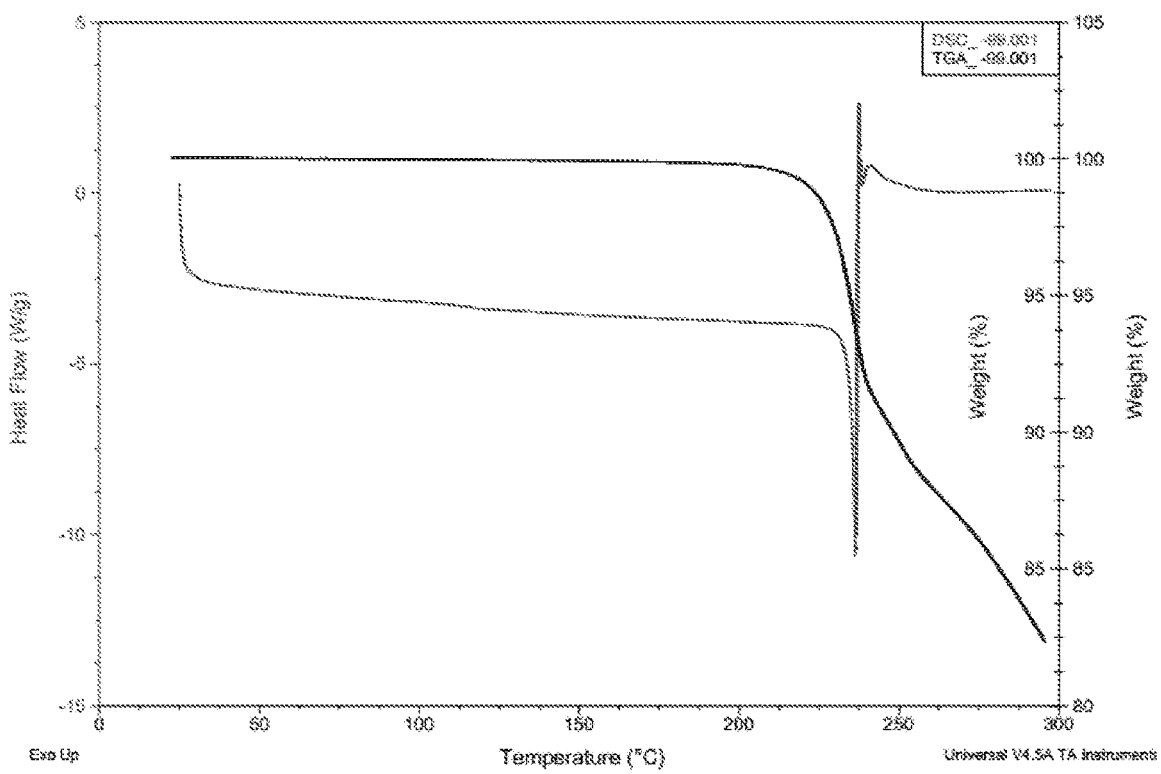
FIG. 10B shows a TGA/DSC pattern of crystal form D-2.
Figure 10C:
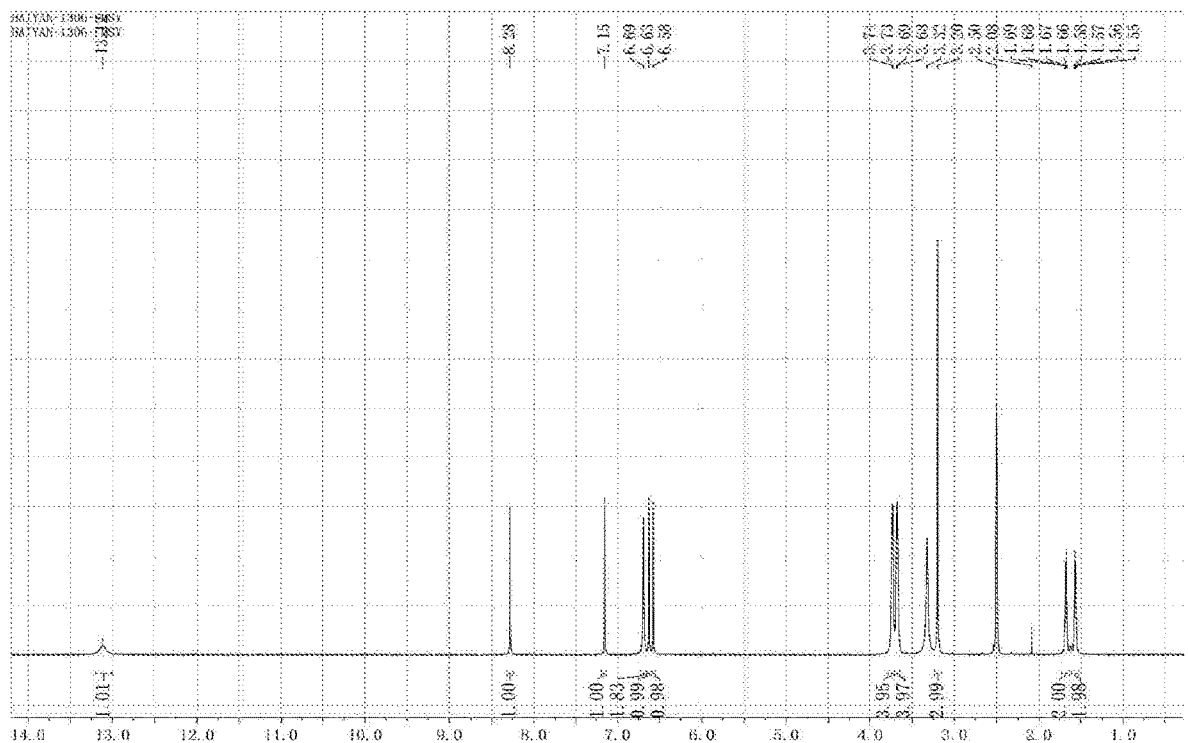
FIG. 10C shows a $^1$HNMR spectrum of crystal form D-2.

Example 10 Preparation of Crystal Form D-2 of the Compound of Formula X 200 mg free base sample was weighed and added to 20 mL glass vial, and 3 mL of acetone was added. The mixture was dissolved under ultrasound to form a yellow clear solution. An aqueous solution of fumaric acid in DMSO (0.25 mol/L, 2144 µL) was slowly added while stirring at 50° C., wherein a volume ratio of DMSO to water in the solution was 1:1, and the mixture reacted at this temperature for 2 h. The mixture was slowly cooled to 0° C. after 2 hours, and kept at 0° C. for 2 hours. The solid was separated after filtered under vacuum, and washed with acetone for 3 to 5 times, dried under vacuum at 60° C. overnight, and the solid product was obtained. The yield was 79.0%. The X-ray powder diffraction pattern of the resulting crystal was as shown in FIG. 9 (2θ angles were marked), the HPLC was as shown in FIG. 10A, the TGA/DSC pattern was characterized as in FIG. 10B, and the ¹H NMR spectrum was as shown in FIG. 10C. The molar ratio of acid to base is 0.49:1. The melting point was 234.36° C.-238.36° C. The crystal form is defined as crystal form D-2 in the present disclosure.

Figure 11:
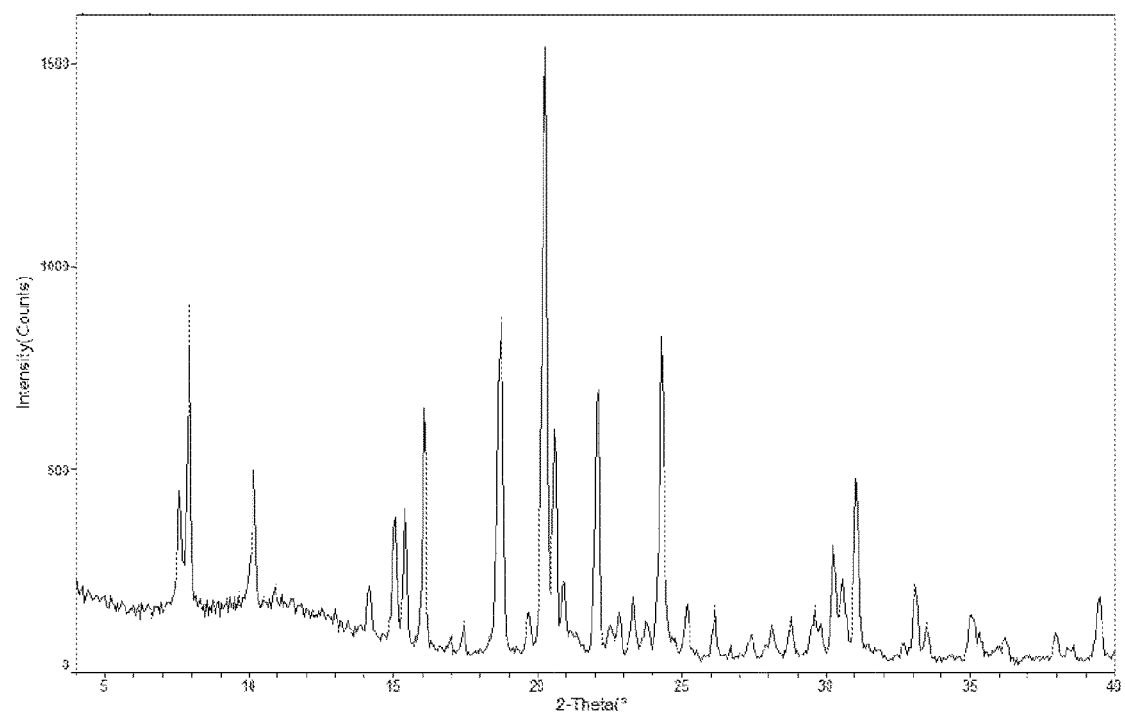
FIG. 11 shows an XRPD pattern of crystal form E.
Figure 12A:
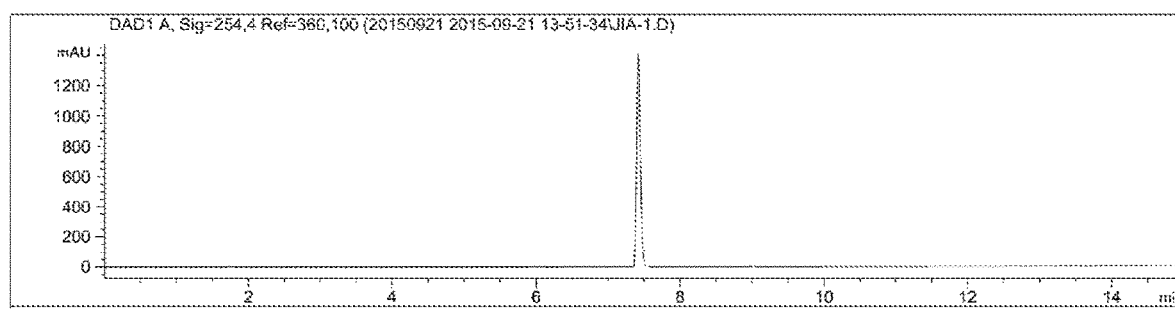
FIG. 12A shows an HPLC spectrum of crystal form E.
Figure 12B:
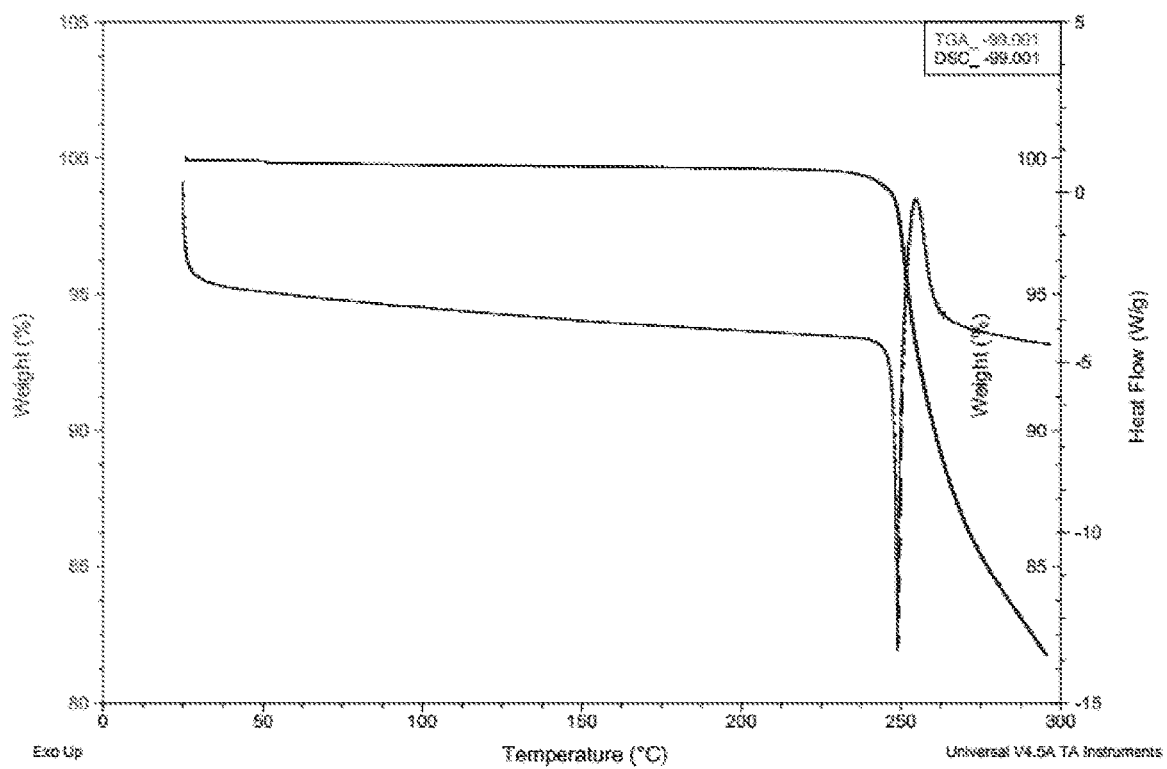
FIG. 12B shows a TGA/DSC pattern of crystal form E.
Figure 12C:
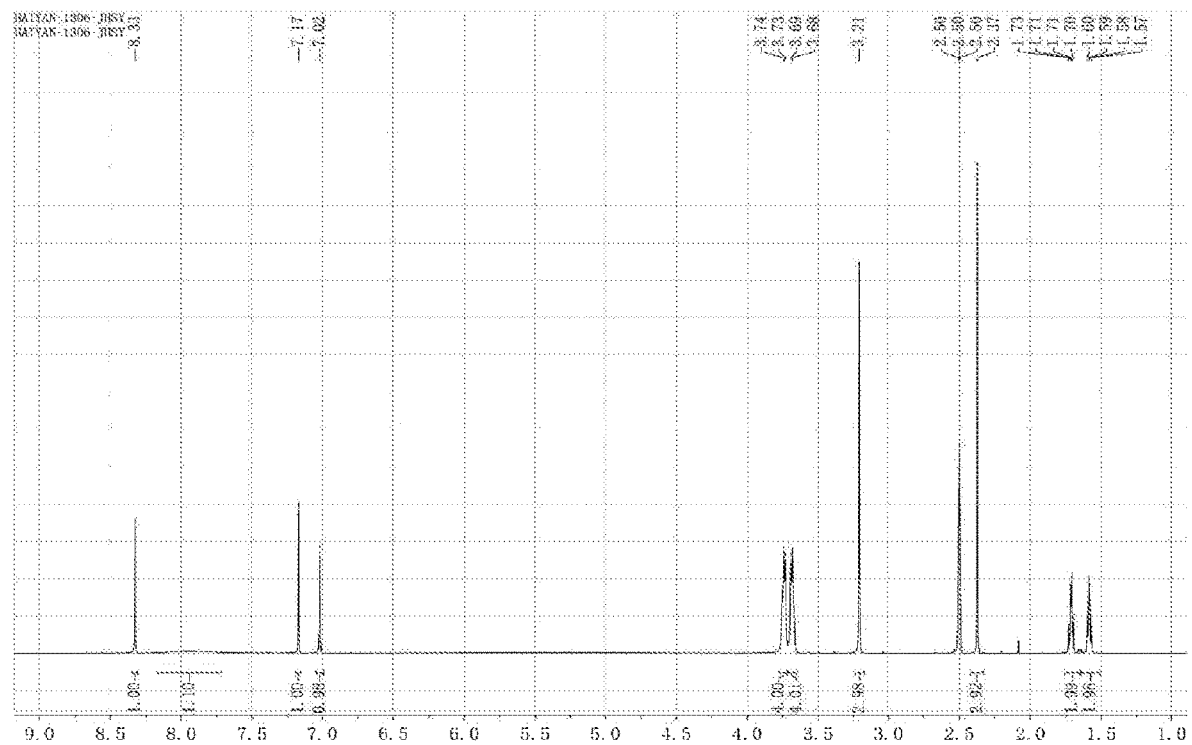
FIG. 12C shows a $^1$HNMR spectrum of crystal form E.
Figure 13:
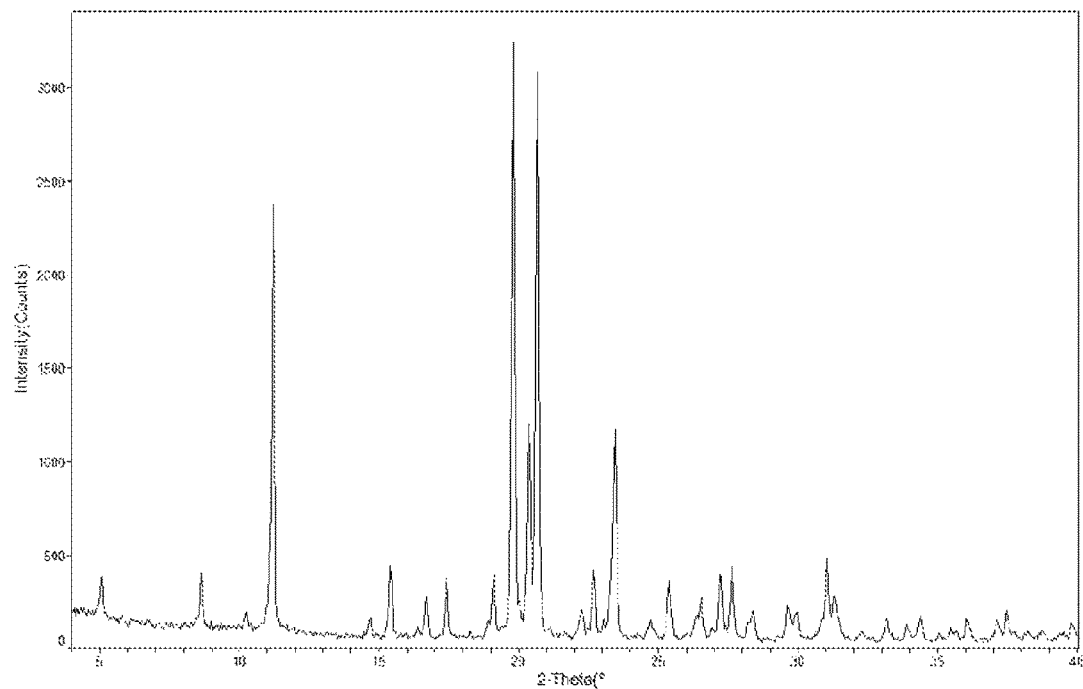
FIG. 13 shows an XRPD pattern of crystal form F.
Figure 14A:
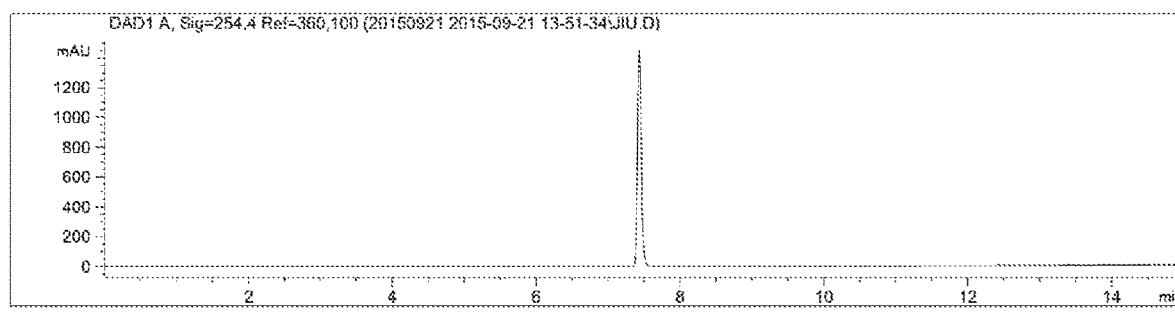
FIG. 14A shows an HPLC spectrum of crystal form F.
Figure 14B:
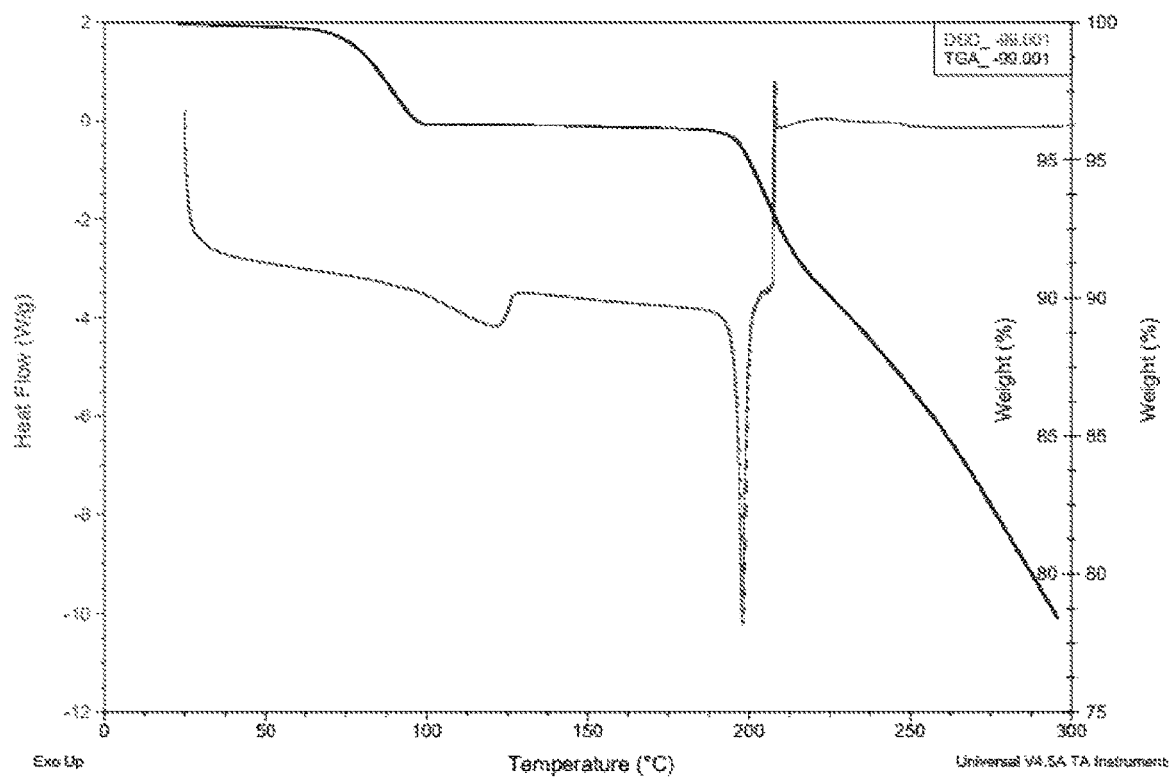
FIG. 14B shows a TGA/DSC pattern of crystal form F.
Figure 14C:
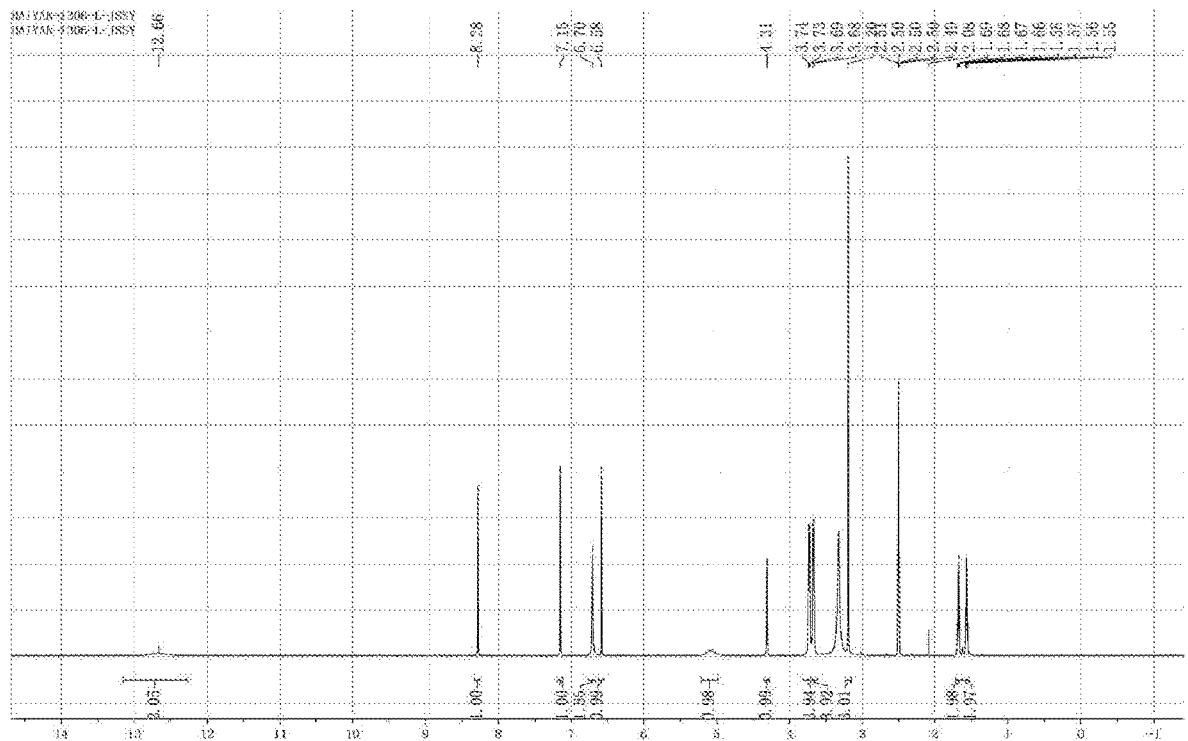
FIG. 14C shows a 1HNMR spectrum of crystal form F.

Example 11 Preparation of Crystal Form E of the Compound of Formula X 100 mg free base sample was weighed and added to 20 mL glass vial, and 2 mL of acetone was added. The mixture was dissolved under ultrasound to form a yellow clear solution. An aqueous methanesulfonic acid solution (1 mol/L, 268 μL) was slowly added while stirring at 50° C., and the mixture reacted at this temperature for 1 h. The mixture was slowly cooled to 0° C. after 1 hour, and kept at 0° C. for 1 hour. The solid was separated after filtered under vacuum, and washed with acetone for 3 to 5 times, dried under vacuum at 60° C. for 4 hours, and the solid product was obtained. The X-ray powder diffraction pattern of the resulting crystal was as shown in FIG. 11 (2θ angles were marked), the HPLC was as shown in FIG. 12A, the TGA/DSC pattern was characterized as in FIG. 12B, and the ¹H NMR spectrum was as shown in FIG. 12C. The melting point was 246.89° C.-250.89° C. The crystal form is defined as crystal form E in the present disclosure.

hour. The solid was separated after filtered under vacuum, and washed with acetone for 3 to 5 times, dried under vacuum at 60° C. for 4 hours, and the solid product was obtained. The X-ray powder diffraction pattern of the resulting crystal was as shown in FIG. 13 (2θ angles were marked), the HPLC was as shown in FIG. 14A, the TGA/DSC pattern was characterized as in FIG. 14B, and the ¹H NMR spectrum was as shown in FIG. 14C. The melting point was 195.84° C.-199.84° C. The crystal form is defined as crystal form F in the present disclosure.

Example 13 Preparation of Various Crystal Forms of Salts of the Compound of Formula X 800 mg of the free base of the compound of formula X prepared in Example 1 was weighed, and 16 ml of tetrahydrofuran was added, the mixture was dissolved under ultrasound to prepare a 50 mg/ml solution. 0.4 ml of the solution was taken into a 1.5 ml sample bottle, and dried with a nitrogen blower. The corresponding acid was added in a molar ratio of acid to the free base of 1.2:1, followed by the addition of 1 ml of the corresponding solvent. The mixture was clarified by heating and sonication, and reacted at 50° C. for 4 h, and then was slowly cooled to precipitate a solid. The solid was collected by centrifugation. The clear solution induced crystallization by the anti-solvent addition. The solvent of fumaric acid solution was DMSO and water (1:1, v/v). The corresponding reaction temperatures and times for various types of acids and the physical properties of each salt are shown in the following table:

| Acid | The amount of acid (μL) | methanol (condition 1) | ethyl acetate (condition 2) | acetonitrile (condition 3) | acetone (condition 4) |
|---|---|---|---|---|---|
| Hydrochloric acid (1M) | 58.5 | crystal form A | crystal form A | crystal form A | crystal form A |
| Sulfuric acid (0.5M) | 58.5 | crystal form B-1 | crystal form B-2 | crystal form B-1 | crystal form B-1 |
| Hydrobromic acid (1M) | 58.5 | N/A | crystal form J | crystal form J | crystal form J |
| Phosphoric acid (1M) | 58.5 | crystal form G-1 | crystal form G-2 | crystal form G-3 | crystal form G-3 |
| Methanesulfonic acid (1M) | 58.5 | crystal form E | crystal form E | crystal form E | crystal form E |
| Maleic acid (1M) | 58.5 | crystal form C | crystal form C | crystal form C | crystal form C |
| L-tartaric acid (1M) | 58.5 | crystal form F | crystal form F | crystal form F | crystal form F |
| Citric acid (0.5M) | 117 | crystal form H-1 | crystal form H-2 | crystal form H-3 | crystal form H-3 |
| Fumaric acid (0.25M) | 234 | crystal form D-1 | crystal form D-1 | crystal form D-2 | crystal form D-2 |

| Crystal form | Crystallinity | Weight loss (%) | Endothermic peak (° C.) | Molar ratio of acid to base | Purity (%) |
|---|---|---|---|---|---|
| crystal form A | good | 6.79 | 183.73 | 1.05 | 100 |
| crystal form B-1 | good | 6.65 | 128.84 | 0.47 | 100 |
| crystal form C | good | 0.08 | 203.23 | 0.99 | 100 |
| crystal form D-2 | good | 0.11 | 236.36 | 0.49 | 100 |
| crystal form E | good | 0.32 | 248.89 | 1 | 100 |
| crystal form F | good | 3.70 | 197.84 | 1 | 100 |

N/A: solid was not obtained.

Figure 5:
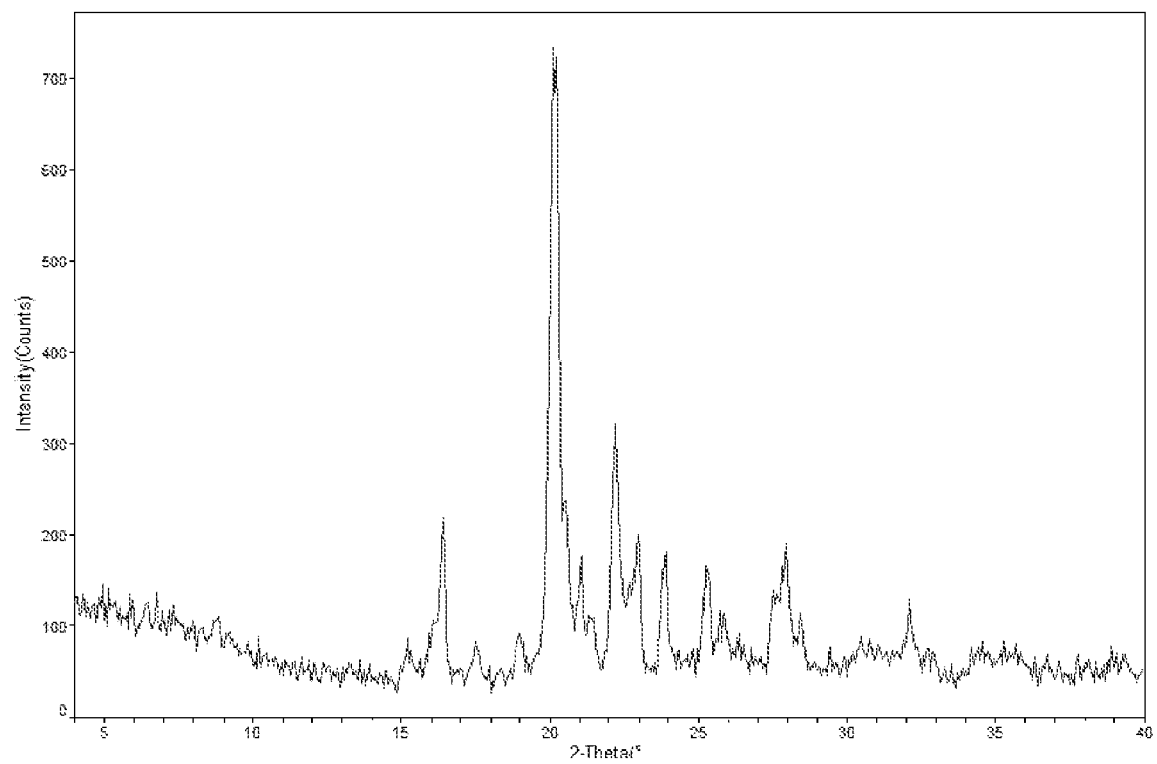
FIG. 5 shows an XRPD pattern of crystal form B-2.
Figure 8:
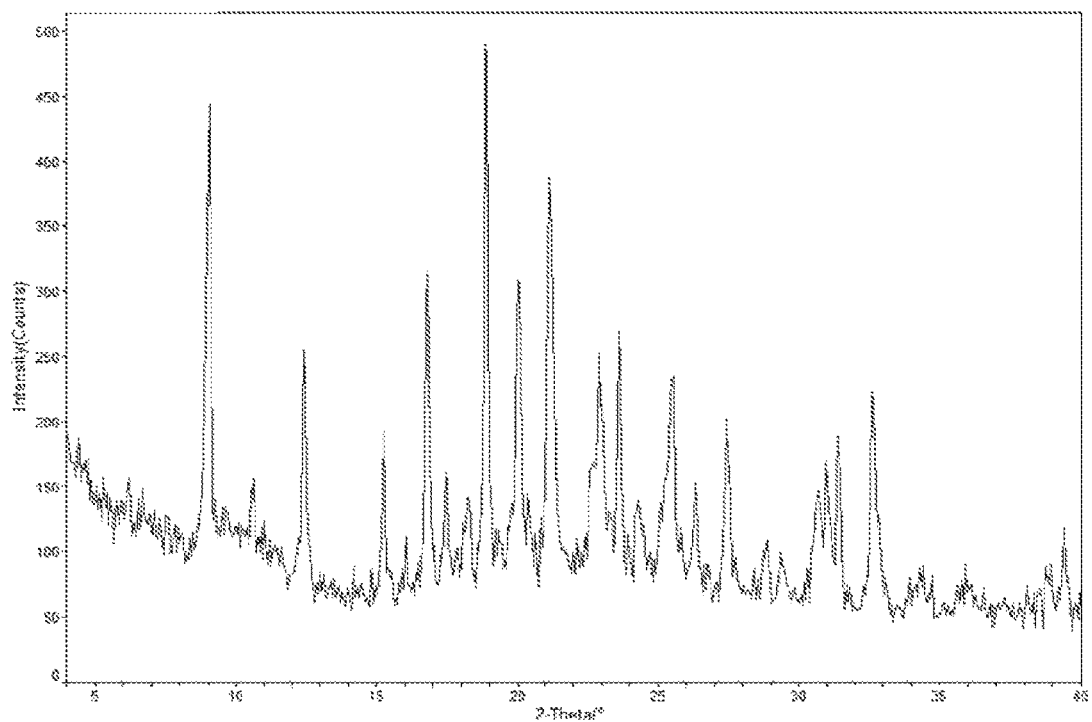
FIG. 8 shows an XRPD pattern of crystal form D-1.
Figure 15:
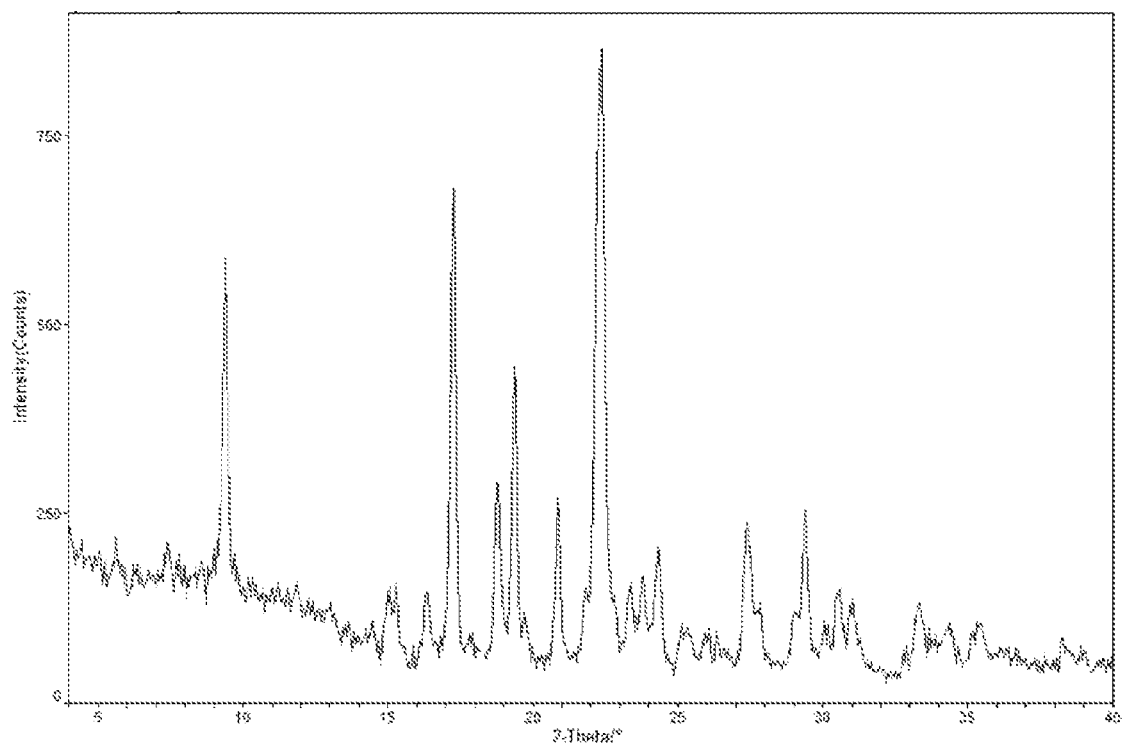
FIG. 15 shows an XRPD pattern of crystal form G-1.
Figure 16:
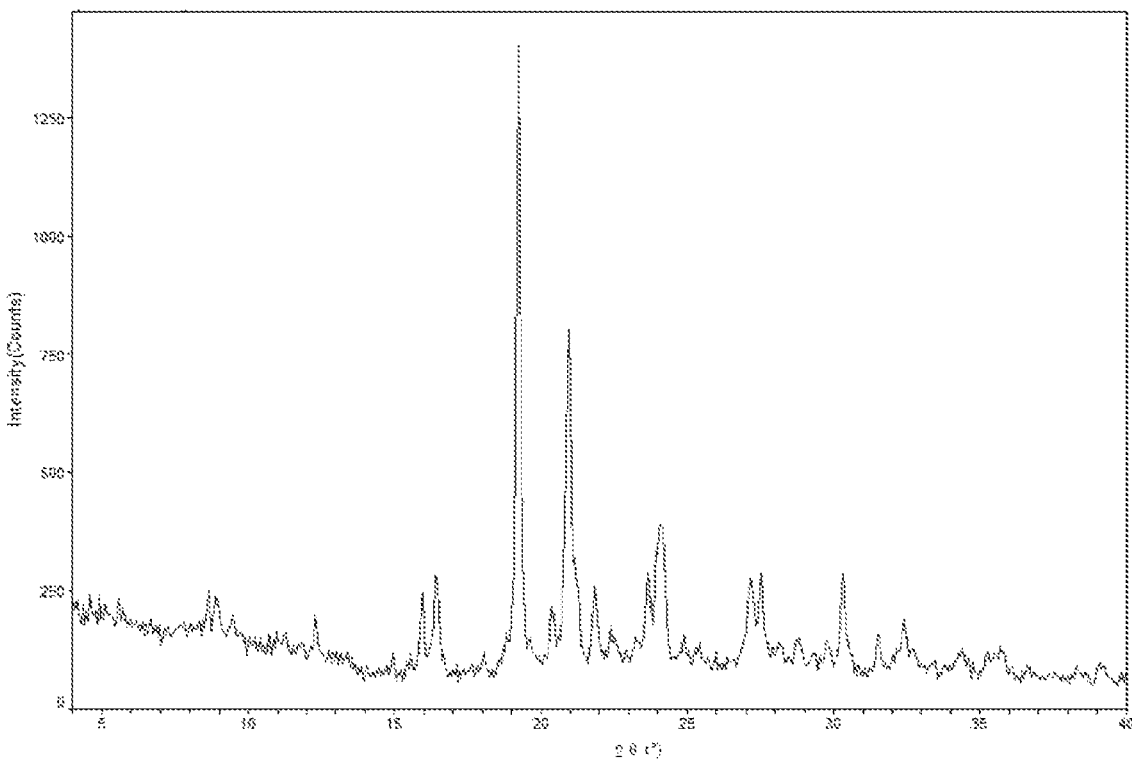
FIG. 16 shows an XRPD pattern of crystal form G-2.
Figure 17:
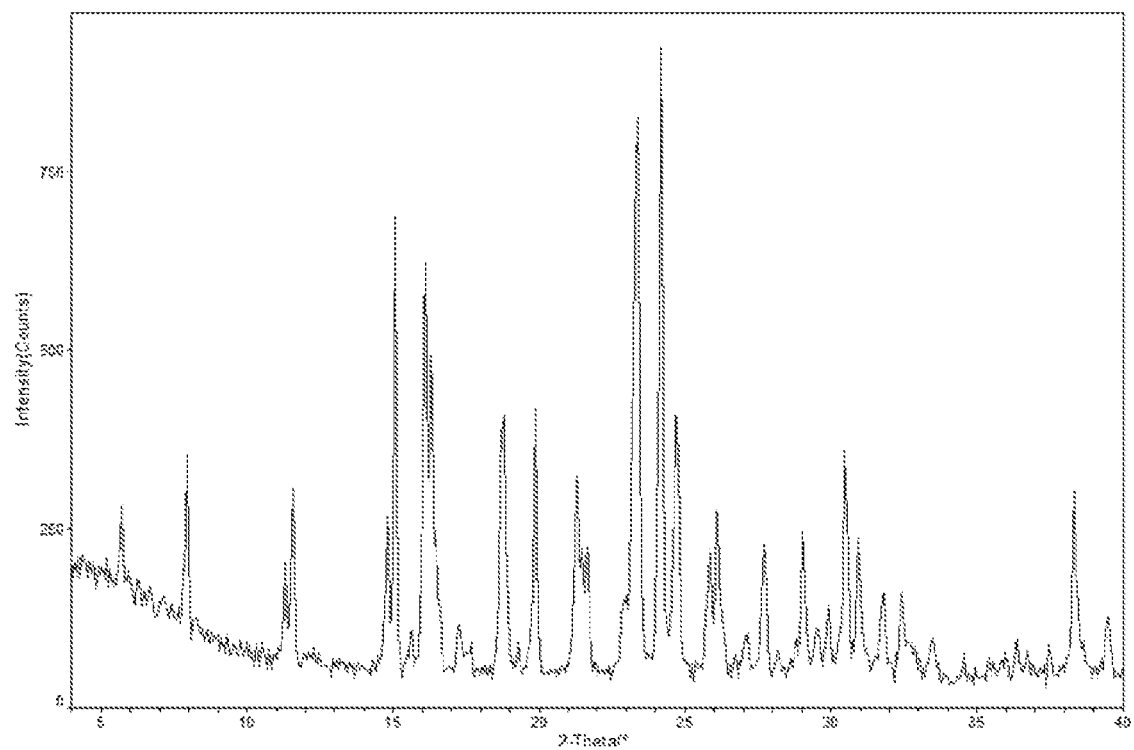
FIG. 17 shows an XRPD pattern of crystal form G-3.
Figure 18:
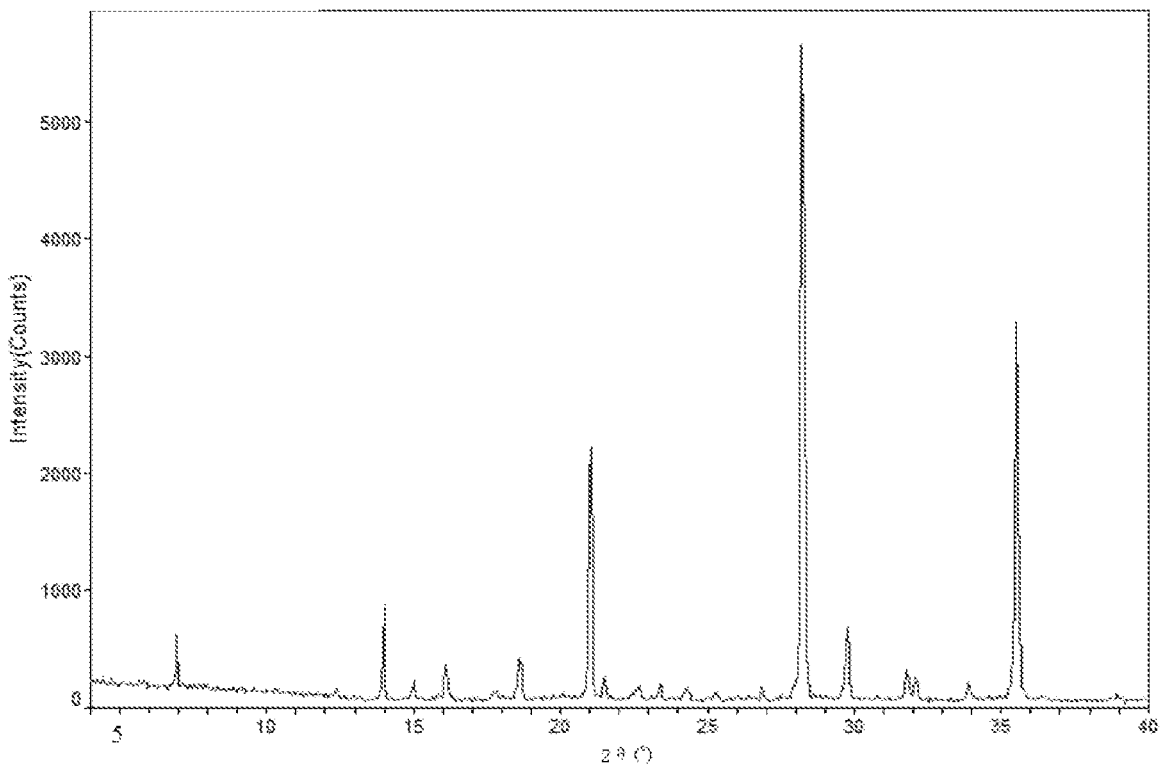
FIG. 18 shows an XRPD pattern of crystal form H-1.
Figure 19:
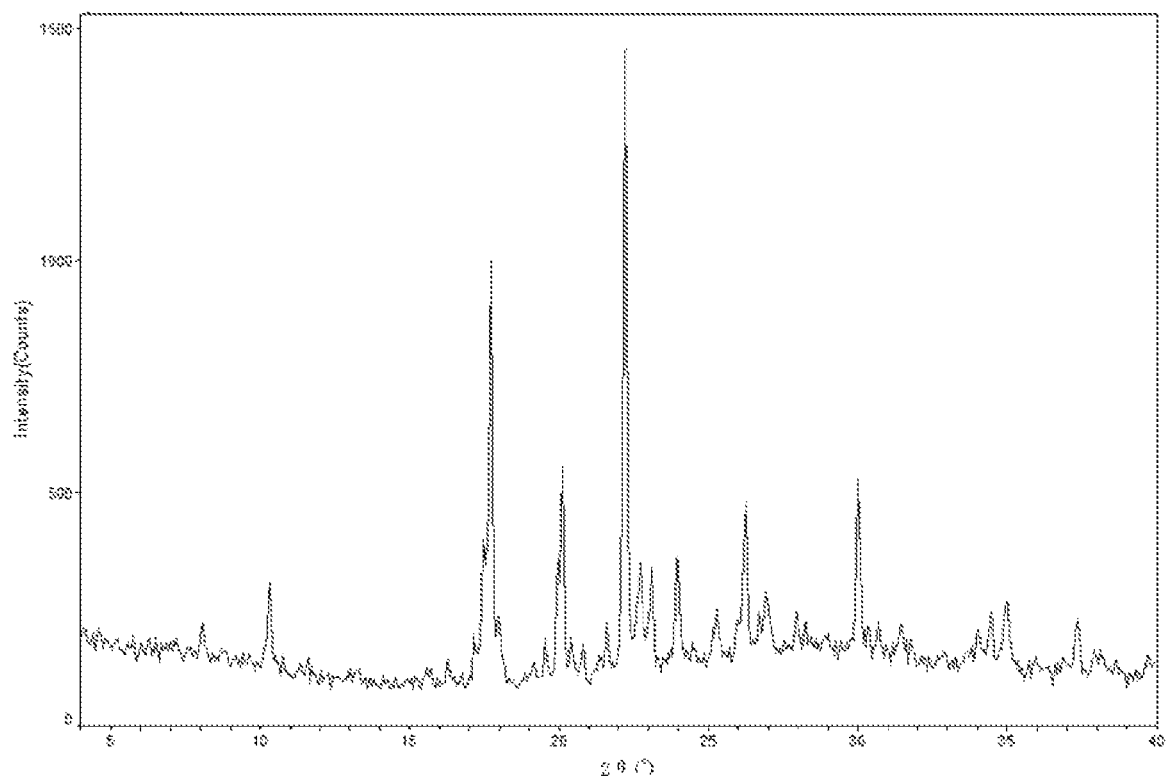
FIG. 19 shows an XRPD pattern of crystal form H-2.
Figure 20:
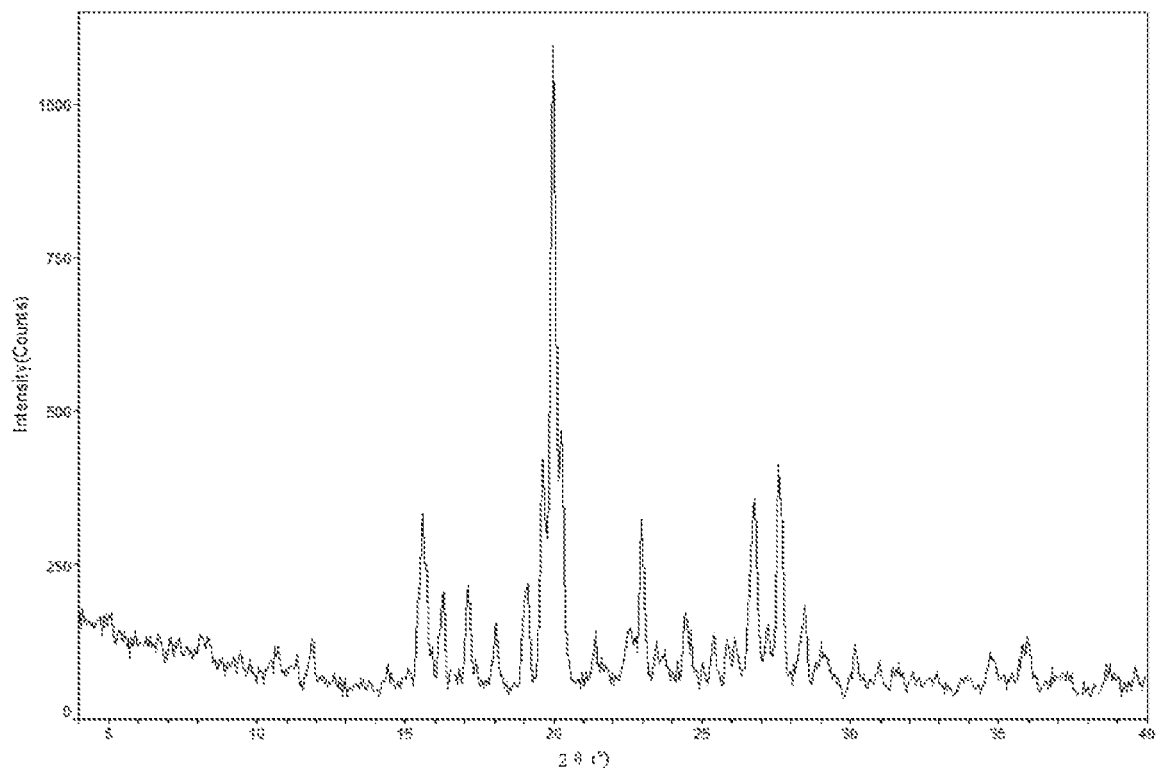
FIG. 20 shows an XRPD pattern of crystal form H-3.
Figure 21:
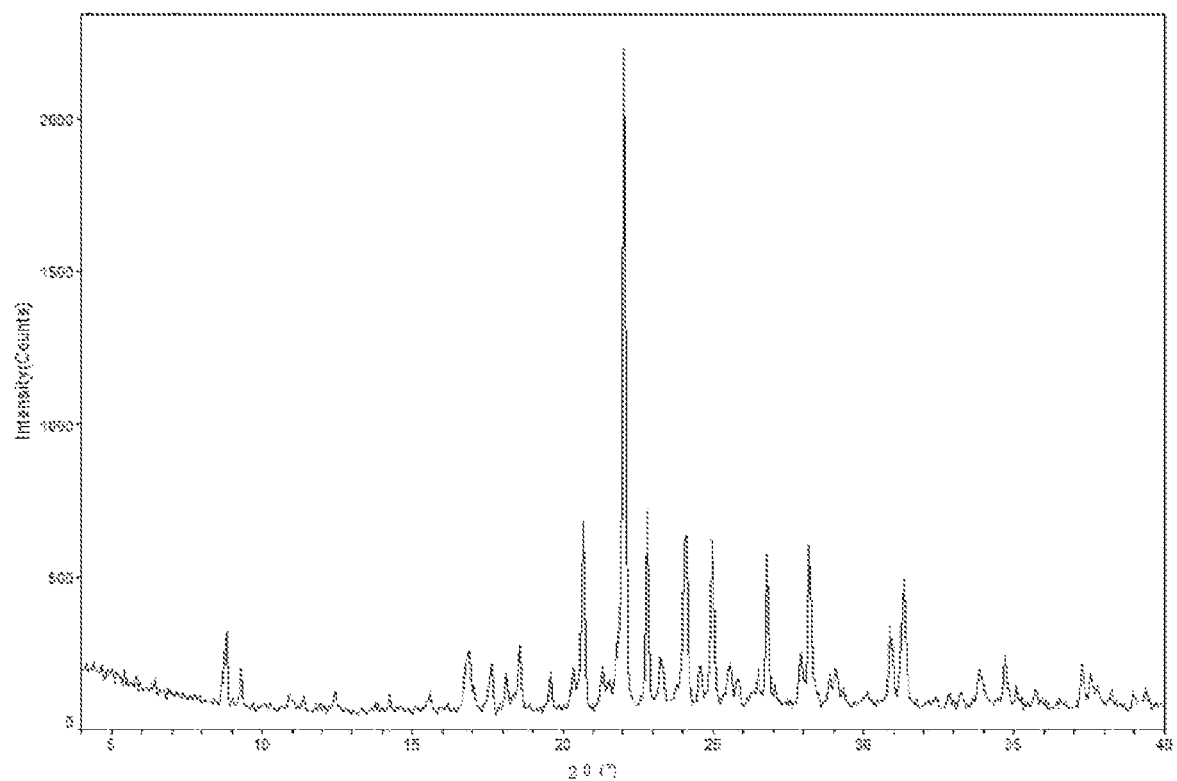
FIG. 21 shows an XRPD pattern of crystal form J.

Example 12 Preparation of Crystal Form F of the Compound of Formula X 100 mg free base sample was weighed and added to 20 mL glass vial, and 2 mL of acetone was added. The mixture was dissolved under ultrasound to form a yellow clear solution. An aqueous L-tartaric acid solution (1 mol/L, 268 μL) was slowly added while stirring at 50° C., and the mixture reacted at this temperature for 1 h. The mixture was slowly cooled to 0° C. after 1 hour, and kept at 0° C. for 1 wherein the X-ray powder diffraction pattern of the crystal form B-2 is substantially characterized as in FIG. 5; the X-ray powder diffraction pattern of the crystal form D-1 is substantially characterized as in FIG. 8; the X-ray powder diffraction pattern of the crystal form G-1 is substantially characterized as in FIG. 15; the X-ray powder diffraction pattern of the crystal form G-2 is substantially characterized as in FIG. 16; the X-ray powder diffraction pattern of the crystal form G-3 is substantially characterized as in FIG. 17; the X-ray powder diffraction pattern of the crystal form H-1 is substantially characterized as in FIG. 18; the X-ray powder diffraction pattern of the crystal form H-2 is substantially characterized as in FIG. 19; the X-ray powder diffraction pattern of the crystal form H-3 is substantially characterized as in FIG. 20; the X-ray powder diffraction pattern of the crystal form J is substantially characterized as in FIG. 21.

Example 14 Preparation of Various Salts of the Compound of Formula X 100 mg of the free base sample of the compound of formula X prepared in Example 1 was weighed, and added into a 20 mL glass vial, and 2 mL of acetone was added. The mixture was dissolved under ultrasound to form a yellow clear solution. The corresponding amount of acid was slowly added dropwise while stirring at 50° C., and the mixture reacted at this temperature for 1 h. The mixture was slowly cooled to 0° C. after 1 hour. When the temperature drops to 25° C., the clear solution becomes turbid, and kept at 0° C. for 1 hour. The solid was separated after filtered under vacuum, and washed with acetone for 3 to 5 times, dried under vacuum at 60° C. overnight, and the solid product was obtained. The original feed and the physical properties of each salt are shown in the following table.

| Salt type | The molar ratio of acid to the compound of formula X in the salt | The acid added and amount | Melting point |
|---|---|---|---|
| Hydrochloride | 1:1 | 268 μL 1M hydrochloric acid | N/A |
| Sulfate | 0.47:1 | 268 μL 0.5M sulfuric acid | N/A |
| Methanesulfonate | 1:1 | 268 μL 1M methanesulfonic acid | 246.89-250.89° C. |
| Maleate | 1:1 | 268 μL 1M methanesulfonic acid | 201.23-205.23° C. |
| Fumarate | 0.49:1 | 1072 μL 0.25M fumaric acid solution (DMSO:water = 1:1, v/v) | 234.36-238.36° C. |
| L-tartrate | 0.49:1 | 268 μL 1M L-tartaric acid | 195.84-199.84° C. |

Example 15 Solid Phase Stability Experiment 5 mg of samples were weighed and sealed at 60° C., respectively. Another set of samples were sealed and stored at −20° C. as a control at the same time. All samples were characterized by HPLC at 7 days and 21 days to detect changes in purity. The results are shown in the table below.

| Crystal form | 60° C.-0 day Purity (%) | 60° C.-0 day Total impurities (%) | 60° C.-7 days Purity (%) | 60° C.-7 days Total impurities (%) | 60° C.-21 days Purity (%) | 60° C.-21 days Total impurities (%) |
|---|---|---|---|---|---|---|
| crystal form A | 99.73 | 0.27 | 99.78 | 0.22 | 99.75 | 0.25 |
| crystal form B-1 | 99.74 | 0.26 | 99.50 | 0.50 | 99.74 | 0.26 |
| crystal form C | 99.73 | 0.27 | 99.74 | 0.26 | 99.75 | 0.25 |
| crystal form D-2 | 98.37 | 1.63 | 98.22 | 1.78 | 98.25 | 1.75 |

The data show that the crystal form A, crystal form B-1, crystal form C and crystal form D-2 have good stability at 7 days and 21 days, and the main component and impurities change little. The total impurities of the crystal form D-2 are slightly larger.

Example 16 Hygroscopicity Experiment

Figure 26:
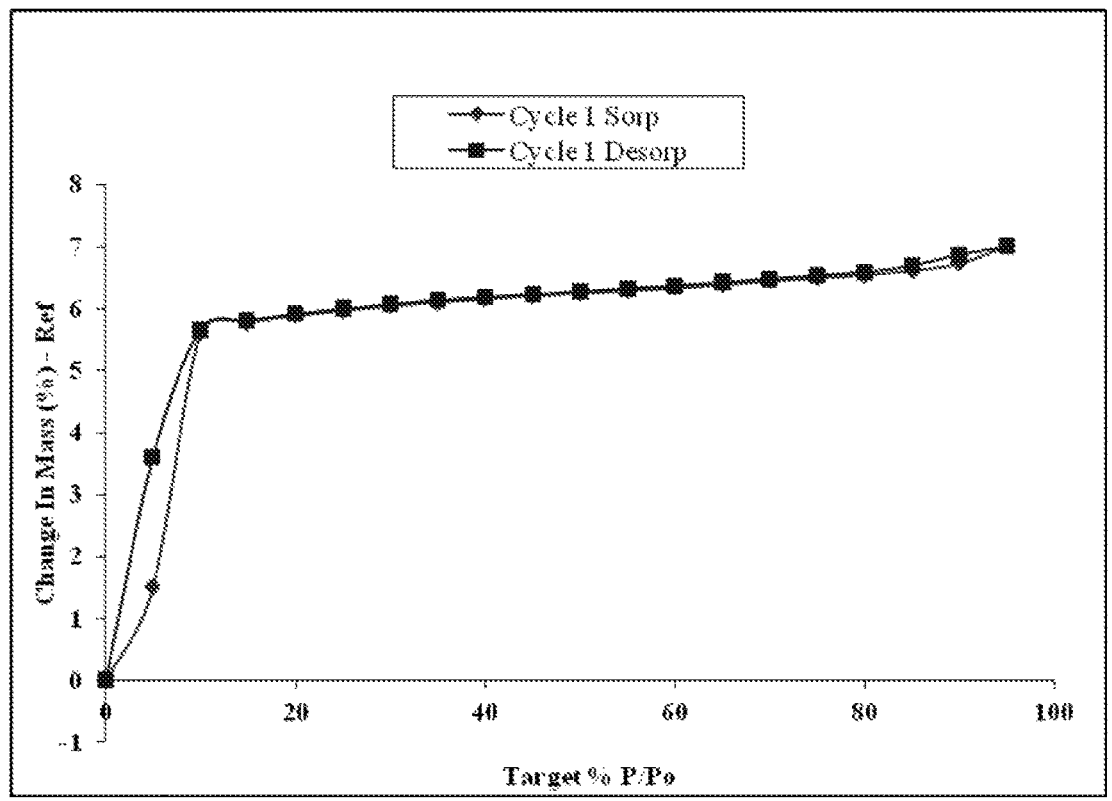
FIG. 26 shows a DVS pattern for crystal form A.
Figure 27:
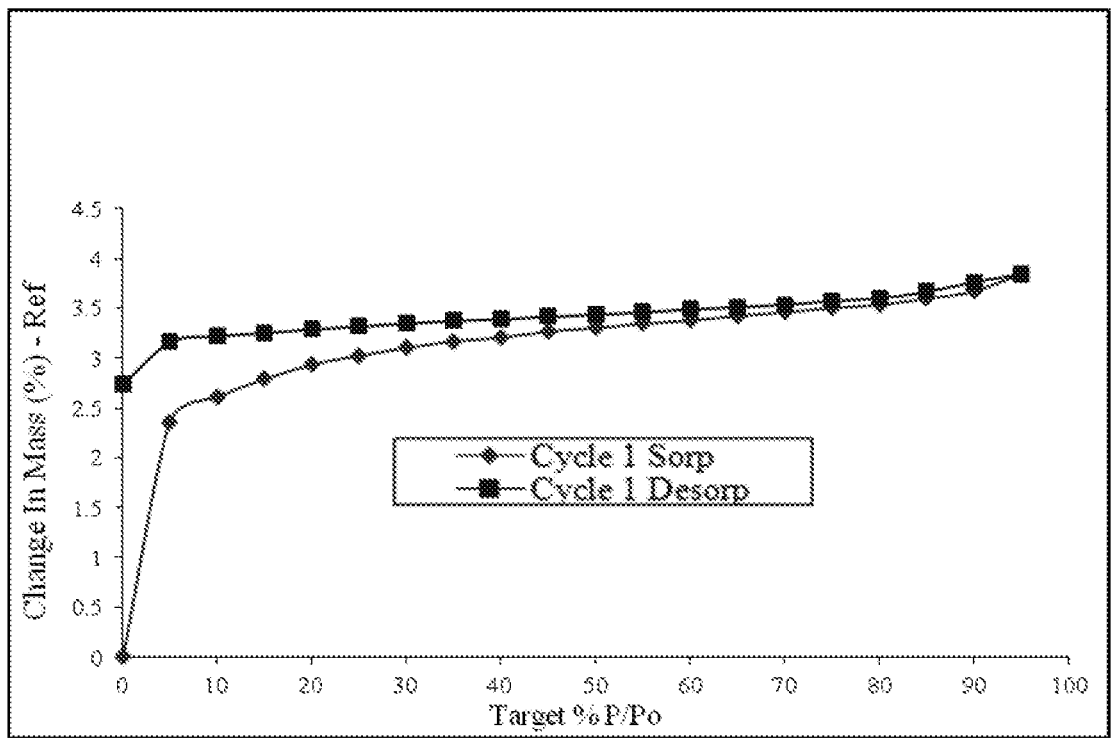
FIG. 27 shows a DVS pattern for crystal form B-1.
Figure 28:
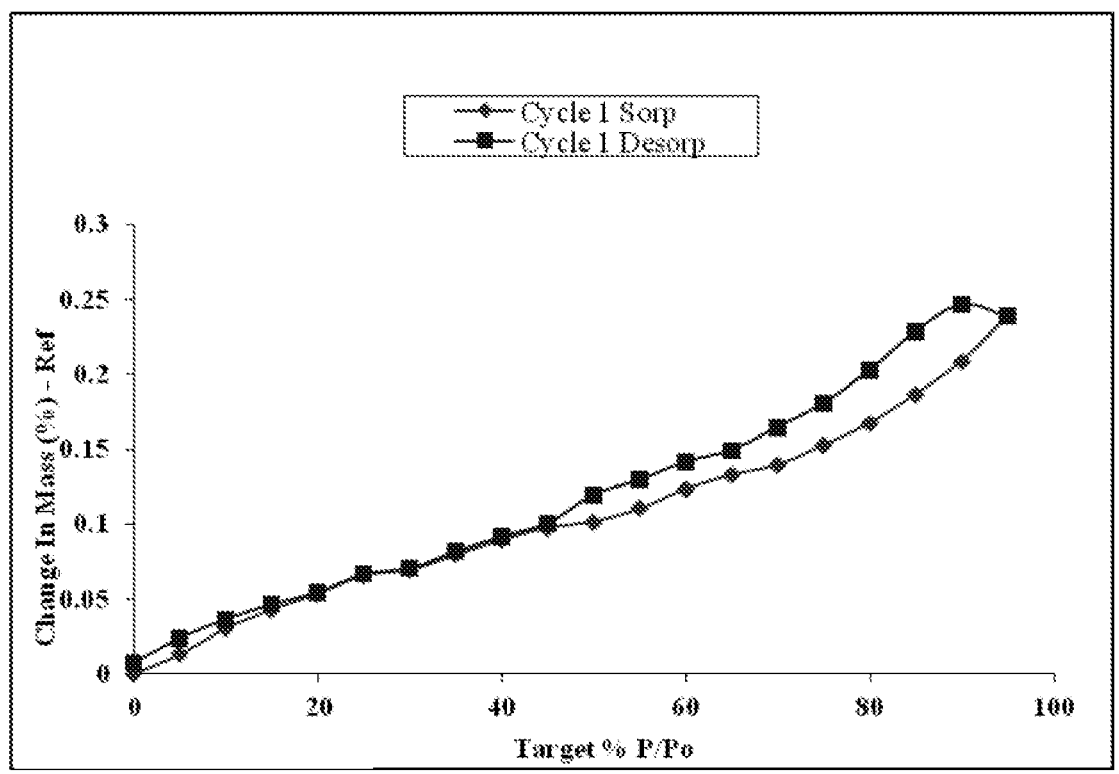
FIG. 28 shows a DVS pattern for crystal form C.
Figure 29:
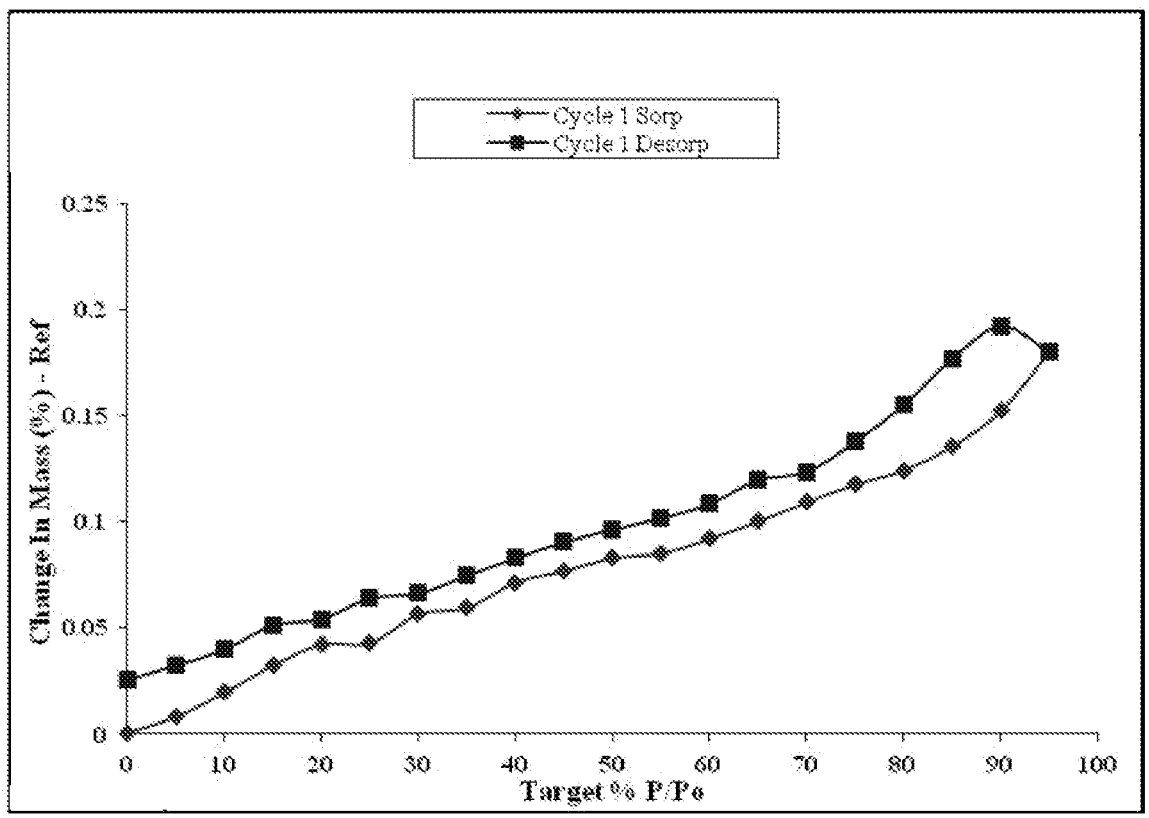
FIG. 29 shows a DVS pattern for crystal form D-2.
Figure 30:
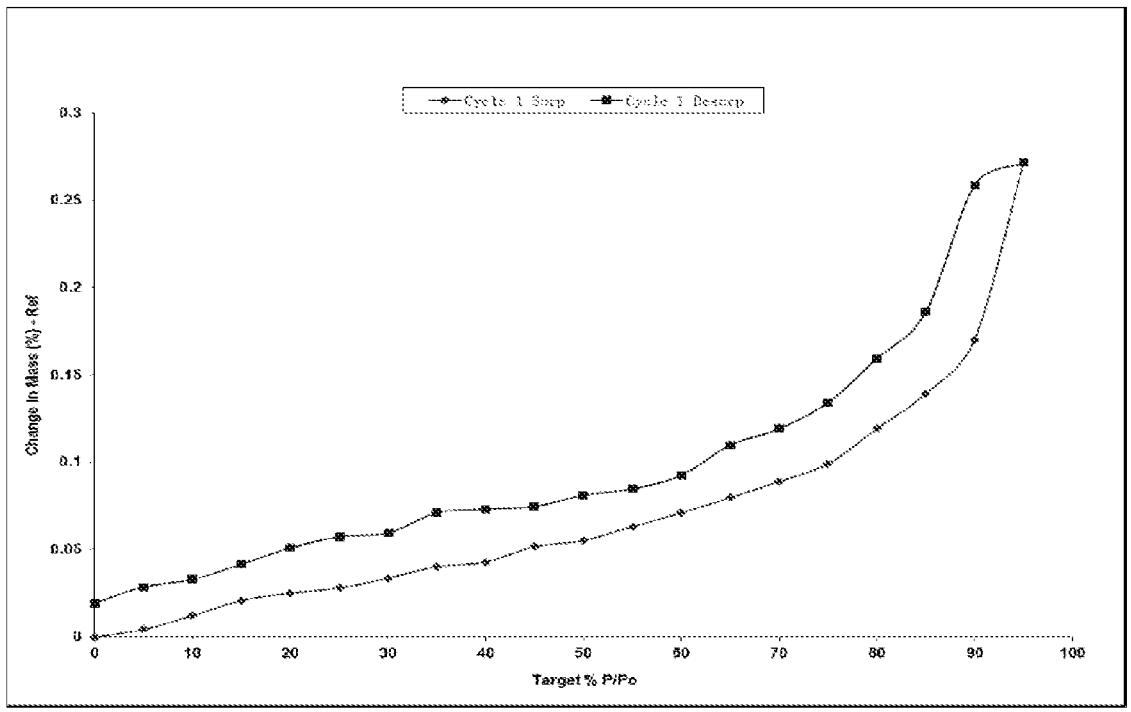
FIG. 30 shows a DVS pattern for crystal form E.
Figure 31:
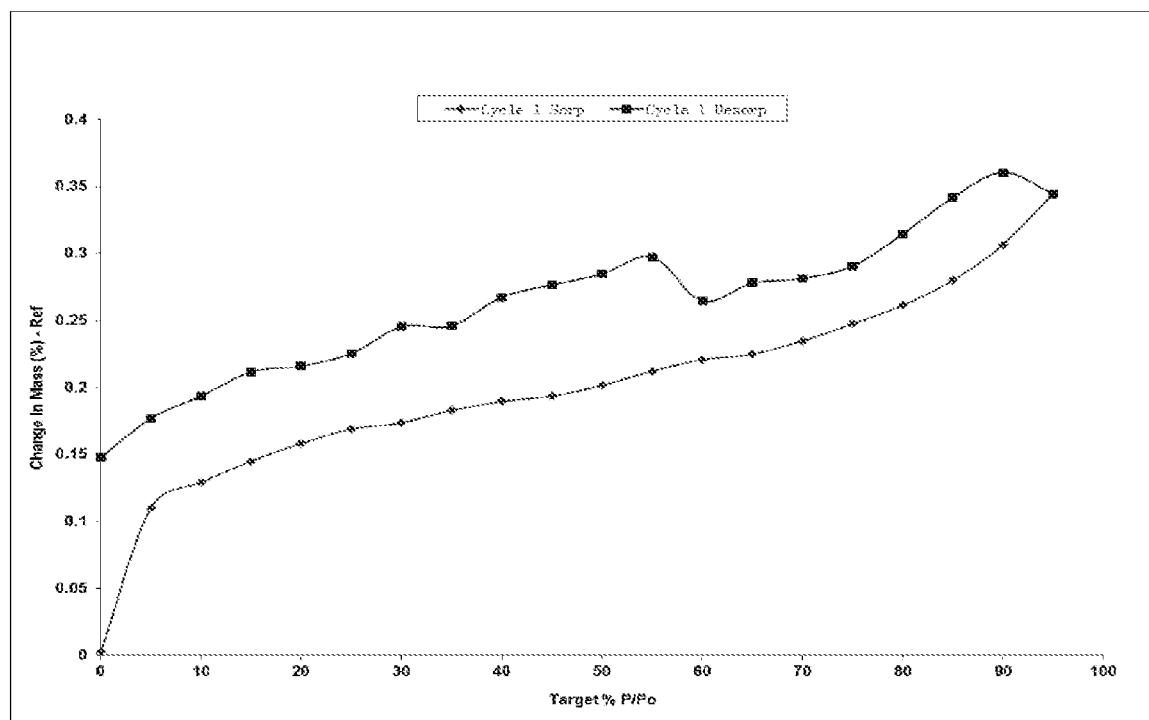
FIG. 31 shows a DVS pattern for crystal form F.

The DVS test results of the crystal form A and the crystal form B-1 were shown in FIG. 26 and FIG. 27, respectively. When the humidity was reduced to 10% RH at 25° C., the rate of weight loss of the sample was significantly increased. Therefore, the crystal form A and the crystal form B-1 are slightly hygroscopic.

The DVS test results of the crystal form C, crystal form D-2, crystal form E, and crystal form F were shown in FIG. 28, FIG. 29, FIG. 30, and FIG. 31. When the humidity increased to 80% RH at 25° C., the crystal form C, crystal form D-2, crystal form E and crystal form F absorbed 0.17%, 0.14%, 0.12%, 0.26% moisture respectively, indicating that the crystal form C, crystal form D-2, crystal form E, and crystal form F have almost no hygroscopicity.

Figure 23B:
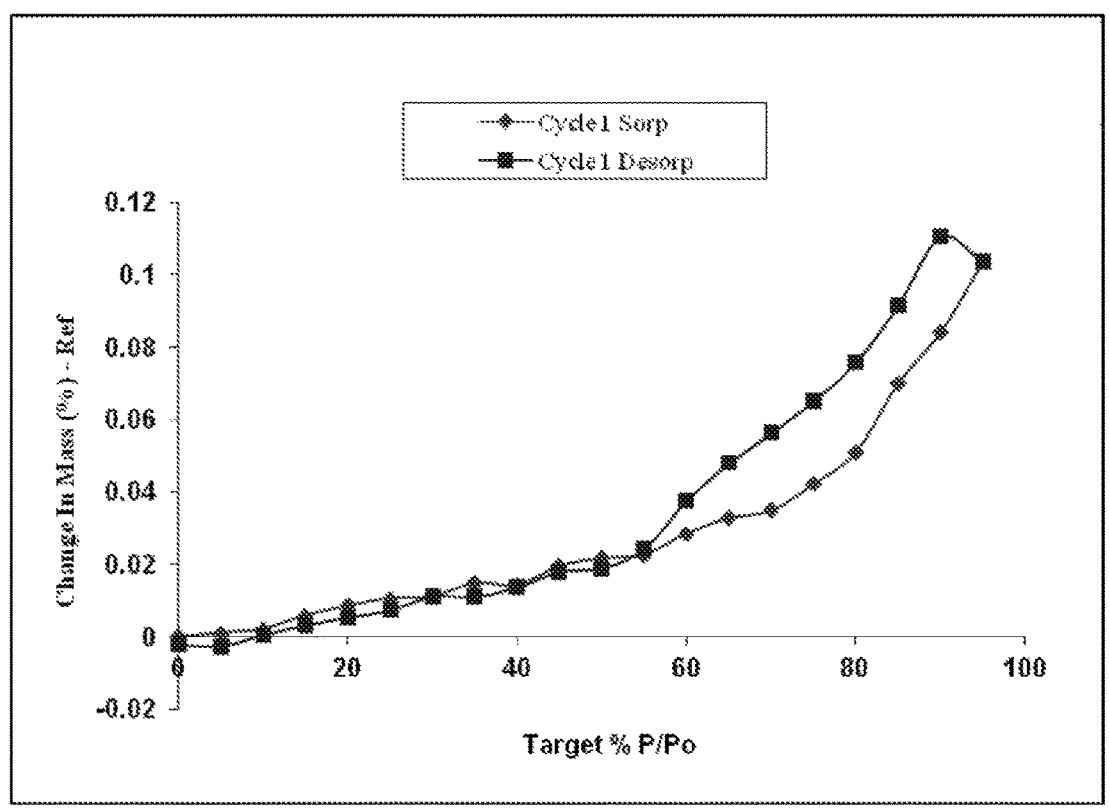
FIG. 23B shows a DVS pattern for crystal form I.
Figure 25B:
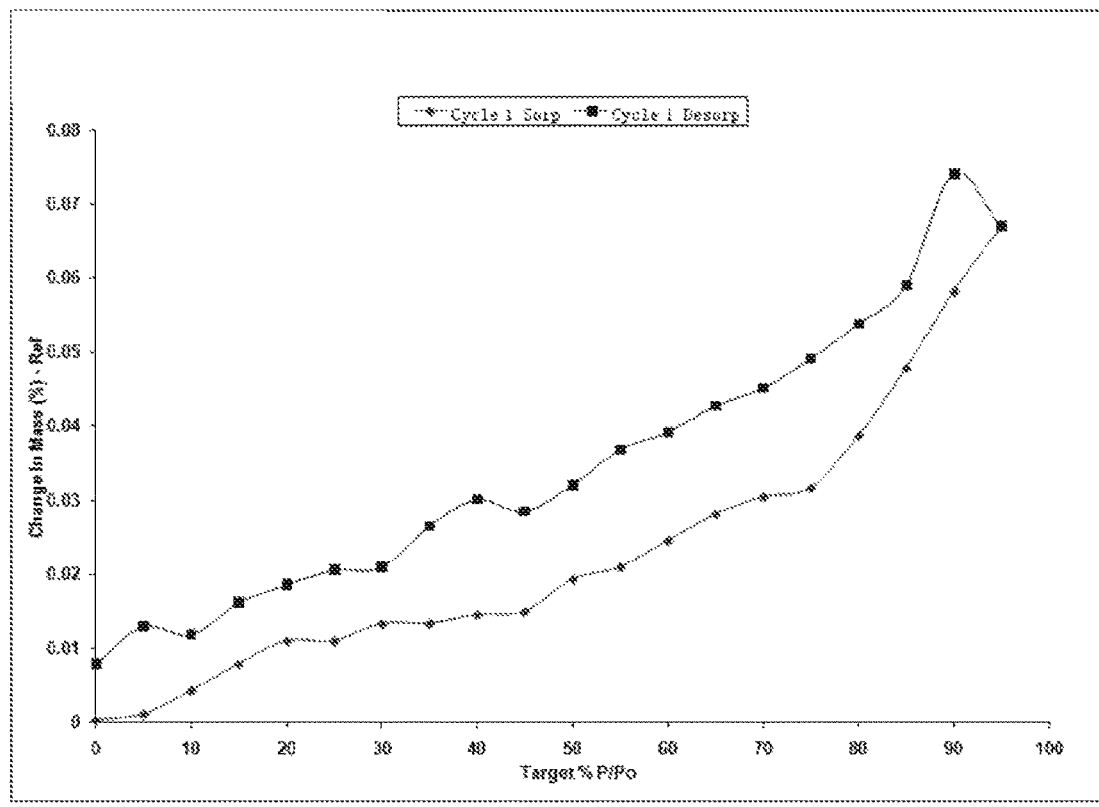
FIG. 25B shows a DVS pattern for crystal form II.

The DVS test results of the crystal form I and crystal form II were shown in FIG. 23B and FIG. 25B. When the humidity increased to 90% RH at 25° C., the crystal form I absorbed 0.084% of water, indicating that this crystal form has almost no hygroscopicity.

Example 17 Solubility Experiment

The solubilities of the following four kinds of salt and free base sample in 0.1M HCl, pH 4.5 buffer, pH 6.8 buffer, and water were tested at ambient temperature. In the test, the calibration curves of free base and four kinds of salt were plotted. 3 mg of solid samples of free base and four kinds of salt were weighed, respectively, and then 1 ml of the solvent was added, centrifuged after 30 min ultrasound. The supernatant was taken, and injected through the membrane, and the solubility was tested. The results are shown in the following table.

| Crystal form | Solubility (mg/mL) | | | |
|---|---|---|---|---|
| | pH 4.5 | pH 6.8 | 0.1M HCl | H$_2$O |
| Free base | 0.025 | 0.015 | >2.973 | 0.016 |
| crystal form A | 0.020 | 0.012 | >2.744 | 1.063 |
| crystal form B-1 | 0.026 | 0.012 | >2.488 | 0.946 |
| crystal form C | 0.027 | 0.010 | 1.875 | 0.174 |
| crystal form D-2 | 0.031 | 0.013 | 1.195 | 0.023 |

Compared with the free base, the solubility of the crystal form A, crystal form B-1, and crystal form C in water is obviously improved, while the solubility of the crystal form D-2 in water is slightly improved. The solubilities of four crystal forms in other three solvents are similar to that of the free base.

Example 18 Solubility Experiment

The solubility of the crystal form I in 11 common solvents at ambient temperature was tested. In the experiment, the crystal form I was formulated into standard solutions of different concentrations using 50% acetonitrile as solvent according to the following table, and injected to the HPLC instrument. The peak area was recorded and the standard curve was plotted, and the curve equation: y=11.30762x, $R^2$=0.99998, which has a good linear correlation in a range of 4.9 µg/ml~499 µg/ml was obtained. 10-80 mg of crystal form I was weighed into 0.5-10 ml of different solutions in the following table to prepare a saturated solution, sonicated for 3-5 min, dispersed evenly and then taken out, centrifuged at 12000 rpm for 5 min. The supernatant was drawn and diluted at a certain multiple, injected to the HPLC, the peak area was recorded, the sample concentration was calculated, and the pH of undiluted samples was determined.

Standard Curve of Crystal Form

| Sample concentration (µg/ml) | Peak area |
|---|---|
| 4.99 | 54.3 |
| 49.9 | 583.5 |
| 499 | 5640.6 |

Solubility of Crystal Form I

| Solution | Concentration (mg/ml) | Solubility (mg/ml) |
|---|---|---|
| methanol | 9.459 | >9.459 |
| ethanol | 4.68 | >4.68 |
| isopropanol | 1.837 | >1.837 |
| acetone | 28.464 | 28.464 |
| ethyl acetate | 12.441 | 12.441 |
| methyl tert-butyl ether | 1.044 | >1.044 |
| tetrahydrofuran | 78.135 | 78.135 |
| acetonitrile | 13.724 | 13.724 |
| water* | 0.185 | 0.185 |
| 50% acetonitrile | 10.998 | 10.998 |

Example 19 Pharmaceutical Composition

Tablets of crystal form C were prepared from the following components:

| crystal form C | 20 g |
|---|---|
| starch | 40 g |
| lactose | 32 g |
| PVP | 3 g |
| sodium carboxymethyl starch | 3 g |
| sodium dodecyl sulfate | 1 g |
| magnesium stearate | 1 g |

The crystal form C and starch were mixed and sieved, and then well mixed with the above other components, and tablets were compressed directly according to a conventional method.

Example 20 Pharmaceutical Composition

Tablets of crystal form D-2 were prepared from the following components:

| crystal form D-2 | 15 g |
|---|---|
| starch | 40 g |
| lactose | 37 g |
| PVP | 3 g |
| sodium carboxymethyl starch | 3 g |
| sodium dodecyl sulfate | 1 g |
| magnesium stearate | 1 g |

The crystal form D-2 and starch were mixed and sieved, and then well mixed with the above other components, and tablets were compressed directly according to a conventional method.

Example 21 Pharmaceutical Composition

Capsules of crystal form I were prepared from the following components:

| crystal form I | 20 g |
|---|---|
| starch | 40 g |
| lactose | 32 g |
| PVP | 3 g |
| sodium carboxymethyl starch | 3 g |
| sodium dodecyl sulfate | 1 g |
| magnesium stearate | 1 g |

The crystal form I and starch were mixed and sieved, and then well mixed with the above other components, and filled into ordinary gelatin capsules according to a conventional method.

Test Example 1: Determination of PI3K Kinase Activity

Test reagents and test methods.

The PI3K kinase used in the experiment: p110α/p85α (Invitrogen PV4788), p110β/p85α (Millipore 14-603), p110δ/p85α (Millipore 14-604M), and p110γ (Invitrogen PV4786). ADP transcreener kinase (3010-10 k) kit was purchased from Bellbrook labs.

The inhibition of PI3K kinase activity by the compound to be tested was determined by the following method. The working concentration of each component in the 25 µL enzyme reaction system was: p110α/p85α 3 ng (or p110β/p85α 60 ng, or p110δ/p85α 90 ng, or p110γ 100 ng), ATP 10 µM, PIP2: PS (Invitrogen PV5100) 30 µM and the DMSO concentration was 2% after addition of the compound to be tested.

At the time of the test, the compound to be tested was dissolved in dimethylsulfoxide according to the desired concentration of the experiment. The compound to be tested was gradiently diluted 3 times (0.00046-1 µM, 8 concentration points) with 10% DMSO. 5 µL of the compound to be tested was added to each well of a 96-well plate (Greiner 675076) in duplicate. 2.5×buffer was prepared and 1 µL of DTT (Millipore 20-265) was added to each 800 µL of 2.5×buffer. ATP/PIP2: PS enzyme/substrate working solution and the PI3K enzyme working solution in proper concentration were prepared with 2.5×buffer. 10 µL of ATP/PIP2: PS and 10 µL of the PI3K enzyme working solution were added to each well in a 96-well plate. The plate was shaken and mixed uniformly, and then incubated at 25° C. for 1 hour. At the same time, ADP and ATP (0.01 µM, 0.02 µM, 0.04 µM, 0.06 µM, 0.08 µM, 0.08 µM, 0.1 µM, 0.25 µM, 0.5 µM, 1 µM, 2 µM, 5 µM, 10 µM, and 12 concentration points) were diluted with buffer to set the standard curve. After completion of the enzyme reaction, 25 µL of ADP assay solution (1% 100×ADP tracer, 0.79% ADP antibody and 10% 10× reaction stop solution) was added and incubated at 25° C. for 1 hour. Fluorescence polarization value [mP] of each well was measured with a Perkin Elmer Victor X5 Fluorescent Microplate. The ADP concentration [ADP] was calculated from the ADP/ATP standard curve and the $IC_{50}$ values were calculated using the XLFit software. The measured $IC_{50}$ values of inhibitory activities of the compounds tested against PI3K kinase are shown in Table 1.

TABLE 1

$IC_{50}$ values of inhibitory activities of the compound of the present disclosure against PI3K kinase

| Compound No. | PI3K-α/nM | PI3K-β/nM | PI3K-γ/nM | PI3K-δ/nM |
|---|---|---|---|---|
| Compound of formula X | 4 | 28 | 114 | 84 |
| Comparative compound 2 | 90 | 2161 | >3000 | 2578 |

TABLE 2

$IC_{50}$ values of inhibitory activities of the compound of the present disclosure against PI3K-α kinase

| Compound No. | PI3K-α/nM |
|---|---|
| Compound of formula X | 4 |
| Comparative compound 3 | >1000 |

As can be seen from Table 1, the compound of formula X has a significant inhibitory effect on all the PI3K kinases (PI3K-α, PI3K-β, PI3K-γ, and PI3K-δ), which means that the compound of formula X has some selective inhibitory effect on PI3K-α.

As can be seen from Table 2, the compound of formula X has a strong inhibitory effect on the PI3 K-α kinase, and the study has shown that when the substituent at position 4 of the pyrimidine ring is replaced by phenyl, the inhibitory effect on PI3K-α kinase is significantly reduced.

In addition, the compound of formula X has an inhibitory activity against PI3K-α kinase higher than that of the positive compound BKM-120 ($IC_{50}$=57), wherein the inhibitory activity is increased by about 10 times.

Test Example 2: Inhibition of P-AKt Phosphorylation Level in PC-3 Cells

This experiment was performed by cell level fluorescence image processing method.

I. Reagents and Solutions

Triton X-100: 10% aqueous Triton X-100 solution (Sigma T8787-100 mL) was prepared, stored at 4° C. and diluted by 1:100 to give 0.1% Triton X-100 aqueous solution for use in the experiment.

Prodium Iodide (PI): 1 mg/mL (1.5 mM) PI (Sigma P4170) storage solution was prepared with PBS and stored at −25° C. in the dark. For use, the PI storage solution was diluted with PBS by 1: 1000 to give a 1.5 µM solution and used in dark.

II. PC-3 Cells 2.1 PC-3 Cell Treatment

PC-3 cells in logarithmic growth phase were digested with 0.25% EDTA trypsin. 3000 cells/90 µL were seeded in a 96-well plate (BD 356692) and cultured at 37° C. and 5% $CO_2$. After the cells adhered, 10 µL of the compound to be tested which was gradiently diluted 3 times (0.0046 to 10 µM, 8 concentration points, in duplicate) was added and incubated for 2 hours, followed by addition of 100 µL of 4% paraformaldehyde (DINGGUO AR-0211) and incubated at room temperature for 45 minutes. Then 100 µL of 0.1% Triton X-100 solution was added and incubated for another 30 minutes.

2.2 Detection Step

Triton X-100 solution was removed and the cells were rinsed with 200 µl of PBS twice (300 rpm vibration for 1 minute). The blocking solution (1% BSA solution in PBS) (Genview FA016-100G) was added and incubated at room temperature for 2 hours. The plate was rinsed with PBS once (300 rpm, 1 min) and 30 µL of Ser473-p-Akt antibody (cell signaling 4060L) diluted with 0.1% BSA was added and incubated overnight at 4° C. Ser473-p-Akt antibody was removed and the plate was rinsed with PBS twice (300 rpm, 1 minute). 35 µL of Alexa Flour 488 donkey anti-rabbit IgG (Invitrogen A21206) was added and incubated at room temperature for 1.5 hours. The plate was rinsed with PBS twice (300 rpm, 1 minute) and 35 µL of 1.5 µM PI was added and incubated at room temperature for 0.5 h. The fluorescence intensity was measured with Acumen eX3 (TTP LabTech).

2.3 Data Analysis

10 µM BEZ235 (Selleck S1009) treatment group was negative control and DMSO treatment group was positive control.

Inhibition ratio %=[1−(the mean value of the fluorescence intensity of the compound to be tested−the mean value of the fluorescence intensity of the negative control group)/(the mean value of the fluorescence intensity of the positive control group−the mean value of the fluorescence intensity of the negative control group)]×100%

2.4 $IC_{50}$ values were calculated based on the calculated inhibition ratios by using XLFIT 5.0 software and shown in Table 3.

TABLE 3

The measured $IC_{50}$ values of the compound of the present disclosure for PC-3 cell activity

| Compound No. | PC-3 cell ($IC_{50}$/nM) |
|---|---|
| Compound of formula X | 198 |
| BKM-120 (Positive control) | 596 |
| Comparative compound 1 | 2257 |
| Comparative compound 2 | 1025 |

As can be seen from Table 3, the compound of formula X has a good inhibitory activity against Akt phosphorylation in PC-3 cells. The compound of formula X has a stronger inhibitory activity against Akt phosphorylation in PC-3 cells compared with the positive compound BKM-120 and comparative compounds 1 and 2.

Test Example 4: Cell Inhibitory Activity Detected by MTT Assay

The MTT assay procedure and steps were carried out as well known to those skilled in the art, and all the reagents used in the methods were commercially available.

The cells in logarithmic growth phase were digested with 0.25% EDTA trypsin (Gibco, 25200-056) and resuspended in fresh medium. 90 μL of the cell suspension was inoculated into a 96-well cell culture plate (BD Faclon 353072) with a suitable cell density and cultured at 37° C. under 5% $CO_2$. After the cells adhered, 10 μL of the test compound at different concentrations (0.0046-10 μM, 8 concentration points) was added and incubated for another 72 h. 10 μL of MTT (5 mg/mL PBS solution) (Sigma, M5655) was added to react for 4 h. The absorbance at 492 nm was measured by using Thermo Scientific Multiskan MK3 microplate reader and $IC_{50}$ was calculated using XLFIT 5.0 software (UK IDBS).

T47D cell culture medium: RPMI-1640 medium (Hyclone SH30809.01B)+10% FBS (Gibco 10099-141)

MCF-7 cell culture medium: DMEM medium (Hyclone SH30243.01B+10% FBS (Gibco 10099-141)

NIH3T3 cell culture medium: DMEM medium (Hyclone SH30243.01B+10% FBS (Gibco 10099-141)

TABLE 4

$IC_{50}$ values of the compound of the present disclosure for T47D cell growth inhibition

| Compound No. | T47D cell ($IC_{50}$/nM) |
| --- | --- |
| Compound of formula X | 202 |
| Comparative compound 1 | 1220 |
| Comparative compound 2 | 854 |

TABLE 5

$IC_{50}$ values of the compound of the present disclosure for MCF-7 cell growth inhibition

| Compound No. | MCF-7 cell ($IC_{50}$/nM) |
| --- | --- |
| Compound of formula X | 258 |
| Comparative compound 1 | 996 |
| Comparative compound 2 | 639 |

As shown in Table 4 and Table 5, the compound of formula X exhibits significant proliferation inhibitory activity against the breast cancer cell lines T47D and MCF-7. Compared with the comparative compounds 1 and 2, the compound of formula X has significantly stronger inhibitory activity against the proliferation of the above two cell lines.

The studies show that the substitution position of the morpholine ring on the pyrimidine ring has a great effect on the inhibitory activity on the cell lines. When the substituent morpholine ring is at position 4 or 6, the inhibitory activity of the compound on the cell lines is significantly reduced in comparison with the position 2 substitution.

Test Example 5: Metabolism Stability Assay

1. Preparation of Buffer

Buffer A: 1 L solution of 100 mM potassium dihydrogen phosphate containing 1 mM EDTA (Sigma, V900157-100G) was prepared. Buffer B: 1 L solution of 100 mM dipotassium hydrogen phosphate containing 1 mM EDTA was prepared. Buffer C: 700 mL of buffer B was taken out and titrated with buffer A to pH 7.4.

2. Preparation of the compound to be tested and the positive control drug (ketanserin (Sigma S006-10MG))

2.1 10 μl of 10 mM compound to be tested and 10 μl of 10 mM ketanserin were taken out and 190 μl of pure acetonitrile was added to each of them to prepare 500 μM compound to be tested and ketanserin, respectively.

2.2 20 μl (20 mg/mL) of liver microsomes (XENOTECH, H0610) stock solution was added to 513.4 μl of buffer C on wet ice. 0.75 mg/mL liver microsomal solution was obtained.

2.3 1.5 μl of each of the above-mentioned compound to be tested and ketanserin solution was added to 498.5 μl of liver microsomal solution (0.7 5 mg/mL) respectively on wet ice. 1.5 μM mixed solution of compound to be tested and 1.5 μM mixed solution of ketanserin were obtained.

2.4 At the time points 0, 5, 15, 30, 45, and 60 min, 30 μl of the mixed solution of compound to be tested and 30 μl of the mixed solution of ketanserin were dispensed into the reaction plate on wet ice, respectively.

2.5 5 mg reduced coenzyme II (Roche, 10621706001) was weighed and dissolved in 1 mL of buffer C. 6 mM reduced coenzyme II solution was obtained. The reduced coenzyme II solution was dispensed into the reaction plate.

2.6 Imipramine was dissolved to give a 10 mM solution. 10 μl imipramine solution was added to 100 mL of blank acetonitrile to generate the internal reference.

2.7 At 0 min, 135 μL of iced acetonitrile (Merck, UN 1648) containing the internal reference was added to each well and then 15 μL of buffer C was added.

2.8 The reaction plate was placed into a 37° C. water bath incubator for 5 min. In the reaction plate, 15 μL of reduced coenzyme II solution was added to each well to initiate the reaction, and the time keeping was started. At the time points of 5, 15, 30, 45, and 60 min, 135 μL of iced acetonitrile containing the internal reference was added to each well to terminate the reaction.

2.9 The reaction plate was sealed with an aluminum film, placed on a vibration mixer and shaken at 500 rpm for 5 min. The plate was then centrifuged in a centrifuge at 3750 rp for 15 min.

2.10 The sample was diluted with pure water in accordance with the ratio of 1:1 and detected by LC/MS. The clearance ratio was calculated according to the following formula based on the obtained values, and shown in Table 7.

Half-life: 0.693/K (the slope by plotting based on the incubation time and logarithm of the concentration value)

Clearance ratio: (0.693/half-life)*(1/protein concentration (0.5 mg/mL))*(proportional factor)

Wherein, the K value and the proportional factor were calculated by those skilled in the art according to the methods described in the prior art and contained in the instructions of the liver microsome product.

TABLE 7

Clearance ratio of liver microsomal metabolism in mice

| Compound No. | Clearance ratio (mL/min/kg) mouse |
| --- | --- |
| Compound of formula X | 108.9 |
| BKM-120 | 151.3 |

It can be seen from Table 7 that the metabolic stability of the compound of formula X is improved compared to the positive compound BKM-120.

All publications mentioned herein are incorporated by reference as if each individual document was cited as a reference, as in the present application. It should also be understood that, after reading the above teachings of the present disclosure, those skilled in the art can make various changes or modifications, equivalents of which falls in the scope of claims as defined in the appended claims.

What is claimed is:

1. A crystal form of a compound of formula X, or a crystal form of a pharmaceutically acceptable salt of the compound of formula X:

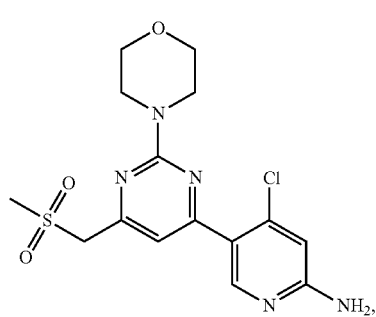

(X)

wherein the crystal form is selected from the group consisting of:

(1) form A crystal of a hydrochloride of the compound of formula X, i.e., crystal form A, having an X-ray powder diffraction pattern comprising diffraction angle 2θ(°) values of the following group A1: 5.57±0.10, 8.87±0.10, 20.77±0.10, 22.09±0.10, 24.15±0.10, and 28.27±0.10;

(2) form B-1 crystal of a sulfate of the compound of formula X, i.e., crystal form B-1, having an X-ray powder diffraction pattern comprising diffraction angle 2θ(°) values of the following group B1: 9.83±0.10, 18.51±0.10, 21.11±0.10, 21.75±0.10, and 27.29±0.10;

(3) form B-2 crystal of a sulfate of the compound of formula X, i.e., crystal form B-2, having an X-ray powder diffraction pattern comprising diffraction angle 2θ(°) values of the following group B1': 16.42±0.10, 20.17±0.10, 22.25±0.10, 23.00±0.10, 23.97±0.10, 25.30±0.10, and 27.98±0.10;

(4) form C crystal of a maleate of the compound of formula X, i.e., crystal form C, having an X-ray powder diffraction pattern comprising diffraction angle 2θ(°) values of the following group C1: 8.35±0.10, 8.92±0.10, 16.91±0.10, 20.35±0.10, 21.40±0.10, 23.70±0.10, 24.98±0.10, and 25.47±0.10;

(5) form D-1 crystal of a fumarate of the compound of formula X, i.e., crystal form D-1, having an X-ray powder diffraction pattern comprising diffraction angle 2θ(°) values of the following group D1: 9.07±0.10, 12.48±0.10, 16.85±0.10, 18.93±0.10, 20.07±0.10, 21.21±0.10, 22.96±0.10, 25.56±0.10, 27.50±0.10, 30.72±0.10, 31.45±0.10, and 32.69±0.10;

(6) form D-2 crystal of a fumarate of the compound of formula X, i.e., crystal form D-2, having an X-ray powder diffraction pattern comprising diffraction angle 2θ(°) values of the following group D1': 14.76±0.10, 19.74±0.10, and 26.69±0.10;

(7) form E crystal of a methanesulfonate of the compound of formula X, i.e., crystal form E, having an X-ray powder diffraction pattern comprising diffraction angle 2θ(°) values of the following group E1: 7.92±0.10, 16.07±0.10, 18.74±0.10, 20.25±0.10, 20.61±0.10, 22.08±0.10, 24.30±0.10, and 31.04±0.10;

(8) form F crystal of an L-tartrate of the compound of formula X, i.e., crystal form F, having an X-ray powder diffraction pattern comprising diffraction angle 2θ(°) values of the following group F1: 11.22±0.10, 19.80±0.10, 20.35±0.10, 20.66±0.10, and 23.44±0.10;

(9) form G-1 crystal of a phosphate of the compound of formula X, i.e., crystal form G-1, having an X-ray powder diffraction pattern comprising diffraction angle 2θ(°) values of the following group G1: 9.43±0.10, 17.30±0.10, 18.82±0.10, 19.41±0.10, 20.91±0.10, 22.40±0.10, 27.44±0.10, and 29.43±0.10;

(10) form G-2 crystal of a phosphate of the compound of formula X, i.e., crystal form G-2, having an X-ray powder diffraction pattern comprising diffraction angle 2θ(°) values of the following group G1': 19.26±0.10, 21.00±0.10, and 24.15±0.10;

(11) form G-3 crystal of a phosphate of the compound of formula X, i.e., crystal form G-3, having an X-ray powder diffraction pattern comprising diffraction angle 2θ(°) values of the following group G1": 15.11±0.10, 16.16±0.10, 18.84±0.10, 19.90±0.10, 21.32±0.10, 23.40±0.10, 24.21±0.10, 24.75±0.10, 26.16±0.10, and 30.55±0.10;

(12) form H-1 crystal of a citrate of the compound of formula X, i.e., crystal form H-1, having an X-ray powder diffraction pattern comprising diffraction angle 2θ(°) values of the following group H1: 14.01±0.10, 21.04±0.10, 28.26±0.10, and 35.54±0.10;

(13) form H-2 crystal of a citrate of the compound of formula X, i.e., crystal form H-2, having an X-ray powder diffraction pattern comprising diffraction angle 2θ(°) values of the following group H1': 17.75±0.10, 20.15±0.10, 22.25±0.10, 26.28±0.10, and 30.04±0.10;

(14) form H-3 crystal of a citrate of the compound of formula X, i.e., crystal form H-3, having an X-ray powder diffraction pattern comprising diffraction angle 2θ(°) values of the following group H1": 15.62±0.10, 19.67±0.10, 20.01±0.10, 23.01±0.10, 26.82±0.10, and 27.65±0.10;

(15) form J crystal of a hydrobromide of the compound of formula X, i.e., crystal form J, having an X-ray powder diffraction pattern comprising diffraction angle 2θ(°) values of the following group J1: 20.71±0.10, 22.07±0.10, 22.84±0.10, 24.13±0.10, 25.00±0.10, 26.85±0.10, 28.26±0.10, and 31.38±0.10;

(16) form I crystal of a free base of the compound of formula X, i.e., crystal form I, having an X-ray powder diffraction pattern comprising diffraction angle 2θ(°) values of the following group I1: 12.37±0.10, 14.99±0.10, 16.11±0.10, 21.03±0.10, 22.65±0.10, and 24.30±0.10; and

(17) form II crystal of a free base of the compound of formula X, i.e., crystal form II, having an X-ray powder diffraction pattern comprising diffraction angle 2θ(°) values of the following group II1: 15.34±0.10, 16.57±0.10, 16.86±0.10, 17.33±0.10, 22.68±0.10, 24.36±0.10, 24.95±0.10, 25.51±0.10, and 26.53±0.10.

2. The crystal form of the compound of formula X, or the crystal form of the pharmaceutically acceptable salt of the compound of formula X according to claim 1, wherein the crystal form is selected from the group consisting of:

(1) form A crystal of a hydrochloride of the compound of formula X, i.e., crystal form A, having an X-ray powder diffraction pattern comprising diffraction angle 2θ(°)

values of the following group A1: 5.57±0.10, 8.87±0.10, 20.77±0.10, 22.09±0.10, 24.15±0.10, and 28.27±0.10;

(2) form B-1 crystal of a sulfate of the compound of formula X, i.e., crystal form B-1, having an X-ray powder diffraction pattern comprising diffraction angle 2θ(°) values of the following group B1: 9.83±0.10, 18.51±0.10, 21.11±0.10, 21.75±0.10, and 27.29±0.10;

(3) form B-2 crystal of a sulfate of the compound of formula X, i.e., crystal form B-2, having an X-ray powder diffraction pattern comprising diffraction angle 2θ(°) values of the following group B1': 16.42±0.10, 20.17±0.10, 22.25±0.10, 23.00±0.10, 23.97±0.10, 25.30±0.10, and 27.98±0.10;

(4) form C crystal of a maleate of the compound of formula X, i.e., crystal form C, having an X-ray powder diffraction pattern comprising diffraction angle 2θ(°) values of the following group C1: 8.35±0.10, 8.92±0.10, 16.91±0.10, 20.35±0.10, 21.40±0.10, 23.70±0.10, 24.98±0.10, and 25.47±0.10;

(5) form D-1 crystal of a fumarate of the compound of formula X, i.e., crystal form D-1, having an X-ray powder diffraction pattern comprising diffraction angle 2θ(°) values of the following group D1: 9.07±0.10, 12.48±0.10, 16.85±0.10, 18.93±0.10, 20.07±0.10, 21.21±0.10, 22.96±0.10, 25.56±0.10, 27.50±0.10, 30.72±0.10, 31.45±0.10, and 32.69±0.10;

(6) form D-2 crystal of a fumarate of the compound of formula X, i.e., crystal form D-2, having an X-ray powder diffraction pattern comprising diffraction angle 2θ(°) values of the following group D1': 14.76±0.10, 19.74±0.10, and 26.69±0.10;

(7) form E crystal of a methanesulfonate of the compound of formula X, i.e., crystal form E, having an X-ray powder diffraction pattern comprising diffraction angle 2θ(°) values of the following group E1: 7.92±0.10, 16.07±0.10, 18.74±0.10, 20.25±0.10, 20.61±0.10, 22.08±0.10, 24.30±0.10, and 31.04±0.10;

(8) form F crystal of an L-tartrate of the compound of formula X, i.e., crystal form F, having an X-ray powder diffraction pattern comprising diffraction angle 2θ(°) values of the following group F1: 11.22±0.10, 19.80±0.10, 20.35±0.10, 20.66±0.10, and 23.44±0.10;

(9) form G-1 crystal of a phosphate of the compound of formula X, i.e., crystal form G-1, having an X-ray powder diffraction pattern comprising diffraction angle 2θ(°) values of the following group G1: 9.43±0.10, 17.30±0.10, 18.82±0.10, 19.41±0.10, 20.91±0.10, 22.40±0.10, 27.44±0.10, and 29.43±0.10;

(10) form G-2 crystal of a phosphate of the compound of formula X, i.e., crystal form G-2, having an X-ray powder diffraction pattern comprising diffraction angle 2θ(°) values of the following group G1': 19.26±0.10, 21.00±0.10, and 24.15±0.10;

(11) form G-3 crystal of a phosphate of the compound of formula X, i.e., crystal form G-3, having an X-ray powder diffraction pattern comprising diffraction angle 2θ(°) values of the following group G1": 15.11±0.10, 16.16±0.10, 18.84±0.10, 19.90±0.10, 21.32±0.10, 23.40±0.10, 24.21±0.10, 24.75±0.10, 26.16±0.10, and 30.55±0.10;

(12) form H-1 crystal of a citrate of the compound of formula X, i.e., crystal form H-1, having an X-ray powder diffraction pattern comprising diffraction angle 2θ(°) values of the following group H1: 14.01±0.10, 21.04±0.10, 28.26±0.10, and 35.54±0.10;

(13) form H-2 crystal of a citrate of the compound of formula X, i.e., crystal form H-2, having an X-ray powder diffraction pattern comprising diffraction angle 2θ(°) values of the following group H1': 17.75±0.10, 20.15±0.10, 22.25±0.10, 26.28±0.10, and 30.04±0.10;

(14) form H-3 crystal of a citrate of the compound of formula X, i.e., crystal form H-3, having an X-ray powder diffraction pattern comprising diffraction angle 2θ(°) values of the following group H1": 15.62±0.10, 19.67±0.10, 20.01±0.10, 23.01±0.10, 26.82±0.10, and 27.65±0.10; and

(15) form J crystal of a hydrobromide of the compound of formula X, i.e., crystal form J, having an X-ray powder diffraction pattern comprising diffraction angle 2θ(°) values of the following group J1: 20.71±0.10, 22.07±0.10, 22.84±0.10, 24.13±0.10, 25.00±0.10, 26.85±0.10, 28.26±0.10, and 31.38±0.10.

3. The crystal form of the compound of formula X, or the crystal form of the pharmaceutically acceptable salt of the compound of formula X according to claim 1, wherein the crystal form is the form C crystal of a maleate of the compound of formula X, i.e., crystal form C, having an X-ray powder diffraction pattern comprising diffraction angle 2θ(°) values of the following group C1: 8.35±0.10, 8.92±0.10, 16.91±0.10, 20.35±0.10, 21.40±0.10, 23.70±0.10, 24.98±0.10, and 25.47±0.10.

4. The crystal form of the compound of formula X, or the crystal form of the pharmaceutically acceptable salt of the compound of formula X according to claim 1, wherein
the X-ray powder diffraction pattern of the crystal form A is substantially characterized as in FIG. 1;
the X-ray powder diffraction pattern of the crystal form B-1 is substantially characterized as in FIG. 3;
the X-ray powder diffraction pattern of the crystal form B-2 is substantially characterized as in FIG. 5;
the X-ray powder diffraction pattern of the crystal form C is substantially characterized as in FIG. 6;
the X-ray powder diffraction pattern of the crystal form D-1 is substantially characterized as in FIG. 8;
the X-ray powder diffraction pattern of the crystal form D-2 is substantially characterized as in FIG. 9;
the X-ray powder diffraction pattern of the crystal form E is substantially characterized as in FIG. 11;
the X-ray powder diffraction pattern of the crystal form F is substantially characterized as in FIG. 13;
the X-ray powder diffraction pattern of the crystal form G-1 is substantially characterized as in FIG. 15;
the X-ray powder diffraction pattern of the crystal form G-2 is substantially characterized as in FIG. 16;
the X-ray powder diffraction pattern of the crystal form G-3 is substantially characterized as in FIG. 17;
the X-ray powder diffraction pattern of the crystal form H-1 is substantially characterized as in FIG. 18;
the X-ray powder diffraction pattern of the crystal form H-2 is substantially characterized as in FIG. 19;
the X-ray powder diffraction pattern of the crystal form H-3 is substantially characterized as in FIG. 20; and/or
the X-ray powder diffraction pattern of the crystal form J is substantially characterized as in FIG. 21.

5. A method of preparing the crystal form of the compound of formula X, or the crystal form of the pharmaceutically acceptable salt of the compound of formula X according to claim 1, comprising the steps of:
(1) reacting a compound X-e with a compound X-f in an inert solvent to form the compound of formula X;

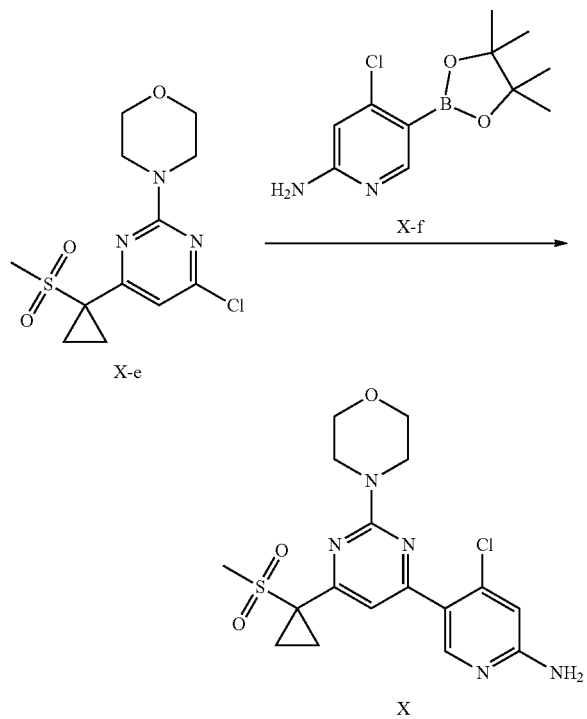

(2) performing a salt forming reaction to the compound of formula X with an acid, thereby forming the pharmaceutically acceptable salt of the compound of formula X; and (3) crystallizing the compound of formula X formed in step (1) or the pharmaceutically acceptable salt of the compound of formula X formed in step (2), thereby obtaining a polymorph of the compound of formula X or a polymorph of the pharmaceutically acceptable salt of the compound of formula X, wherein the acid in step (2) is selected from the group consisting of hydrochloric acid, sulfuric acid, maleic acid, fumaric acid, methanesulfonic acid, L-tartaric acid, phosphoric acid, citric acid, and hydrobromic acid.

6. A pharmaceutical composition, comprising:
(a) a crystal form of the compound of formula X, or the crystal form of the pharmaceutically acceptable salt of the compound of formula X according to claim 1; and
(b) a pharmaceutically acceptable carrier.

7. The crystal form of the compound of formula X, or the crystal form of the pharmaceutically acceptable salt of the compound of formula X according to claim 1, wherein
the X-ray powder diffraction pattern of the crystal form I is substantially characterized as in FIG. 22; and/or
the X-ray powder diffraction pattern of the crystal form II is substantially characterized as in FIG. 24.

\* \* \* \* \*